(12) United States Patent
Minvielle

(10) Patent No.: US 9,541,536 B2
(45) Date of Patent: Jan. 10, 2017

(54) PRESERVATION SYSTEM FOR NUTRITIONAL SUBSTANCES

(71) Applicant: Eugenio Minvielle, Rye, NY (US)

(72) Inventor: Eugenio Minvielle, Rye, NY (US)

( * ) Notice: Subject to any disclaimer, the term of this patent is extended or adjusted under 35 U.S.C. 154(b) by 82 days.

(21) Appl. No.: 13/729,548

(22) Filed: Dec. 28, 2012

(65) Prior Publication Data

US 2013/0273222 A1    Oct. 17, 2013

Related U.S. Application Data

(63) Continuation-in-part of application No. 13/485,854, filed on May 31, 2012.
(Continued)

(51) Int. Cl.
*A23L 3/375* (2006.01)
*G01N 33/02* (2006.01)
(Continued)

(52) U.S. Cl.
CPC .............. *G01N 33/02* (2013.01); *A23B 4/09* (2013.01); *A23B 5/055* (2013.01); *A23B 7/055* (2013.01);
(Continued)

(58) Field of Classification Search
CPC ........ G01N 33/02; G01N 25/00; G01N 21/00; G01N 33/0004; G01N 29/00; G01N 7/00; G01M 3/00; G05B 15/02; A23L 3/001; A23L 3/36–3/375; G06Q 30/06; G06F 17/30386; A23B 4/06–4/09; A23B 5/04–5/055; A23B 7/04–7/055; A23B 9/10–9/12
(Continued)

(56) References Cited

U.S. PATENT DOCUMENTS 3,685,308 A  *  8/1972  Lundquist ..................... 62/60
4,225,410 A      9/1980  Pace
(Continued)

FOREIGN PATENT DOCUMENTS

CN    101173316      5/2008
CN    102033043 A    4/2011
(Continued)

OTHER PUBLICATIONS

Office Action in U.S. Appl. No. 13/485,850, mailed Sep. 29, 2014.
(Continued)

*Primary Examiner* — Drew Becker
(74) *Attorney, Agent, or Firm* — Nixon Peabody LLP

(57) ABSTRACT

Disclosed herein is preservation system for nutritional substances. The preservation system obtains information about the nutritional substance to be preserved, senses and measures the external environment to the preservation system, senses and measures the internal environment to the preservation system, senses and measures the state of the nutritional substance, and stores such information throughout the period of preservation. Using this accumulated information, the preservation system can measure, or estimate, changes in nutritional content (usually degradation) during the period of preservation. Additionally, the preservation system can use this information to dynamically modify the preservation system to minimize detrimental changes to the nutritional content of the nutritional substance, and in some cases actually improve the nutritional substance attributes.

4 Claims, 14 Drawing Sheets

Frozen Nutritional Substance ΔN

Related U.S. Application Data

(60) Provisional application No. 61/624,948, filed on Apr. 16, 2012, provisional application No. 61/624,972, filed on Apr. 16, 2012, provisional application No. 61/624,985, filed on Apr. 16, 2012.

(51) Int. Cl.

| | | |
|---|---|---|
| G06F 17/30 | (2006.01) | |
| A23B 7/055 | (2006.01) | |
| A23B 4/09 | (2006.01) | |
| A23B 5/055 | (2006.01) | |
| A23B 9/10 | (2006.01) | |
| G06Q 30/06 | (2012.01) | |
| A23L 3/00 | (2006.01) | |
| G01M 3/00 | (2006.01) | |
| G01N 7/00 | (2006.01) | |
| G01N 21/00 | (2006.01) | |
| G01N 25/00 | (2006.01) | |
| G01N 29/00 | (2006.01) | |
| G01N 33/00 | (2006.01) | |
| G05B 15/02 | (2006.01) | |

(52) U.S. Cl.
CPC ............... *A23B 9/10* (2013.01); *A23L 3/001* (2013.01); *A23L 3/375* (2013.01); *G01M 3/00* (2013.01); *G01N 7/00* (2013.01); *G01N 21/00* (2013.01); *G01N 25/00* (2013.01); *G01N 29/00* (2013.01); *G01N 33/0004* (2013.01); *G05B 15/02* (2013.01); *G06F 17/30386* (2013.01); *G06Q 30/06* (2013.01)

(58) Field of Classification Search
USPC ... 426/524, 231–233, 87–88, 394, 383, 393; 434/127
See application file for complete search history.

(56) References Cited

U.S. PATENT DOCUMENTS

| | | |
|---|---|---|
| 4,364,234 A | 12/1982 | Reed |
| 4,555,930 A | 12/1985 | Leach et al. |
| 4,644,137 A | 2/1987 | Asahi et al. |
| 4,644,154 A | 2/1987 | Brogardh et al. |
| 4,650,766 A | 3/1987 | Harm et al. |
| 4,674,320 A | 6/1987 | Hirschfeld |
| 4,777,599 A | 10/1988 | Dorogi et al. |
| 4,837,035 A | 6/1989 | Baker et al. |
| 4,874,928 A | 10/1989 | Kasai |
| 4,914,277 A | 4/1990 | Guerin et al. |
| D308,527 S | 6/1990 | Dallman |
| 5,034,242 A | 7/1991 | Lasdon et al. |
| 5,062,066 A | 10/1991 | Scher et al. |
| D333,782 S | 3/1993 | van Berlo |
| 5,250,789 A | 10/1993 | Johnsen |
| 5,361,681 A | 11/1994 | Hedström |
| 5,412,560 A | 5/1995 | Dennision |
| 5,442,669 A | 8/1995 | Medin |
| 5,478,900 A | 12/1995 | Amano et al. |
| 5,478,989 A | 12/1995 | Shepley |
| 5,478,990 A * | 12/1995 | Montanari et al. ........... 235/375 |
| 5,483,799 A | 1/1996 | Dalto |
| 5,496,576 A | 3/1996 | Jeong |
| 5,558,797 A | 9/1996 | Takagi |
| 5,673,691 A | 10/1997 | Abrams et al. |
| 5,697,177 A | 12/1997 | Ludlow et al. |
| 5,804,803 A | 9/1998 | Cragun et al. |
| 5,853,790 A | 12/1998 | Glancy |
| 5,872,721 A | 2/1999 | Huston et al. |
| 5,877,477 A | 3/1999 | Petty et al. |
| 5,954,640 A | 9/1999 | Szabo |
| 6,012,415 A | 1/2000 | Linseth |
| 6,080,972 A | 6/2000 | May |
| 6,119,531 A | 9/2000 | Wendte et al. |
| 6,157,306 A | 12/2000 | Mularoni |
| 6,182,725 B1 | 2/2001 | Sorvik |
| 6,211,789 B1 | 4/2001 | Oldham et al. |
| 6,270,724 B1 * | 8/2001 | Woodaman ................... 422/416 |
| 6,276,264 B1 | 8/2001 | Dumm |
| 6,285,282 B1 | 9/2001 | Dorenbosch et al. |
| 6,299,920 B1 | 10/2001 | Saksena |
| 6,299,921 B1 | 10/2001 | Loffler et al. |
| 6,310,964 B1 | 10/2001 | Mohan et al. |
| 6,325,878 B1 | 12/2001 | Borgstrom |
| 6,356,940 B1 | 3/2002 | Short |
| 6,375,077 B1 | 4/2002 | Hankins |
| 6,387,049 B1 | 5/2002 | Moore |
| 6,444,233 B1 | 9/2002 | Arntzen et al. |
| 6,483,434 B1 | 11/2002 | Umiker |
| 6,491,217 B2 | 12/2002 | Catan |
| D468,755 S | 1/2003 | Muniz-Rivera et al. |
| 6,502,411 B2 | 1/2003 | Okamoto |
| 6,512,919 B2 | 1/2003 | Ogasawara |
| 6,513,532 B2 | 2/2003 | Mault et al. |
| 6,538,215 B2 | 3/2003 | Montagnino et al. |
| 6,549,818 B1 | 4/2003 | Ali |
| 6,553,386 B1 | 4/2003 | Alabaster |
| 6,554,182 B1 | 4/2003 | Magnusson et al. |
| 6,556,963 B1 | 4/2003 | Tetzlaff |
| 6,571,603 B1 | 6/2003 | Doleman et al. |
| D478,773 S | 8/2003 | Palen |
| 6,616,047 B2 | 9/2003 | Catan |
| 6,631,333 B1 | 10/2003 | Lewis et al. |
| 6,671,698 B2 | 12/2003 | Pickett et al. |
| 6,676,014 B2 | 1/2004 | Catan |
| 6,689,398 B2 | 2/2004 | Haridas et al. |
| 6,691,135 B2 | 2/2004 | Pickett et al. |
| 6,716,462 B2 | 4/2004 | Prosise et al. |
| 6,759,635 B2 | 7/2004 | Lile |
| 6,773,926 B1 | 8/2004 | Freund et al. |
| 6,789,021 B2 | 9/2004 | Rendahl et al. |
| 6,809,301 B1 | 10/2004 | McIntyre et al. |
| 6,844,197 B1 | 1/2005 | Doleman et al. |
| 6,850,861 B1 | 2/2005 | Faiola et al. |
| 6,874,000 B2 | 3/2005 | Sholl et al. |
| 6,888,458 B2 | 5/2005 | Carlson |
| 6,953,342 B2 | 10/2005 | Bisogno |
| 6,953,919 B2 | 10/2005 | Clothier |
| 6,975,910 B1 | 12/2005 | Brown et al. |
| 6,982,640 B2 | 1/2006 | Lindsay et al. |
| 7,024,369 B1 | 4/2006 | Brown et al. |
| 7,076,438 B1 | 7/2006 | Tobelmann et al. |
| 7,080,593 B1 | 7/2006 | Frankel |
| 7,085,777 B2 | 8/2006 | Beck et al. |
| 7,090,638 B2 | 8/2006 | Vidgen |
| 7,103,481 B2 | 9/2006 | Negri |
| 7,151,447 B1 | 12/2006 | Willms et al. |
| 7,152,040 B1 | 12/2006 | Hawthorne et al. |
| D534,758 S | 1/2007 | Lee et al. |
| D539,072 S | 3/2007 | Kawata et al. |
| D539,595 S | 4/2007 | Okuda et al. |
| D540,613 S | 4/2007 | Jeon |
| D540,831 S | 4/2007 | Kim et al. |
| D541,578 S | 5/2007 | Jeon |
| 7,212,955 B2 | 5/2007 | Kirshenbaum et al. |
| 7,213,743 B2 | 5/2007 | Carlson et al. |
| 7,215,420 B2 | 5/2007 | Gellerman et al. |
| 7,237,400 B2 * | 7/2007 | Owada ............................. 62/264 |
| 7,256,699 B2 | 8/2007 | Tethrake et al. |
| 7,275,863 B1 | 10/2007 | Akers et al. |
| 7,295,889 B2 | 11/2007 | Lahteenmaki |
| D560,960 S | 2/2008 | Hillmann et al. |
| 7,326,888 B2 | 2/2008 | Chun et al. |
| 7,349,857 B2 | 3/2008 | Manzo |
| D567,828 S | 4/2008 | Moran |
| 7,357,316 B2 | 4/2008 | Heckel et al. |
| 7,359,802 B1 | 4/2008 | Lewis et al. |
| 7,372,003 B2 | 5/2008 | Kates |
| 7,396,550 B2 | 7/2008 | Angel |
| 7,403,855 B2 | 7/2008 | Fuessley et al. |
| 7,440,901 B1 | 10/2008 | Dlott et al. |
| 7,445,372 B1 | 11/2008 | Engel et al. |

(56) References Cited

U.S. PATENT DOCUMENTS

| | | | |
|---|---|---|---|
| 7,474,965 B2 | 1/2009 | Johnson et al. | |
| 7,509,839 B2 | 3/2009 | Duranton | |
| 7,532,106 B2 | 5/2009 | Debord et al. | |
| 7,571,676 B2 | 8/2009 | Nelson et al. | |
| 7,620,531 B1* | 11/2009 | Johnson | 703/2 |
| D607,264 S | 1/2010 | Lee | |
| 7,681,383 B2 | 3/2010 | Argetsinger et al. | |
| D618,488 S | 6/2010 | Knochner | |
| 7,743,591 B2 | 6/2010 | Meier et al. | |
| 7,797,204 B2 | 9/2010 | Balent | |
| 7,809,601 B2 | 10/2010 | Shaya et al. | |
| 7,836,876 B2 | 11/2010 | Schellenberg | |
| 7,840,359 B2 | 11/2010 | Hsiung et al. | |
| 7,854,108 B2 | 12/2010 | Koselka et al. | |
| D633,326 S | 3/2011 | Shin et al. | |
| 7,933,733 B2 | 4/2011 | Ashrafzadeh et al. | |
| 7,942,867 B2 | 5/2011 | Hood et al. | |
| 7,951,079 B1 | 5/2011 | Moore | |
| 7,957,850 B2 | 6/2011 | Anderson | |
| 7,996,134 B2 | 8/2011 | Roberts | |
| 8,009,048 B2 | 8/2011 | Hyde et al. | |
| 8,033,237 B2 | 10/2011 | Havens et al. | |
| 8,082,809 B2 | 12/2011 | Luellen et al. | |
| D654,299 S | 2/2012 | Benold | |
| 8,112,303 B2 | 2/2012 | Eglen et al. | |
| D657,607 S | 4/2012 | Ohmae et al. | |
| 8,147,888 B2 | 4/2012 | Kling et al. | |
| 8,173,188 B2 | 5/2012 | Suetsugu | |
| D662,525 S | 6/2012 | Moseley | |
| 8,193,474 B2 | 6/2012 | Harris | |
| D665,220 S | 8/2012 | Ohmae et al. | |
| 8,265,957 B2 | 9/2012 | Craine | |
| 8,285,593 B2 | 10/2012 | Bhatt et al. | |
| 8,314,701 B2 | 11/2012 | Grieco et al. | |
| D673,001 S | 12/2012 | Becze et al. | |
| 8,393,137 B1 | 3/2013 | Crosby | |
| 8,403,215 B2 | 3/2013 | Aihara et al. | |
| 8,490,862 B1 | 7/2013 | Minvielle | |
| 8,550,365 B1 | 10/2013 | Minvielle | |
| 8,626,796 B2 | 1/2014 | McBride et al. | |
| 8,631,050 B1 | 1/2014 | Gayle | |
| 8,668,140 B2 | 3/2014 | Minvielle | |
| D702,482 S | 4/2014 | Davis et al. | |
| 8,733,631 B2 | 5/2014 | Minvielle | |
| 8,783,556 B2 | 7/2014 | Minvielle | |
| 8,788,341 B1 | 7/2014 | Patel | |
| 8,796,510 B2 | 8/2014 | Heard et al. | |
| 8,825,516 B2* | 9/2014 | Grant | G06Q 10/08 235/385 |
| 8,851,365 B2 | 10/2014 | Minvielle | |
| 8,864,042 B2 | 10/2014 | Brock et al. | |
| 9,016,193 B2 | 4/2015 | Minvielle | |
| 9,080,997 B2 | 7/2015 | Minvielle | |
| 9,084,566 B2 | 7/2015 | Zdeblick | |
| 9,165,320 B1 | 10/2015 | Belvin | |
| 9,241,909 B2 | 1/2016 | Selanikio | |
| 2002/0004749 A1 | 1/2002 | Froseth et al. | |
| 2002/0005412 A1 | 1/2002 | Laforcade | |
| 2002/0011567 A1 | 1/2002 | Ozanich | |
| 2002/0040564 A1 | 4/2002 | Killingbeck et al. | |
| 2002/0059175 A1 | 5/2002 | Nakano | |
| 2002/0085164 A1 | 7/2002 | Stanford-Clark | |
| 2002/0091593 A1 | 7/2002 | Fowler | |
| 2002/0106432 A1 | 8/2002 | Yamagata et al. | |
| 2002/0123070 A1 | 9/2002 | Hsieh | |
| 2002/0125313 A1 | 9/2002 | Broff | |
| 2002/0163436 A1* | 11/2002 | Singh | A23G 9/00 340/584 |
| 2002/0168456 A1 | 11/2002 | Robbins | |
| 2003/0006281 A1 | 1/2003 | Thomas et al. | |
| 2003/0027161 A1 | 2/2003 | Bejanin et al. | |
| 2003/0050730 A1 | 3/2003 | Greeven et al. | |
| 2003/0099157 A1 | 5/2003 | Quine | |
| 2003/0127451 A1 | 7/2003 | Lile | |
| 2003/0136960 A1 | 7/2003 | Goodman et al. | |
| 2003/0163354 A1 | 8/2003 | Shamoun | |
| 2003/0165602 A1 | 9/2003 | Garwood | |
| 2003/0185937 A1 | 10/2003 | Garwood | |
| 2003/0185948 A1 | 10/2003 | Garwood | |
| 2003/0204359 A1 | 10/2003 | Blakley et al. | |
| 2003/0227392 A1 | 12/2003 | Ebert et al. | |
| 2004/0016348 A1 | 1/2004 | Sharpe | |
| 2004/0045202 A1 | 3/2004 | Arrendale, III et al. | |
| 2004/0083201 A1 | 4/2004 | Sholl et al. | |
| 2004/0093274 A1 | 5/2004 | Vanska et al. | |
| 2004/0100380 A1* | 5/2004 | Lindsay et al. | 340/540 |
| 2004/0130714 A1 | 7/2004 | Gellerman et al. | |
| 2004/0147038 A1 | 7/2004 | Lewis et al. | |
| 2004/0148117 A1 | 7/2004 | Kirshenbaum et al. | |
| 2004/0152131 A1 | 8/2004 | Hsieh | |
| 2004/0158447 A1 | 8/2004 | Leger et al. | |
| 2004/0167724 A1 | 8/2004 | Federer et al. | |
| 2004/0177011 A1 | 9/2004 | Ramsay et al. | |
| 2004/0191382 A1 | 9/2004 | Cooper et al. | |
| 2004/0201454 A1 | 10/2004 | Waterhouse et al. | |
| 2004/0215402 A1 | 10/2004 | Hsiung et al. | |
| 2004/0261280 A1 | 12/2004 | Znaiden et al. | |
| 2004/0267098 A1 | 12/2004 | Moore | |
| 2005/0001728 A1 | 1/2005 | Appelt et al. | |
| 2005/0012627 A1 | 1/2005 | Lion et al. | |
| 2005/0027726 A1 | 2/2005 | Guivarch et al. | |
| 2005/0049920 A1 | 3/2005 | Day et al. | |
| 2005/0075900 A1* | 4/2005 | Arguimbau, III | 705/1 |
| 2005/0079491 A1 | 4/2005 | Donne-Gousse et al. | |
| 2005/0106103 A1 | 5/2005 | Dussaud et al. | |
| 2005/0168325 A1 | 8/2005 | Lievre et al. | |
| 2005/0171738 A1 | 8/2005 | Kadaba | |
| 2005/0184148 A1 | 8/2005 | Perlman | |
| 2005/0247213 A1 | 11/2005 | Slilaty | |
| 2005/0248455 A1 | 11/2005 | Pope et al. | |
| 2005/0251449 A1 | 11/2005 | Pape et al. | |
| 2006/0015371 A1 | 1/2006 | Knauf et al. | |
| 2006/0048588 A1 | 3/2006 | Howarth et al. | |
| 2006/0061454 A1* | 3/2006 | Debord et al. | 340/309.16 |
| 2006/0062835 A1 | 3/2006 | Weil | |
| 2006/0073483 A1 | 4/2006 | White et al. | |
| 2006/0078658 A1 | 4/2006 | Owens et al. | |
| 2006/0099310 A1 | 5/2006 | Koekkoek | |
| 2006/0130498 A1 | 6/2006 | Joshi et al. | |
| 2006/0172048 A1 | 8/2006 | Etchells et al. | |
| 2006/0178841 A1 | 8/2006 | Fernandez | |
| 2006/0200480 A1 | 9/2006 | Harris et al. | |
| 2006/0201432 A1 | 9/2006 | Pratt | |
| 2006/0218057 A1 | 9/2006 | Fitzpatrick et al. | |
| 2006/0228428 A1 | 10/2006 | Kang et al. | |
| 2006/0240174 A1 | 10/2006 | Jung et al. | |
| 2006/0256132 A1 | 11/2006 | Shin et al. | |
| 2006/0277064 A1 | 12/2006 | Cannata | |
| 2006/0286211 A1* | 12/2006 | Lang | 426/88 |
| 2007/0016852 A1 | 1/2007 | Kim et al. | |
| 2007/0036840 A1 | 2/2007 | Tuduri et al. | |
| 2007/0049910 A1 | 3/2007 | Altshuler et al. | |
| 2007/0055551 A1 | 3/2007 | Szabo | |
| 2007/0055573 A1* | 3/2007 | Grell | 705/24 |
| 2007/0059402 A1* | 3/2007 | Barmore | 426/87 |
| 2007/0118394 A1 | 5/2007 | Cahoon | |
| 2007/0191689 A1 | 8/2007 | Elitok | |
| 2007/0204691 A1* | 9/2007 | Bogner | A61B 5/0002 73/432.1 |
| 2007/0207242 A1* | 9/2007 | Carlsen | A22B 5/007 426/231 |
| 2007/0209656 A1 | 9/2007 | Lee | |
| 2007/0254080 A1 | 11/2007 | Schackmuith et al. | |
| 2007/0258048 A1 | 11/2007 | Pitchers | |
| 2007/0269557 A1 | 11/2007 | Culver et al. | |
| 2007/0294129 A1 | 12/2007 | Froseth et al. | |
| 2007/0298147 A1* | 12/2007 | Haus | 426/87 |
| 2008/0058783 A1 | 3/2008 | Altshuler et al. | |
| 2008/0059342 A1* | 3/2008 | Culver | G06F 19/3475 705/28 |
| 2008/0077455 A1 | 3/2008 | Gilboa | |
| 2008/0083825 A1 | 4/2008 | Yang et al. | |
| 2008/0091705 A1 | 4/2008 | McBride et al. | |
| 2008/0102175 A1 | 5/2008 | Jeon et al. | |

(56) References Cited

U.S. PATENT DOCUMENTS

| | | |
|---|---|---|
| 2008/0158543 A1 | 7/2008 | Puskas et al. |
| 2008/0162186 A1 | 7/2008 | Jones |
| 2008/0171120 A1 | 7/2008 | Willett |
| 2008/0186175 A1 | 8/2008 | Stern |
| 2008/0193614 A1 | 8/2008 | Greiner et al. |
| 2008/0195456 A1 | 8/2008 | Fitzpatrick et al. |
| 2008/0254449 A1 | 10/2008 | Plante |
| 2008/0275309 A1 | 11/2008 | Stivoric et al. |
| 2008/0280000 A1 | 11/2008 | Breunig et al. |
| 2008/0295702 A1 | 12/2008 | Wiedemann et al. |
| 2009/0029014 A1* | 1/2009 | Walter ................... G06Q 10/06 426/112 |
| 2009/0035392 A1 | 2/2009 | Wilkinson |
| 2009/0065570 A1 | 3/2009 | Peters et al. |
| 2009/0070040 A1 | 3/2009 | Rabinovitch et al. |
| 2009/0099873 A1 | 4/2009 | Kurple |
| 2009/0157460 A1 | 6/2009 | Narayanaswamy |
| 2009/0177068 A1 | 7/2009 | Stivoric et al. |
| 2009/0202700 A1 | 8/2009 | Bunke et al. |
| 2009/0208607 A1 | 8/2009 | Bunke et al. |
| 2009/0210102 A1* | 8/2009 | Thybo ................... F25D 21/006 700/299 |
| 2009/0232958 A1 | 9/2009 | Samoto et al. |
| 2009/0275002 A1 | 11/2009 | Hoggle |
| 2009/0276912 A1 | 11/2009 | Sherman et al. |
| 2009/0278685 A1 | 11/2009 | Potyrailo et al. |
| 2009/0282004 A1 | 11/2009 | Williams |
| 2009/0283517 A1 | 11/2009 | Mackay et al. |
| 2009/0286212 A1 | 11/2009 | Gordon |
| 2009/0288606 A1 | 11/2009 | Zimmerman |
| 2010/0015313 A1 | 1/2010 | Harris |
| 2010/0055259 A1 | 3/2010 | Bourg, Jr. |
| 2010/0055653 A1* | 3/2010 | Miller-Kovach et al. .... 434/127 |
| 2010/0075436 A1 | 3/2010 | Urdea et al. |
| 2010/0076585 A1 | 3/2010 | Mayer et al. |
| 2010/0076942 A1 | 3/2010 | Lee |
| 2010/0086655 A1* | 4/2010 | Singer ................... G01N 33/02 426/232 |
| 2010/0097193 A1 | 4/2010 | Tang |
| 2010/0102959 A1* | 4/2010 | Ashrafzadeh ........ G06Q 10/087 340/540 |
| 2010/0106625 A1 | 4/2010 | McCoy |
| 2010/0106626 A1 | 4/2010 | Ashrafzadeh et al. |
| 2010/0117819 A1 | 5/2010 | Murray |
| 2010/0119659 A1 | 5/2010 | Ovadia et al. |
| 2010/0125419 A1 | 5/2010 | Hyde et al. |
| 2010/0135211 A1 | 6/2010 | Park et al. |
| 2010/0152687 A1 | 6/2010 | Carlozzi |
| 2010/0175886 A1 | 7/2010 | Bohacs et al. |
| 2010/0185064 A1 | 7/2010 | Bandic et al. |
| 2010/0198605 A1 | 8/2010 | Saulet |
| 2010/0213187 A1 | 8/2010 | Bandholz et al. |
| 2010/0216098 A1 | 8/2010 | Montgomery |
| 2010/0216136 A1 | 8/2010 | B.Che Man et al. |
| 2010/0218044 A1 | 8/2010 | Roblett et al. |
| 2010/0222938 A1 | 9/2010 | Weng |
| 2010/0228160 A1 | 9/2010 | Schweizer |
| 2010/0250271 A1 | 9/2010 | Pearce et al. |
| 2010/0253519 A1 | 10/2010 | Brackmann et al. |
| 2010/0264205 A1 | 10/2010 | Iida |
| 2010/0268658 A1 | 10/2010 | Medo et al. |
| 2010/0280895 A1 | 11/2010 | Mottola |
| 2010/0281636 A1 | 11/2010 | Ortins et al. |
| 2010/0287057 A1* | 11/2010 | Aihara ................ G06K 7/1095 705/16 |
| 2010/0287101 A1 | 11/2010 | Ishikawa et al. |
| 2011/0020785 A1 | 1/2011 | Lowery, Jr. et al. |
| 2011/0029364 A1 | 2/2011 | Roeding et al. |
| 2011/0082711 A1 | 4/2011 | Poeze et al. |
| 2011/0124096 A1 | 5/2011 | Philipak et al. |
| 2011/0153364 A1 | 6/2011 | Kerr et al. |
| 2011/0197827 A1 | 8/2011 | Chang |
| 2011/0204137 A1* | 8/2011 | Scharfenort et al. ......... 235/375 |
| 2011/0217205 A1 | 9/2011 | Peeters |
| 2011/0236862 A1 | 9/2011 | Culver et al. |
| 2011/0240730 A1 | 10/2011 | Covely |
| 2011/0257496 A1 | 10/2011 | Terashima et al. |
| 2011/0258130 A1 | 10/2011 | Grabiner et al. |
| 2011/0259953 A1 | 10/2011 | Baarman et al. |
| 2011/0259960 A1 | 10/2011 | Baarman et al. |
| 2011/0301441 A1 | 12/2011 | Bandic et al. |
| 2011/0302050 A1 | 12/2011 | Kildevaeld |
| 2011/0318717 A1 | 12/2011 | Adamowicz |
| 2012/0004935 A1 | 1/2012 | Winkler |
| 2012/0005105 A1 | 1/2012 | Beier et al. |
| 2012/0005222 A1 | 1/2012 | Bhagwan et al. |
| 2012/0009550 A1 | 1/2012 | Gayle |
| 2012/0016814 A1 | 1/2012 | Evans |
| 2012/0027897 A1 | 2/2012 | Innocenzi |
| 2012/0045540 A1 | 2/2012 | Lee |
| 2012/0052162 A1 | 3/2012 | Goulart |
| 2012/0055718 A1 | 3/2012 | Chen |
| 2012/0083669 A1 | 4/2012 | Abujbara |
| 2012/0085828 A1 | 4/2012 | Ziegler |
| 2012/0085829 A1 | 4/2012 | Ziegler |
| 2012/0097050 A1 | 4/2012 | Schaefer et al. |
| 2012/0105424 A1 | 5/2012 | Lee et al. |
| 2012/0135455 A1 | 5/2012 | Nerin De La Puerta et al. |
| 2012/0152406 A1 | 6/2012 | Bartholomew et al. |
| 2012/0169469 A1 | 7/2012 | Butler et al. |
| 2012/0173269 A1 | 7/2012 | Omidi |
| 2012/0179665 A1 | 7/2012 | Baarman et al. |
| 2012/0189745 A1 | 7/2012 | DeLong |
| 2012/0199643 A1 | 8/2012 | Minnick et al. |
| 2012/0203572 A1 | 8/2012 | Christensen |
| 2012/0216911 A1 | 8/2012 | Bartholomew et al. |
| 2012/0251663 A1 | 10/2012 | Prins et al. |
| 2012/0274470 A1* | 11/2012 | Sandvick ..................... 340/584 |
| 2012/0290051 A1 | 11/2012 | Boyden et al. |
| 2012/0315609 A1 | 12/2012 | Miller-Kovach et al. |
| 2012/0321759 A1 | 12/2012 | Marinkovich et al. |
| 2013/0033031 A1 | 2/2013 | Key |
| 2013/0048736 A1 | 2/2013 | Wien |
| 2013/0048737 A1 | 2/2013 | Baym et al. |
| 2013/0052616 A1 | 2/2013 | Silverstein et al. |
| 2013/0080098 A1 | 3/2013 | Hadad et al. |
| 2013/0080784 A1 | 3/2013 | Oertli |
| 2013/0105470 A1 | 5/2013 | De Luca et al. |
| 2013/0105565 A1 | 5/2013 | Kamprath |
| 2013/0117310 A1 | 5/2013 | Chai et al. |
| 2013/0209615 A1* | 8/2013 | Lee et al. ......................... 426/88 |
| 2013/0231711 A1 | 9/2013 | Kaib |
| 2013/0255507 A1 | 10/2013 | Meunier et al. |
| 2013/0269297 A1 | 10/2013 | Minvielle |
| 2013/0269454 A1 | 10/2013 | Minvielle |
| 2013/0269537 A1 | 10/2013 | Minvielle |
| 2013/0269538 A1 | 10/2013 | Minvielle |
| 2013/0269542 A1 | 10/2013 | Minvielle |
| 2013/0269543 A1 | 10/2013 | Minvielle |
| 2013/0269544 A1 | 10/2013 | Minvielle |
| 2013/0270337 A1 | 10/2013 | Minvielle |
| 2013/0273217 A1 | 10/2013 | Minvielle |
| 2013/0273507 A1 | 10/2013 | Minvielle |
| 2013/0273509 A1 | 10/2013 | Mutti |
| 2013/0275037 A1 | 10/2013 | Minvielle |
| 2013/0275318 A1 | 10/2013 | Minvielle |
| 2013/0275342 A1 | 10/2013 | Minvielle |
| 2013/0275343 A1 | 10/2013 | Minvielle |
| 2013/0275370 A1 | 10/2013 | Minvielle |
| 2013/0275426 A1 | 10/2013 | Minvielle |
| 2013/0275439 A1 | 10/2013 | Minvielle |
| 2013/0275460 A1 | 10/2013 | Minvielle |
| 2013/0275477 A1 | 10/2013 | Minvielle |
| 2013/0276644 A1 | 10/2013 | Minvielle |
| 2013/0287060 A1 | 10/2013 | Langdoc et al. |
| 2013/0290364 A1 | 10/2013 | Minvielle |
| 2013/0295532 A1 | 11/2013 | Minvielle |
| 2013/0297642 A1 | 11/2013 | Minvielle |
| 2013/0302483 A1 | 11/2013 | Riefenstein |
| 2013/0309138 A1 | 11/2013 | Minvielle |
| 2013/0309636 A1 | 11/2013 | Minvielle |
| 2013/0309637 A1 | 11/2013 | Minvielle |
| 2013/0310955 A1 | 11/2013 | Minvielle |

(56) References Cited

U.S. PATENT DOCUMENTS

| | | |
|---|---|---|
| 2013/0337516 A1 | 12/2013 | Herrema |
| 2014/0018636 A1 | 1/2014 | Contant et al. |
| 2014/0026762 A1 | 1/2014 | Riefenstein |
| 2014/0037805 A1 | 2/2014 | Minvielle |
| 2014/0038140 A1 | 2/2014 | Minvielle |
| 2014/0041532 A1 | 2/2014 | Minvielle |
| 2014/0041533 A1 | 2/2014 | Minvielle |
| 2014/0061296 A1 | 3/2014 | Minvielle |
| 2014/0069838 A1 | 3/2014 | Minvielle |
| 2014/0091136 A1 | 4/2014 | Ybarra, Jr. |
| 2014/0191025 A1 | 7/2014 | Minvielle |
| 2014/0214714 A1 | 7/2014 | Minvielle |
| 2014/0236359 A1 | 8/2014 | Minvielle |
| 2014/0263640 A1 | 9/2014 | Heit et al. |
| 2014/0279088 A1 | 9/2014 | Hurst et al. |
| 2014/0290395 A1 | 10/2014 | Minvielle |
| 2014/0290396 A1 | 10/2014 | Minvielle |
| 2014/0339296 A1 | 11/2014 | McAdams et al. |
| 2014/0364971 A1 | 12/2014 | Minvielle |
| 2014/0364972 A1 | 12/2014 | Minvielle |
| 2015/0012122 A1 | 1/2015 | Minvielle |
| 2015/0017252 A1 | 1/2015 | Garland et al. |
| 2015/0037764 A1 | 2/2015 | Minvielle |
| 2015/0051841 A1 | 2/2015 | Minvielle |
| 2015/0057773 A1 | 2/2015 | Minvielle |
| 2015/0100350 A1 | 4/2015 | Minvielle |
| 2015/0100462 A1 | 4/2015 | Minvielle |
| 2015/0149120 A1 | 5/2015 | Burkhardt et al. |
| 2015/0227887 A1 | 8/2015 | Minvielle |
| 2015/0235566 A1 | 8/2015 | Minvielle |
| 2015/0236913 A1 | 8/2015 | Nakano et al. |
| 2015/0320808 A1 | 11/2015 | Burcelin et al. |
| 2016/0260352 A1 | 9/2016 | Ortiz |

FOREIGN PATENT DOCUMENTS

| | | |
|---|---|---|
| DE | 19843016 A1 | 3/2000 |
| DE | 10 2005 040206 A1 | 2/2007 |
| DE | 10 2007 032 303 A1 | 1/2008 |
| EP | 1117055 A2 | 7/2001 |
| EP | 1 253 203 A1 | 10/2002 |
| FR | 2813683 A1 | 3/2002 |
| GB | 2312054 A | 10/1997 |
| WO | 91/13304 A1 | 9/1991 |
| WO | WO 02/06984 | 1/2002 |
| WO | 02/37375 A1 | 5/2002 |
| WO | WO 2007/108906 A2 | 9/2007 |
| WO | WO 2008/054231 A1 | 5/2008 |
| WO | 2009/157750 | 12/2009 |
| WO | WO 2013/126579 A1 | 8/2013 |
| WO | 2013/134325 A1 | 9/2013 |
| WO | WO 2013/134544 A1 | 9/2013 |
| WO | WO 2013/142218 A1 | 9/2013 |
| WO | 2013/158571 A2 | 10/2013 |
| WO | 2013/158572 A2 | 10/2013 |
| WO | 2013/158576 A1 | 10/2013 |
| WO | 2013/176800 A1 | 11/2013 |
| WO | WO 2013/180925 A2 | 12/2013 |
| WO | 2014/168844 A2 | 10/2014 |
| WO | WO 2014/182566 A2 | 11/2014 |
| WO | WO 2014/210531 A2 | 12/2014 |
| WO | WO 2015/006351 A1 | 1/2015 |
| WO | WO 2015/013030 A1 | 1/2015 |
| WO | WO 2015/013031 A2 | 1/2015 |
| WO | 2015/054082 | 4/2015 |
| WO | WO 2015/069325 A1 | 5/2015 |
| WO | WO 2015/069950 A1 | 5/2015 |
| WO | WO 2015/073569 A1 | 5/2015 |

OTHER PUBLICATIONS

Advisory Action in U.S. Appl. No. 13/485,878, mailed Sep. 16, 2014.
Office Action in U.S. Appl. No. 13/888,353, mailed Oct. 1, 2014.
PCT International Search Report and Written Opinion in International Application No. PCT/US2014/044696, mailed Oct. 10, 2014.
PCT International Search Report and Written Opinion in International Application No. PCT/US2014/045796, mailed Oct. 15, 2014.
PCT International Search Report and Written Opinion in International Application No. PCT/US2014/045798, mailed Oct. 15, 2014.
Montesinos, F., "Plant-associated Microorganisms: a View from the Scope of Microbiology", International Microbiology, Dec. 2003, vol. 6, Issue 4, pp. 221-223.
Sinclair, D.A. et al., "Unlocking the Secrets of Longevity Genes", Scientific American, Mar. 2006, vol. 294, Issue 3, pp. 48-57.
Diller, K.R., "Stress Protein Expression Kinetics", Annual Review of Biomedical Engineering, 2006, vol. 8, pp. 403-424.
Zerebecki, R.A. et al., "Temperature Tolerance and Stress Proteins as Mechanisms of Invasive Species Success", PLoS One, Apr. 2011, vol. 6, Issue 4, e14806, pp. 1-7.
Ni, Fu-Tai et al., "Gene Expression and Regulation of Higher Plants Under Soil Water Stress", Current Genomics, Jun. 2009, vol. 10, pp. 269-280.
Hayano-Kanashiro, C. et al., "Analysis of Gene Expression and Physiological Responses in Three Mexican Maize Landraces Under Drought Stress and Recovery Irrigation", PLoS One, Oct. 2009, vol. 4, Issue 10, e7531, pp. 1-19.
Kingsmore, S.F., "Multiplexed Protein Measurement: Technologies and Applications of Protein and Antibody Arrays", Nature Reviews Drug Discovery, Apr. 2006, vol. 5, pp. 310-321.
Kaume, L. et al., "The Blackberry Fruit: A Review on Its Composition and Chemistry, Metabolism and Bioavailability, and Health Benefits", Journal of Agricultural and Food Chemistry, 2012, vol. 60 (23), pp. 5716-5727.
Perks, B., "Fighting Food Fraud with Science", Text Reproduced from Chemistry World, 2007, vol. 4 (9), pp. 48-52.
Montealegre, C. et al., "Traceability Markers to the Botanical Origin in Olive Oils", Journal of Agricultural and Food Chemistry, 2010, vol. 58 (1), pp. 28-38.
Martins-Lopes, P. et al., "DNA Markers for Portuguese Olive Oil Fingerprinting", Journal of Agricultural and Food Chemistry, 2008, vol. 56 (24), pp. 11786-11791.
Garcia-Gonzalez, D.L. et al., "Research in Olive Oil: Challenges for the Near Future", Journal of Agricultural and Food Chemistry, 2010, vol. 58 (24), pp. 12569-12577.
Zou, Ming-Qiang et al., "Rapid Authentication of Olive Oil Adulteration by Raman Spectrometry", Journal of Agricultural and Food Chemistry, 2009, vol. 57 (14), pp. 6001-6006.
Frankel, E.N., "Chemistry of Extra Virgin Olive Oil: Adulteration, Oxidative Stability, and Antioxidants", Journal of Agricultural and Food Chemistry, 2010, vol. 58 (10), pp. 5991-6006.
Lago, Fatima C. et al., "FINS Methodology to Identification of Sardines and Related Species in Canned Products and Detection of Mixture by Means of SNP Analysis Systems", European Food Research and Technology, Jun. 2011, vol. 232(6), pp. 1077-1086.
Lago, Fatima C. et al., "Genetic Identification of Horse Mackerel and Related Species in Seafood Products by Means of Forensically Informative Nucleotide Sequencing Methodology", Journal of Agricultural and Food Chemistry, 2011, vol. 59 (6), pp. 2223-2228.
Suslick, B.A. et al., "Discrimination of Complex Mixtures by a Colorimetric Sensor Array: Coffee Aromas", Analytical Chemistry, Mar. 1, 2010, vol. 82, No. 5, pp. 2067-2073.
Rashidi, L. et al., "The Applications of Nanotechnology in Food Industry", Critical Reviews in Food Science and Nutrition, 2011, vol. 51, Issue 8, pp. 723-730.
Staggers, N. et al., "Nanotechnology: The Coming Revolution and its Implications for Consumers, Clinicians, and Informatics", Nursing Outlook, Sep.-Oct. 2008, vol. 56, No. 5, pp. 268-274.
Chaudhry, Q. et al., "Applications and Implications of Nanotechnologies for the Food Sector", Food Additives and Contaminants: Part A, Mar. 2008, vol. 25, Issue 3, pp. 241-258.
Srinivas, P.R. et al., "Nanotechnology Research: Applications in Nutritional Sciences", The Journal of Nutrition, Symposium-Nanotechnology Research: Applications in Nutritional Sciences, Jan. 2010, vol. 140, No. 1, pp. 119-124.
Walt, D.R., "Electronic Noses: Wake Up and Smell the Coffee", Analytical Chemistry, Feb. 1, 2005, vol. 77 (3), p. A-45.

(56) References Cited

OTHER PUBLICATIONS

Aernecke, M.J. et al., "Optical-fiber Arrays for Vapor Sensing", Sensors and Actuators B: Chemical, Nov. 2009, vol. 142, Issue 2, pp. 464-469.
Anslyn, E.V., "Supramolecular Analytical Chemistry", The Journal of Organic Chemistry, Feb. 2, 2007, vol. 72, No. 3, pp. 687-699.
Lewis, N.S., "Comparisons Between Mammalian and Artificial Olfaction Based on Arrays of Carbon Black-Polymer Composite Vapor Detectors", Accounts of Chemical Research, 2004, vol. 37, No. 9, pp. 663-672.
Rock, F. et al., "Electronic Nose: Current Status and Future Trends", Chemical Reviews, 2008, vol. 108, No. 2, pp. 705-725.
Hierlemann, A. et al., "Higher-Order Chemical Sensing", Chemical Reviews, 2008, vol. 108, No. 2, pp. 563-613.
Hsieh, Meng-Da et al., "Limits of Recognition for Simple Vapor Mixtures Determined with a Microsensor Array", Analytical Chemistry, Apr. 1, 2004, vol. 76, No. 7, pp. 1885-1895.
Grate, J.W., "Acoustic Wave Microsensor Arrays for Vapor Sensing", Chemical Reviews, 2000, vol. 100, No. 7, pp. 2627-2647.
Janata, J. et al., "Conducting Polymers in Electronic Chemical Sensors", Nature Materials, Jan. 2003, vol. 2, pp. 19-24.
Wolfbeis, O.S., "Materials for Fluorescence-based Optical Chemical Sensors", Journal of Materials Chemistry, 2005, vol. 15, pp. 2657-2669.
James, D. et al., "Chemical Sensors for Electronic Nose Systems", Microchimica Acta, Feb. 2005, vol. 149, pp. 1-17.
Primrose, S. et al., "Food Forensics: Methods for Determining the Authenticity of Foodstuffs", Trends in Food Science & Technology, Dec. 2010, vol. 21 (12), pp. 582-590.
Kharif, Olga, "Janne Haverinen: Mapping the Great Indoors", Bloomberg BusinessWeek, May 9, 2012, retrieved from URL: <http://www.businessweek.com/articles/2012-08-09/janne-haverinen-mapping-the-great-indoors on Apr. 12, 2013>.
Cheftel, J. Claude, "Food and Nutrition Labelling in the European Union", Food Chemistry 93.3, Dec. 2005, pp. 531-550, retrieved on Mar. 10, 2013 from URL: <http://www.sciencedirect.com/science/article/pii/S0308814604008581>.
U.S. Office Action in U.S. Appl. No. 13/485,850 mailed on May 9, 2013.
U.S. Office Action in U.S. Appl. No. 13/560,965 mailed on Feb. 1, 2013.
U.S. Office Action in U.S. Appl. No. 13/602,040 mailed on Jan. 11, 2013 (restriction).
U.S. Office Action in U.S. Appl. No. 13/685,575 mailed on May 6, 2013.
U.S. Office Action in U.S. Appl. No. 13/750,804 mailed on Mar. 12, 2013.
U.S. Office Action in U.S. Appl. No. 13/771,004 mailed on May 15, 2013.
Notice of Allowance in U.S. Appl. No. 13/560,965 mailed on Mar. 22, 2013.
Notice of Allowance in U.S. Appl. No. 13/750,804 mailed on May 31, 2013.
PCT International Search Report and Written Opinion in International Application No. PCT/US2013/029686, mailed on May 13, 2013.
PCT International Search Report and Written Opinion in International Application No. PCT/US2013/031106, mailed on May 31, 2013.
PCT International Search Report and Written Opinion in International Application No. PCT/US13/27148, mailed on Jun. 18, 2013.
PCT International Search Report and Written Opinion in International Application No. PCT/US13/29219, mailed on Jun. 20, 2013.
U.S. Office Actions in U.S. Appl. No. 13/771,004 mailed on Jul. 8, 2013.
Thakur, M. et al., "Food Traceability, R&D Norway" Food Technology, Apr. 2012, p. 42-46.
Hoffman, B., "IBM Announces Food Traceability Technology," Food+Tech Connect, Oct. 19, 2011, 2 pages.

"SIRA Technologies Food Sentinel System Thermal Barcode for Packaging," Sustainable is Good: Lifestyle and Design blog, Mar. 4, 2009, 2 pages.
Etherington, Darrell, "iCarte Turns the iPhone Into an RFID Reader," Gigaom, Nov. 18, 2009 (downloaded Oct. 3, 2013, from URL http://gigaom.com/2009/11/18/icarte-turns-the-iphone-into-an-rfid-reader/).
Ghasemi-Varnamkhasti, M. et al., "Biomimetic-based odor and taste sensing systems to food quality and safety characterization: An overview on basic principles and recent achievements", Journal of Food Engineering, vol. 100, pp. 377-387, May 2010.
Greenfield, H. et al., "Food composition data," FAO, 2003 ("FAO").
Preechaburana, Pakorn et al., "Surface Plasmon Resonance Chemical Sensing on Cell Phones", Angewandte Chemie International Edition, vol. 51, Issue 46, pp. 11585-11588, first published online Oct. 16, 2012.
Notice of Allowance in U.S. Appl. No. 13/900,426, mailed Dec. 16, 2013.
Notice of Allowance in U.S. Appl. No. 13/931,744, mailed Feb. 28, 2014.
Notice of Allowance in U.S. Appl. No. 14/047,817, mailed Apr. 14, 2014.
Notice of Allowance in U.S. Appl. No. 14/074,664, mailed Jun. 2, 2014.
Office Action in U.S. Appl. No. 13/485,850, mailed Mar. 20, 2014.
Office Action in U.S. Appl. No. 13/485,850, mailed Sep. 30, 2013.
Office Action in U.S. Appl. No. 13/485,878, mailed Jun. 5, 2014.
Office Action in U.S. Appl. No. 13/485,878, mailed Oct. 24, 2013.
Office Action in U.S. Appl. No. 13/602,040, mailed Jul. 17, 2014.
Office Action in U.S. Appl. No. 13/602,040, mailed Oct. 23, 2013.
Office Action in U.S. Appl. No. 13/685,575, mailed Oct. 24, 2013.
Office Action in U.S. Appl. No. 13/732,050, mailed Apr. 10, 2014.
Office Action in U.S. Appl. No. 13/732,050, mailed Oct. 24, 2013.
Office Action in U.S. Appl. No. 13/771,004, mailed Apr. 4, 2014.
Office Action in U.S. Appl. No. 13/888,353, mailed Dec. 4, 2013 (restriction).
Office Action in U.S. Appl. No. 13/888,353, mailed Jul. 25, 2013 (restriction).
Office Action in U.S. Appl. No. 13/888,353, mailed May 1, 2014.
Office Action in U.S. Appl. No. 13/900,426, mailed Aug. 8, 2013.
Office Action in U.S. Appl. No. 13/931,744, mailed Aug. 20, 2013.
Office Action in U.S. Appl. No. 13/937,167, mailed Apr. 14, 2014.
Office Action in U.S. Appl. No. 13/937,167, mailed Oct. 28, 2013.
Office Action in U.S. Appl. No. 13/948,004, mailed Jun. 11, 2014.
Office Action in U.S. Appl. No. 13/948,004, mailed Oct. 24, 2013.
Office Action in U.S. Appl. No. 14/047,817, mailed Nov. 29, 2013.
Office Action in U.S. Appl. No. 14/059,441 mailed Jul. 10, 2014.
Office Action in U.S. Appl. No. 14/059,441, mailed Dec. 20, 2013.
Office Action in U.S. Appl. No. 14/059,441, mailed Feb. 11, 2014.
Office Action in U.S. Appl. No. 14/074,664, mailed Jan. 8, 2014.
Office Action in U.S. Appl. No. 14/137,963, mailed Aug. 5, 2014.
Restriction Requirement in U.S. Appl. No. 13/684,113, mailed Sep. 5, 2014.
Restriction Requirement in U.S. Appl. No. 14/137,963, mailed May 7, 2014.
Extended European Search Report in European Application No. 13731655.0, dated Feb. 24, 2014.
Extended European Search Report in European Application No. 13757669.0, dated Jan. 31, 2014.
Notice from the European Patent Office, dated Oct. 1, 2007, concerning business methods, Official Journal EPO, pp. 592-593.
PCT International Search Report and Written Opinion in International Application No. PCT/US2013/36666, mailed Oct. 4, 2013.
PCT International Search Report and Written Opinion in International Application No. PCT/US2013/036668, mailed Dec. 6, 2013.
PCT International Search Report and Written Opinion in International Application No. PCT/US2013/036670, mailed Aug. 19, 2013.
PCT International Search Report and Written Opinion in International Application No. PCT/US2013/036673, mailed Aug. 20, 2013.
PCT International Search Report and Written Opinion in International Application No. PCT/US2013/040445, mailed Oct. 25, 2013.
Statement in accordance with the Notice from the European Patent Office, dated Oct. 1, 2007, concerning business methods.

(56) References Cited

OTHER PUBLICATIONS

"Automated Fruit Recognition" Fraunhofer, accessed online Nov. 13, 2014 and, available at http://www.iosb.fraunhofer.de/servlet/is/33328/.
Chung I-C. et al., "A Portable Electrochemical Sensor for Caffeine and (−)Epigallocatechin Gallate Based on Molecularly Imprinted Poly(ethylene-co-vinyl alcohol) Recognition Element", J Nanosci Nanotechnol., vol. 11, No. 12, Dec. 2011, pp. 10633-10638.
"Cool runnings needed for fine wines," AFP, Apr. 28, 2008, retrieved from internet URL http://www.google.com/hostednews/afp/article/ALeqM5hm5gRK3maWqEJppJOBObR71THV on Feb. 10, 2014.
Composition of Foods Raw, Processed, Prepared USDA National Nutrient Database for Standard Reference, Release 26 Documentation and User Guide, U.S. Department of Agriculture Agricultural Research Service, Aug. 2013 (revised Nov. 2013), 136 pages, accessed on its website, at http://www.ars.usda.gov/SP2UserFiles/Place/12354500/Data/SR26/sr26_doc.pdf.
De Vos, K. et al., "Multiplexed antibody detection with an array of silicon-on-insulator microring resonators", IEEE, Photonics Journal, vol. 1, Issue 4, Oct. 2009, pp. 225-235.
Dorokhin, D. et al., "Imaging surface plasmon resonance for multiplex microassay sensing of mycotoxins", Analytical and Bioanalytical Chemistry, vol. 400, Issue 9, published online Apr. 12, 2011, pp. 3005-3011.
Ebarvia, et al, "Biomimetic piezoelectric quartz sensor for caffeine based on a molecularly imprinted polymer", Analytical and Bioanalytical Chemistry, vol. 378, Issue 5, Mar. 2004, published online Jan. 27, 2004, pp. 1331-1337.
Focke, M. et al., "Lab-on-a-Foil: microfluidics on thin and flexible films", Lab on a Chip, vol. 10, Issue 11, published online Mar. 19, 2010, pp. 1365-1386.
Gartia, M. et al., "Colorimetric plasmon resonance imaging using nano lycurgus cup arrays", Advanced Optical Materials, vol. 1, Issue 1, Jan. 2013, pp. 68-76.
Huang, et al., "A passive radio•frequency pH sensing tag for wireless food quality monitoring", IEEE Sensors Journal, vol. 12, Issue 3, pp. 487-495, Mar. 2012.
Kumar, A. et al., "Study of fiber optic sugar sensor", Pramana, vol. 67, Issue 2, Aug. 2006, pp. 383-387.
Kwon, H. et al., "Fluorescent DNAs printed on paper: Sensing food spoilage and ripening in the vapor phase", Chemical Science, vol. 3, Issue 8, published online May 17, 2012, pp. 2542-2549.
Lin, et al., "Multiplex fiber-optic biosensor using multiple particle plasmon resonances", International Society for Optics and Photonics: Third Asia Pacific Optical Sensors Conference, vol. 8351, Sydney, Australia, Jan. 31, 2012, pp. 83512S1-83512S7.
Ricci, F. et al., "A review on novel developments and applications of immunosensors in food analysis", Analytica Chimica Acta, vol. 605, Issue 2, Dec. 19, 2007, pp. 111-129.
Roche, PJR, et al., "A Camera Phone Localised Surface Plasmon Biosensing Platform Towards Low-Cost Label-Free Diagnostic Testing", Journal of Sensors, vol. 2011, 2011, 7 pages.
Scampicchio, M. et al., "Optical nanoprobes based on gold nanoparticles for sugar sensing", Nanotechnology, vol. 20, Issue 13, Apr. 1, 2009, 5 pages.
Zhu, H. et al., "Quantum dot enabled detection of *Escherichia coli* using a cell-phone", Analyst, vol. 137, Issue 11, Jun. 7, 2012, pp. 2541-2544.
Office Action in U.S. Appl. No. 13/685,575, mailed Oct. 27, 2014.
Office Action in U.S. Appl. No. 13/921,078, mailed Nov. 4, 2014.
Office Action in U.S. Appl. No. 13/931,733, mailed Nov. 6, 2014.
Office Action in U.S. Appl. No. 14/306,111, mailed Nov. 13, 2014.
Office Action in U.S. Appl. No. 29/497,888, mailed Nov. 19, 2014.
European Examination Report in European Application No. 13757669.0, dated Oct. 13, 2014.
Bell, S. et al., "Report on nutrient losses and gains factors used in European food composition databases", Technical Report, Apr. 2006, 66 pages (Retrieved from the Internet on Mar. 2, 2015 at: http://www.eurofir.net).

Hugh, J. "Recipe Calculations: Where Do We Stand?", Proceedings of the 12th National Nutrient Databank Conference, Houston, Texas, Apr. 12, 1987, pp. 135-139 (Retrieved from the Internet on Feb. 13, 2015 at http://www.nutrientdataconf.org/PastConf/NDBC12/5-2_Joseph.pdf ).
Valero, C., et al., "Design Guidelines for a Quality Assessment System of Fresh Fruits in Fruit Centers and Hypermarkets", Abstract, Agriculture Engineering International: the CIGR Journal of Scientific Research and Development, vol. II, Aug. 2000, 20 pages. Available online at http://dspace.library.cornell.edu/retrieve/237/, accessed Feb. 19, 2015.
Office Action in U.S. Appl. No. 13/485,850, mailed Mar. 19, 2015.
Office Action in U.S. Appl. No. 13/485,863, mailed Feb. 9, 2015.
Office Action in U.S. Appl. No. 13/485,883, mailed Feb. 3, 2015.
Office Action in U.S. Appl. No. 13/485,900, mailed Feb. 3, 2015.
Office Action in U.S. Appl. No. 13/684,113, mailed Dec. 15, 2014.
Office Action in U.S. Appl. No. 13/771,004, mailed Mar. 10, 2015.
Office Action in U.S. Appl. No. 13/861,300 mailed Feb. 24, 2015.
Office Action in U.S. Appl. No. 13/931,733, mailed Mar. 10, 2015.
Office Action in U.S. Appl. No. 14/044,851, mailed Jan. 5, 2015.
Notice of Allowance in U.S. Appl. No. 14/059,441, mailed Jan. 5, 2015.
Notice of Allowance in U.S. Appl. No. 14/137,963, mailed Jan. 28, 2015.
Office Action in U.S. Appl. No. 14/304,671, mailed Feb. 4, 2015.
Notice of Allowance in U.S. Appl. No. 14/306,111, mailed Mar. 17, 2015.
PCT International Search Report and Written Opinion in International Application No. PCT/US2014/033084, mailed Mar. 6, 2015.
PCT International Search Report and Written Opinion in International Application No. PCT/US2014/036570, mailed Mar. 10, 2015.
PCT International Search Report and Written Opinion in International Application No. PCT/US2014/045807, mailed Jan. 22, 2015.
PCT International Search Report and Written Opinion in International Application No. PCT/US14/59186, mailed Dec. 22, 2014.
PCT International Search Report and Written Opinion in International Application No. PCT/US2014/065281, mailed Mar. 13, 2015.
PCT International Search Report and Written Opinion in International Application No. PCT/US2014/064434, mailed Feb. 20, 2015.
Communication Pursuant to Article 94(3) in European Application No. 13731655.0, dated Jan. 22, 2015.
Extended European Search Report in European Application No. 13751912.0, dated Feb. 25, 2015.
Office Action in U.S. Appl. No. 13/485,866, mailed May 7, 2015.
Office Action in U.S. Appl. No. 13/485,883, mailed May 20, 2015.
Office Action in U.S. Appl. No. 13/485,916, mailed Mar. 27, 2015.
Office Action in U.S. Appl. No. 13/646,632, mailed Mar. 26, 2015.
Office Action in U.S. Appl. No. 13/685,575, mailed May 5, 2015.
Office Action in U.S. Appl. No. 13/888,353, mailed Mar. 26, 2015.
Notice of Allowance in U.S. Appl. No. 13/921,078, mailed Apr. 1, 2015.
Notice of Allowance in U.S. Appl. No. 14/044,851, mailed Mar. 31, 2015.
Office Action in U.S. Appl. No. 14/203,353, mailed Mar. 31, 2015.
Office Action in U.S. Appl. No. 14/260,115, mailed Apr. 16, 2015.
Office Action in U.S. Appl. No. 14/466,805, mailed Apr. 13, 2015.
Office Action in U.S. Appl. No. 14/286,627, mailed Apr. 24, 2015.
Office Action in U.S. Appl. No. 14/466,824, mailed May 7, 2015.
Office Action in U.S. Appl. No. 14/467,433, mailed May 8, 2015.
PCT International Search Report and Written Opinion in International Application No. PCT/US2014/044700, mailed May 18, 2015.
Office Action in U.S. Appl. No. 13/485,850 mailed Sep. 24, 2015.
Office Action in U.S. Appl. No. 13/485,883, mailed Oct. 28, 2015.
Office Action in U.S. Appl. No. 13/485,916, mailed Sep. 18, 2015.
Office Action in U.S. Appl. No. 13/646,632, mailed Oct. 20, 2015.
Office Action in U.S. Appl. No. 13/771,004, mailed Oct. 22, 2015.
Office Action in U.S. Appl. No. 13/861,300 mailed Sep. 29, 2015.
Office Action in U.S. Appl. No. 14/286,627, mailed Oct. 9, 2015.
Office Action in U.S. Appl. No. 14/667,608 mailed Nov. 2, 2015.
Office Action in U.S. Appl. No. 14/725,114 mailed Oct. 22, 2015.
alKanhal et al., "Changes in protein nutritional quality in fresh and recombined ultra high temperature treated milk during storage.", Int. J. Food Sci. Nutr, Nov. 2001; 52(6): 509-14, 2 pgs.

(56) References Cited

OTHER PUBLICATIONS

Office Action in U.S. Appl. No. 13/485,863, mailed Dec. 30, 2015.
Office Action in U.S. Appl. No. 13/485,866, mailed Dec. 24, 2015.
Office Action in U.S. Appl. No. 13/646,632, mailed Dec. 31, 2015.
Office Action in U.S. Appl. No. 13/887,150 mailed Nov. 20, 2015.
Office Action in U.S. Appl. No. 13/948,004, mailed Dec. 17, 2015.
Office Action in U.S. Appl. No. 14/260,115, mailed Dec. 4, 2015.
Office Action in U.S. Appl. No. 14/466,805, mailed Nov. 20, 2015.
Office Action in U.S. Appl. No. 14/467,433, mailed Dec. 24, 2015.
Extended European Search Report in European Application No. 13778362.7, dated Nov. 27, 2015.
Extended European Search Report in European Application No. 13777608.4, dated Nov. 19, 2015.
Extended European Search Report in European Application No. 13778042.5, dated Nov. 20, 2015.
PCT International Search Report and Written Opinion in International Application No. PCT/US2015/045562, mailed Nov. 23, 2015.
Qiao, Y, "Routine Techniques for Monitoring the Value of Animal Meals", Unknown, 2001, 224 pgs. https://books.google.com/books/about/Routine_Techniques_for_Monitoring_the_Nu.html?id=LhsktkRPZ7EC (No Copies Available Online Copyright Restricted).
Wijtzes, T., et al., "A decision support system for the prediction of microbial food safety and food quality", International Journal of Food Microbiology 42 (1997) 79-90.
Office Action in U.S. Appl. No. 13/485,854, mailed Mar. 17, 2016.
Office Action in U.S. Appl. No. 13/485,878, mailed Feb. 1, 2016.
Office Action in U.S. Appl. No. 13/485,883, mailed Apr. 19, 2016.
Office Action in U.S. Appl. No. 13/485,916, mailed Feb. 18, 2016.
Office Action in U.S. Appl. No. 13/602,040, mailed May 6, 2016.
Office Action in U.S. Appl. No. 13/646,632, mailed Apr. 21, 2016.
Office Action in U.S. Appl. No. 13/685,575, mailed May 11, 2016.
Office Action in U.S. Appl. No. 13/684,113, mailed Jun. 8, 2016.
Office Action in U.S. Appl. No. 13/732,050, mailed Jan. 15, 2016.
Office Action in U.S. Appl. No. 13/771,004, mailed May 31, 2016.
Notice of Allowance in U.S. Appl. No. 13/861,300, mailed Apr. 15, 2016.
Office Action in U.S. Appl. No. 13/887,150 mailed Jun. 17, 2016.
Office Action in U.S. Appl. No. 13/888,353, mailed Apr. 21, 2016.
Office Action in U.S. Appl. No. 13/937,167 mailed Mar. 2, 2016.
Office Action in U.S. Appl. No. 13/948,083, mailed Jul. 14, 2016.
Office Action in U.S. Appl. No. 14/080,768, mailed Jan. 25, 2016.
Office Action in U.S. Appl. No. 14/304,671, mailed Apr. 8, 2016.
Office Action in U.S. Appl. No. 14/203,353, mailed Mar. 7, 2016.
Office Action in U.S. Appl. No. 14/203,353, mailed Jul. 29, 2016.
Notice of Allowance in U.S. Appl. No. 14/260,115, mailed Jun. 21, 2016.
Office Action in U.S. Appl. No. 14/466,805, mailed Mar. 8, 2016.
Office Action in U.S. Appl. No. 14/286,627, mailed Mar. 3, 2016.
Notice of Allowance in U.S. Appl. No. 14/286,627, mailed Jun. 22, 2016.
Office Action in U.S. Appl. No. 14/466,824, mailed Jan. 13, 2016.
Notice of Allowance in U.S. Appl. No. 14/467,433, mailed Jul. 5, 2016.
Office Action in U.S. Appl. No. 14/307,365, mailed May 3, 2016.
Office Action in U.S. Appl. No. 14/643,995 mailed Jun. 14, 2016.
Office Action in U.S. Appl. No. 14/667,608 mailed Mar. 16, 2016.
Office Action in U.S. Appl. No. 14/725,114 mailed Jun. 27, 2016.
Office Action in U.S. Appl. No. 14/860,340 mailed Apr. 20, 2016.
Search Report and Written Opinion in Singapore application 10201406107X dated Feb. 11, 2016.
Extended European Search Report in European Application No. 13757527.0, dated Mar. 24, 2016.
Extended European Search Report in European Application No. 13793073.1 dated Jan. 14, 2016.
Office Action in U.S. Appl. No. 13/485,866, mailed Jul. 26, 2016.
Notice of Allowance in U.S. Appl. No. 13/931,733, mailed Jun. 11, 2015.
Office Action in U.S. Appl. No. 13/485,854, mailed Aug. 21, 2015.
Office Action in U.S. Appl. No. 13/485,863, mailed Sep. 2, 2015.
Office Action in U.S. Appl. No. 13/485,878, mailed Jul. 8, 2015.
Office Action in U.S. Appl. No. 13/602,040, mailed Jul. 6, 2015.
Final Office Action in U.S. Appl. No. 13/684,113, mailed Jul. 1, 2015.
Office Action in U.S. Appl. No. 13/732,050, mailed Jun. 23, 2015.
Office Action in U.S. Appl. No. 13/888,353, mailed Sep. 9, 2015.
Office Action in U.S. Appl. No. 13/937,167 mailed Aug. 17, 2015.
Office Action in U.S. Appl. No. 13/948,004, mailed Jul. 31, 2015.
Office Action in U.S. Appl. No. 13/948,071, mailed Jul. 20, 2015.
Office Action in U.S. Appl. No. 13/948,078, mailed Aug. 5, 2015.
Office Action in U.S. Appl. No. 14/080,768, mailed Jun. 17, 2015.
Office Action in U.S. Appl. No. 14/203,353, mailed Aug. 20, 2015.
Office Action in U.S. Appl. No. 14/304,671, mailed Sep. 3, 2015.
Office Action in U.S. Appl. No. 29/497,888, mailed Jul. 1, 2015.
Search Report and Written Opinion in Singapore application 2013045448 dated Jun. 24, 2015.
Extended European Search Report in European Application No. 13763782.3, dated Jun. 11, 2015.
PCT International Search Report and Written Opinion in International Application No. PCT/US2015/035872, mailed Sep. 3, 2015.
Further Exam Report in European Application No. 13731655.0, dated Aug. 13, 2015.
PCT International Search Report and Written Opinion in International Application No. PCT/US2015/035875, mailed Sep. 4, 2015.
Office Action in U.S. Appl. No. 13/485,878, mailed Aug. 12, 2016.
Office Action in U.S. Appl. No. 13/485,883, mailed Sep. 15, 2016.
Office Action in U.S. Appl. No. 13/948,004, mailed Aug. 15, 2016.
Office Action in U.S. Appl. No. 14/080,768, mailed Sep. 8, 2016.
Office Action in U.S. Appl. No. 14/304,671, mailed Oct. 20, 2016.
Notice of Allowance in U.S. Appl. No. 14/466,805, mailed Aug. 30, 2016.
Notice of Allowance in U.S. Appl. No. 14/466,824, mailed Aug. 12, 2016.
Office Action in U.S. Appl. No. 15/090,404 mailed Sep. 16, 2016.
Notice of Allowance in U.S. Appl. No. 14/667,608 mailed Oct. 19, 2016.
Office Action in U.S. Appl. No. 15/241,019 mailed Oct. 19, 2016.
Office Action in U.S. Appl. No. 13/485,854, mailed Nov. 4, 2016.

\* cited by examiner

Frozen Nutritional Substance ΔN

PRESERVATION SYSTEM FOR NUTRITIONAL SUBSTANCES

RELATED PATENT APPLICATIONS

This application is a continuation-in-part of Utility application Ser. No. 13/485,854 filed May 31, 2012, which claims priority to U.S. Provisional Patent Application Ser. No. 61/624,948 filed Apr. 16, 2012; U.S. Provisional Patent Application Ser. No. 61/624,972, filed Apr. 16, 2012; and U.S. Provisional Patent Application, 61/624,985, filed Apr. 16, 2012, the contents of which are incorporated herein by reference in their entirety.

FIELD OF THE INVENTION

The present inventions relate to creation, collection, transmission, and use of information regarding the preservation of nutritional substances.

BACKGROUND OF THE INVENTION

Nutritional substances are traditionally grown (plants), raised (animals) or synthesized (synthetic compounds). Additionally, nutritional substances can be found in a wild, non-cultivated form, which can be caught or collected. While the collectors and creators of nutritional substances generally obtain and/or generate information about the source, history, caloric content and/or nutritional content of their products, they generally do not pass such information along to the users of their products. One reason is the nutritional substance industries have tended to act like "silo" industries. Each group in the food and beverage industry: growers, packagers, processors, distributors, retailers, and preparers work separately, and either shares no information, or very little information, between themselves. There is generally no consumer access to, and little traceability of, information regarding the creation and/or origin, preservation, processing, preparation, or consumption of nutritional substances. It would be desirable for such information be available to the consumers of nutritional substances, as well as all participants in the food and beverage industry—the nutritional substance supply system.

While the nutritional substance supply system has endeavored over the last 50 years to increase the caloric content of nutritional substances produced (which has helped reduce starvation in developing countries, but has led to obesity and other problems in developed countries), maintaining, or increasing, the nutritional content of nutritional substances has been a lower priority and is done in a synthetic manner. Caloric content refers to the energy in nutritional substances, commonly measured in calories. The caloric content could be represented as sugars and/or carbohydrates in the nutritional substances. The nutritional content, also referred to herein as nutritional value, of foods and beverages, as used herein, refers to the non-caloric content of these nutritional substances which are beneficial to the organisms which consume these nutritional substances. For example, the nutritional content of a nutritional substance could include vitamins, minerals, proteins, and other non-caloric components which are necessary, or at least beneficial, to the organism consuming the nutritional substances.

While there has recently been greater attention by consumer organizations, health organizations and the public to the nutritional content of foods and beverages, the food and beverage industry has been slow in responding to this attention. One reason for this may be that since the food and beverage industry operates as silos of those who create nutritional substances, those who preserve and transport nutritional substances, those who transform nutritional substances, and those who finally prepare the nutritional substances for consumption by the consumer, there has been no system wide coordination or management of nutritional content, and no practical way for creators, preservers, transformers, and conditioners to update labeling content for nutritional substances. While each of these silo industries may be able to maintain or increase the nutritional content of the foods and beverages they handle, each silo industry has only limited information and control of the nutritional substances they receive, and the nutritional substances they pass along.

As consumers better understand their need for nutritional substances with higher nutritional content, they will start demanding that the food and beverage industry offer products which include higher nutritional content, and/or at least information regarding nutritional content of such products, as well as information regarding the source, creation and other origin information for the nutritional substance. In fact, consumers are already willing to pay higher prices for higher nutritional content. This can be seen at high-end grocery stores which offer organic, minimally processed, fresh, non-adulterated nutritional substances. Further, as societies and governments seek to improve their constituents' health and lower healthcare costs, incentives and/or mandates will be given to the food and beverage industry to track, maintain, and/or increase the nutritional content of nutritional substances they handle. There will be a need, not only within each food and beverage industry silo to maintain or improve the nutritional content of their products, but an industry-wide solution to allow the management of nutritional content across the entire cycle from creation to consumption. In order to manage the nutritional content of nutritional substances across the entire cycle from creation to consumption, the nutritional substance industry will need to identify, track, measure, estimate, preserve, transform, condition, and record nutritional content for nutritional substances. Of particular importance is the measurement, estimation, and tracking of changes to the nutritional content of a nutritional substance from creation to consumption. This information could be used, not only by the consumer in selecting particular nutritional substances to consume, but could be used by the other food and beverage industry silos, including creation, preservation, transformation, and conditioning, to make decisions on how to create, handle and process nutritional substances. Additionally, those who sell nutritional substances to consumers, such as restaurants and grocery stores, could communicate perceived qualitative values of the nutritional substance in their efforts to market and position their nutritional substance products. Further, a determinant of price of the nutritional substance could be particular nutritional, organoleptic, or aesthetic values, and if changes to those values are perceived as desirable. For example, if a desirable value has been maintained, improved, or minimally degraded, it could be marketed as a premium product. Still further, a system allowing creators, preservers, transformers, and conditioners of nutritional substances to update labeling content to reflect the most current information about the nutritional substance would provide consumers with the information they need to make informed decisions regarding the nutritional substances they purchase and consume. Such information updates could include nutritional, organoleptic, or aesthetic values of the nutritional substance, and may further include information regarding the source, creation and other origin information for the nutritional substance.

For example, the grower of sweet corn generally only provides basic information as the variety and grade of its corn to the packager, who preserves and ships the corn to a producer for use in a ready-to-eat dinner. The packager may only tell the producer that the corn has been frozen as loose kernels of sweet corn. The producer may only provide the consumer with rudimentary instructions how to cook or reheat the ready-to-eat dinner in a microwave oven, toaster oven or conventional oven, and only tell the consumer that the dinner contains whole kernel corn among the various items in the dinner. Finally, the consumer of the dinner will likely keep her opinions on the quality of the dinner to herself, unless it was an especially bad experience, where she might contact the producer's customer support program to complain. Very minimal, or no, information on the nutritional content of the ready-to-eat dinner is passed along to the consumer. The consumer knows essentially nothing about changes (generally a degradation, but could be a maintenance or even an improvement) to the nutritional content of the sweet corn from creation, processing, packaging, cooking, preservation, preparation by consumer, and finally consumption by the consumer. The consumer is even more unlikely to be aware of possible changes to labeling content that a creator, preserver, transformer, or conditioner may just have become be aware of, such as changes in information about nutritional, organoleptic, or aesthetic values of the nutritional substance or changes in information regarding the source, creation and other origin information about the nutritional substance. If communicated, such changes to labeling content could affect a purchasing preference or consumption preference of a consumer. Further, if communicated, such changes to labeling content could affect the health, safety, and wellbeing of the consumer. It is also clear that such changes would best be communicated rapidly and by a means readily utilized by a consumer.

Consumers' needs are changing as consumers are demanding healthier foods, such as "organic foods." Consumers are also asking for more information about the nutritional substances they consume, such as specific characteristics' relating not only to nutritional content, but to allergens or digestive intolerances. For example, nutritional substances which contain lactose, gluten, nuts, dyes, etc. need to be avoided by certain consumers. However, the producer of the ready-to-eat dinner, in the prior example, has very little information to share other than possibly the source of the elements of the ready-to-eat dinner and its processing steps in preparing the dinner. Generally, the producer of the ready-to-eat dinner does not know the nutritional content and organoleptic state and aesthetic condition of the product after it has been reheated or cooked by the consumer, cannot predict changes to these properties, and cannot inform a consumer of this information to enable the consumer to better meet their needs. For example, the consumer may want to know what proportion of desired organoleptic properties or values, desired nutritional content or values, or desired aesthetic properties or values of the corn in the ready-to-eat dinner remain after cooking or reheating, and the change in the desired nutritional content or values, the desired organoleptic properties or values, or the desired aesthetic properties or values (usually a degradation, but could be a maintenance or even improvement). There is a need to preserve, measure, estimate, store and/or transmit information regarding such nutritional, organoleptic, and aesthetic values, including changes to these values, throughout the nutritional substance supply system. Given the opportunity and a system capable of receiving and processing real time consumer feedback and updates regarding changes in the nutritional, organoleptic, and/or aesthetic value of nutritional substances, consumers can even play a role in updating dynamic information about the nutritional substances they have purchased and/or prepared for consumption, such that that information is available and useful to others in the nutritional substance supply system.

The caloric and nutritional content information for a prepared food that is provided to the consumer is often minimal. For example, when sugar is listed in the ingredient list, the consumer generally does receive any information about the source of the sugar, which can come from a variety of plants, such as sugarcane, beets, or corn, which will affect its nutritional content. Conversely, some nutritional information that is provided to consumers is so detailed, the consumer can do little with it. For example, this of ingredients is from a nutritional label on a consumer product: Vitamins—A 355 IU 7%, E 0.8 mg 4%, K 0.5 mcg, 1%, Thiamin 0.6 mg 43%, Riboflavin 0.3 mg 20%, Niacin 6.0 mg 30%, B6 1.0 mg 52%, Foliate 31.5 mcg 8%, Pantothenic 7%; Minerals Calcium 11.6 1%, Iron 4.5 mg 25%, Phosphorus 349 mg 35%, Potassium 476 mg 14%, Sodium 58.1 mg 2%, Zinc 3.7 mg 24%, Copper 0.5 mg 26%, Manganese 0.8 mg 40%, Selenium 25.7 mcg 37%; Carbohydrate 123 g, Dietary fiber 12.1 g, Saturated fat 7.9 g, Monosaturated Fat 2.1 g, Polysaturated Fat 3.6 g, Omega 3 fatty acids 108 g, Omega 6 fatty acids 3481, Ash 2.0 g and Water 17.2 g. (%=Daily Value). There is a need to provide information about nutritional substances in a meaningful manner. Such information needs to be presented in a manner that meets the specific needs of a particular consumer. For example, consumers with a medical condition, such as diabetes, would want to track specific information regarding nutritional values associated with sugar and other nutrients in the foods and beverages they consume, and would benefit further from knowing changes in these values or having tools to quickly indicate or estimate these changes in a retrospective, current, or prospective fashion, and even tools to report these changes, or impressions of these changes, in a real-time fashion.

In fact, each silo in the food and beverage industry already creates and tracks some information, including caloric and nutritional information, about their product internally. For example, the farmer who grew the corn knows the variety of the seed, condition of the soil, the source of the water, the fertilizers and pesticides used, and can measure the caloric and nutritional content at creation. The packager of the corn knows when it was picked, how it was transported to the packaging plant, how the corn was preserved and packaged before being sent to the ready-to-eat dinner producer, when it was delivered to the producer, and what degradation to caloric and nutritional content has occurred. The producer knows the source of each element of the ready-to-eat dinner, how it was processed, including the recipe followed, and how it was preserved and packaged for the consumer. Not only does such a producer know what degradation to caloric and nutritional content occurred, the producer can modify its processing and post-processing preservation to minimally affect nutritional content. The preparation of the nutritional substance for consumption can also degrade the nutritional content of nutritional substances. Finally, the consumer knows how she prepared the dinner, what condiments were added, and whether she did or did not enjoy it.

If there was a mechanism to share this information, the quality of the nutritional substances, including caloric and nutritional, organoleptic, and aesthetic value, could be preserved and improved. Consumers could be better informed about nutritional substances they select and consume, including the state, and changes in the state, of the nutritional substance throughout its lifecycle from creation to consumption. The efficiency and cost effectiveness of nutritional substances could also be improved. Feedback within the entire chain from creator to consumer could provide a closed-loop system that could improve quality (taste, appearance, and caloric and nutritional content), efficiency, value and profit. For example, in the milk supply chain, at least 10% of the milk produced is wasted due to safety margins included in product expiration dates. The use of more accurate tracking information, measured quality (including nutritional content) information, and historical environmental information could substantially reduce such waste. Collecting, preserving, measuring and/or tracking information about a nutritional substance in the nutritional substance supply system, would allow needed accountability. There would be nothing to hide.

As consumers are demanding more information about what they consume, they are asking for products that have higher and better nutritional content and more closely match good nutritional requirements, and would like nutritional products to actually meet their specific nutritional requirements. While grocery stores, restaurants, and all those who process and sell food and beverages may obtain some information from current nutritional substance tracking systems, such as labels, these current systems can provide only limited information.

Current packaging materials for nutritional substances include plastics, paper, cardboard, glass, and synthetic materials. Generally, the packaging material is chosen by the producer to best preserve the quality of the nutritional substance until used by the customer. In some cases, the packaging may include some information regarding type of nutritional substance, identity of the producer, and the country of origin. Such packaging generally does not transmit source information of the nutritional substance, such as creation information, current or historic information as to the external conditions of the packaged nutritional substance, or current or historic information as to the internal conditions of the packaged nutritional substance.

An important issue in the creation, preservation, transformation, conditioning, and consumption of nutritional substances are the changes that occur in nutritional substances due to a variety of internal and external factors. Because nutritional substances are composed of biological, organic, and/or chemical compounds, they are generally subject to degradation. This degradation generally reduces the nutritional, organoleptic, and/or aesthetic values of nutritional substances. While not always true, nutritional substances are best consumed at their point of creation. However, being able to consume nutritional substances at the farm, at the slaughterhouse, at the fishery, or at the food processing plant is at least inconvenient, if not impossible. Currently, the food and beverage industry attempts to minimize the loss of nutritional, organoleptic, and/or aesthetic value (often through the use of additives or preservatives and often through freezing the nutritional substance), and/or attempts to hide this loss of nutritional, organoleptic, and/or aesthetic value from consumers.

Overall, the examples herein of some prior or related systems and their associated limitations are intended to be illustrative and not exclusive. Other limitations of existing or prior systems will become apparent to those of skill in the art upon reading the following Detailed Description.

OBJECTS OF THE INVENTION

It is an object of the present invention to minimize and/or track degradation of nutritional, organoleptic, and/or aesthetic value of nutritional substances, and/or collect, store, and/or transmit information regarding this degradation.

It is an object of the present invention to minimize and/or track degradation of nutritional, organoleptic, and/or aesthetic value of nutritional substances, and/or collect, store, transmit, and/or make information regarding this degradation available to consumers and others in the nutritional substance supply system.

It is an object of the present invention that the packaging for a nutritional substance directly or indirectly allows for the preservation and tracking of source information, information as to the history of the nutritional substance from the point it was packaged and/or current information on outside or external influences on the packaged nutritional substance, including the target storage conditions and the influence on the nutritional substance of expected and unexpected variations from the target storage conditions.

It is an object of the present invention that the packaging for a nutritional substance directly or indirectly allows for source information, information as to the history of the nutritional substance from the point it was packaged and/or current information on outside or external influences on the packaged nutritional substance, including the target storage conditions and the influence on the nutritional substance of expected and unexpected variations from the target storage conditions, to be available to users and/or consumers of the nutritional substance, or to any member of the nutritional substance supply system.

It is an object of the present invention that the packaging for the nutritional substance can directly or indirectly provide information to the consumer, or to others in the nutritional substance supply system, as to the current state of the nutritional substance in terms of changes in a nutritional, organoleptic, or aesthetic value, or in terms of a current nutritional, organoleptic, or aesthetic value.

It is an object of the present invention that the packaging of the nutritional substance can interact with the nutritional substance to maintain and/or minimize degradation of and/or improve a nutritional, organoleptic or aesthetic value of the nutritional substance during preservation, or in some way optimize any one or combination of a nutritional, organoleptic or aesthetic value of the nutritional substance.

It is an object of the present invention that the packaging or labeling of a nutritional substance directly or indirectly preserves and tracks creation and historical information of the nutritional substance as well as current information about a nutritional, organoleptic or aesthetic state of the nutritional substance or changes to a nutritional, organoleptic or aesthetic state of the nutritional substance.

It is an object of the present invention that the packaging for the nutritional substance includes any form of encoded information, such as information contained on a tag or label, which can directly or indirectly preserve, track, and provide information to the consumer or others within the nutritional substance supply system as to the nutritional substance's source information and/or historical preservation information, including external influences on the nutritional substance, and/or changes in a nutritional, organoleptic, or aesthetic value of the nutritional substance or information regarding the current state of a nutritional, organoleptic, or aesthetic value of the nutritional substance.

It is an object of the present invention to provide a system for the creation, collection, storage, transmission, and/or processing of information regarding a nutritional substance so as to improve, maintain, or minimize degradation of a nutritional, organoleptic, or aesthetic value of the nutritional substance. Additionally, the present invention provides such information for use by the creators, preservers, transformers, conditioners, and consumers of nutritional substances.

SUMMARY OF THE INVENTION

In an embodiment of the present invention, degradation of a nutritional, organoleptic, or aesthetic value of nutritional substances is minimized and/or tracked, and information regarding this degradation is collected, stored, and/or transmitted.

In an embodiment of the present invention, degradation of a nutritional, organoleptic, or aesthetic value of nutritional substances is minimized and/or tracked, and information regarding this degradation is provided to consumers and others in the nutritional substance supply system.

In one embodiment of the present invention, the packaging for a nutritional substance directly or indirectly allows for the preservation and tracking of source information, information as to the history of the nutritional substance from the point it was packaged and/or current information on outside or external influences on the packaged nutritional substance, including the target storage conditions and the influence on the nutritional substance of expected and unexpected variations from the target storage conditions.

In one embodiment of the present invention, the packaging for a nutritional substance directly or indirectly allows for source information, information as to the history of the nutritional substance from the point it was packaged and/or current information on outside or external influences on the packaged nutritional substance, including the target storage conditions and the influence on the nutritional substance of expected and unexpected variations from the target storage conditions, to be available to users and/or consumers of the nutritional substance, or to any member of the nutritional substance supply system.

In another embodiment of the present invention the packaging for the nutritional substance can directly or indirectly provide information to the consumer, or to others in the nutritional substance supply system, as to the current state of the nutritional substance in terms of changes in a nutritional, organoleptic, or aesthetic value, or in terms of a current nutritional, organoleptic, or aesthetic value.

In a further embodiment of the present invention, the packaging of the nutritional substance can interact with the nutritional substance to maintain and/or minimize degradation and/or improve a nutritional, organoleptic or aesthetic value of the nutritional substance during preservation, or in some way to optimize any one or combination of a nutritional, organoleptic or aesthetic value of the nutritional substance.

In an embodiment of the present invention the packaging or labeling of a nutritional substance directly or indirectly preserves and tracks creation and historical information of the nutritional substance as well as current information about a nutritional, organoleptic or aesthetic state of the nutritional substance or changes to a nutritional, organoleptic or aesthetic state of the nutritional substance.

In another embodiment of the present invention the packaging for the nutritional substance includes any form of encoded information, such as information contained on a tag or label, which can directly or indirectly preserve, track, and provide information to the consumer or others within the nutritional substance supply system as to the nutritional substance's source information and/or historical preservation information, including external influences on the nutritional substance, and/or changes in a nutritional, organoleptic, or aesthetic value of the nutritional substance or information regarding the current state of a nutritional, organoleptic, or aesthetic value of the nutritional substance.

An embodiment of the present invention provides a system for the creation, collection, storage, transmission, and/or processing of information regarding a nutritional substance so as to improve, maintain, or minimize degradation of a nutritional, organoleptic, or aesthetic value of the nutritional substance. Additionally, the present invention provides such information for use by the creators, preservers, transformers, conditioners, and consumers of nutritional substance.

Other advantages and features will become apparent from the following description and claims. It should be understood that the description and specific examples are intended for purposes of illustration only and not intended to limit the scope of the present disclosure.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

Figure 1:
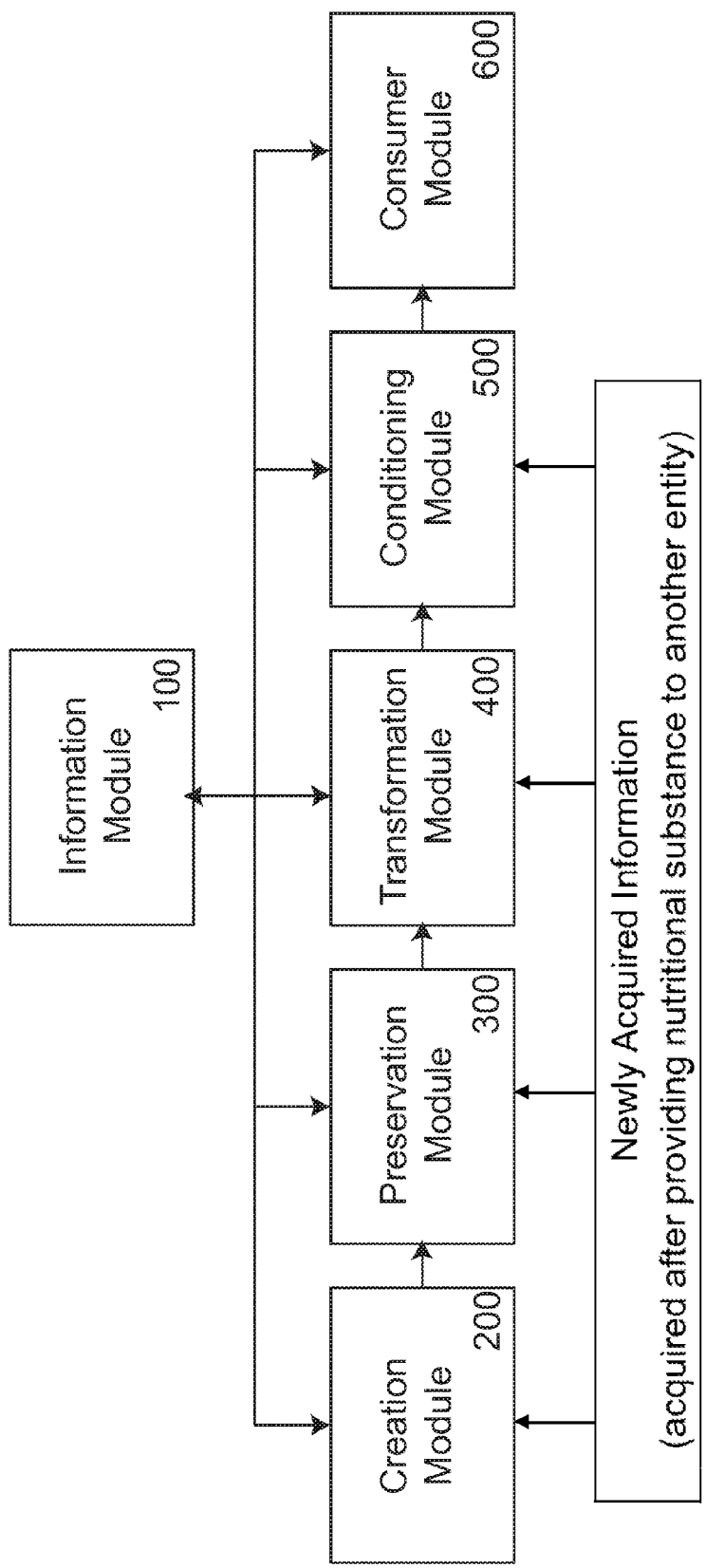
FIG. 1 shows a schematic functional block diagram of a nutritional substance supply system relating to the present invention.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION OF THE INVENTION

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

The following discussion provides a brief, general description of a representative environment in which the invention can be implemented. Although not required, aspects of the invention may be described below in the general context of computer-executable instructions, such as routines executed by a general-purpose data processing device (e.g., a server computer or a personal computer). Those skilled in the relevant art will appreciate that the invention can be practiced with other communications, data processing, or computer system configurations, including: wireless devices, Internet appliances, hand-held devices (including personal digital assistants (PDAs)), wearable computers, all manner of cellular or mobile phones, multi-processor systems, microprocessor-based or programmable consumer electronics, set-top boxes, network PCs, mini-computers, mainframe computers, and the like. Indeed, the terms "controller," "computer," "server," and the like are used interchangeably herein, and may refer to any of the above devices and systems.

While aspects of the invention, such as certain functions, are described as being performed exclusively on a single device, the invention can also be practiced in distributed environments where functions or modules are shared among disparate processing devices. The disparate processing devices are linked through a communications network, such as a Local Area Network (LAN), Wide Area Network (WAN), or the Internet. In a distributed computing environment, program modules may be located in both local and remote memory storage devices.

Aspects of the invention may be stored or distributed on tangible computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data related to the invention may be distributed over the Internet or over other networks (including wireless networks), on a propagated signal on a propagation medium (e.g., an electromagnetic wave(s), a sound wave, etc.) over a period of time. In some implementations, the data may be provided on any analog or digital network (packet switched, circuit switched, or other scheme).

In some instances, the interconnection between modules is the internet, allowing the modules (with, for example, WiFi capability) to access web content offered through various web servers. The network may be any type of cellular, IP-based or converged telecommunications network, including but not limited to Global System for Mobile Communications (GSM), Time Division Multiple Access (TDMA), Code Division Multiple Access (CDMA), Orthogonal Frequency Division Multiple Access (OFDM), General Packet Radio Service (GPRS), Enhanced Data GSM Environment (EDGE), Advanced Mobile Phone System (AMPS), Worldwide Interoperability for Microwave Access (WiMAX), Universal Mobile Telecommunications System (UMTS), Evolution-Data Optimized (EVDO), Long Term Evolution (LTE), Ultra Mobile Broadband (UMB), Voice over Internet Protocol (VoIP), Unlicensed Mobile Access (UMA), etc.

The modules in the systems can be understood to be integrated in some instances and in particular embodiments, only particular modules may be interconnected.

FIG. 1 shows the components of a nutritional substance industry 10. It should be understood that this could be the food and beverage ecosystem for human consumption, but could also be the feed industry for animal consumption, such as the pet food industry. A goal of the present invention for nutritional substance industry 10 is to create, preserve, transform and trace the change in nutritional, organoleptic and/or aesthetic values of nutritional substances, collectively and individually also referred to herein as $\Delta N$, through their creation, preservation, transformation, conditioning and consumption. While the nutritional substance industry 10 can be composed of many companies or businesses, it can also be integrated into combinations of business serving many roles, or can be one business or even individual. Since $\Delta N$ is a measure of the change in a value of a nutritional substance, knowledge of a prior value (or state) of a nutritional substance and the $\Delta N$ value will provide knowledge of the changed value (or state) of a nutritional substance, and can further provide the ability to estimate a change in value (or state).

Module 200 is the creation module. This can be a system, organization, or individual which creates and/or originates nutritional substances. Examples of this module include a farm which grows produce; a ranch which raises beef; an aquaculture farm for growing shrimp; a factory that synthesizes nutritional compounds; a collector of wild truffles; or a deep sea crab trawler.

Preservation module 300 is a preservation system for preserving and protecting the nutritional substances created by creation module 200. Once the nutritional substance has been created, generally, it will need to be packaged in some manner for its transition to other modules in the nutritional substances industry 10. While preservation module 300 is shown in a particular position in the nutritional substance industry 10, following the creation module 200, it should be understood that the preservation module 300 actually can be placed anywhere nutritional substances need to be preserved during their transition from creation to consumption.

Transformation module 400 is a nutritional substance processing system, such as a manufacturer who processes raw materials such as grains into breakfast cereals. Transformation module 400 could also be a ready-to-eat dinner manufacturer who receives the components, or ingredients, also referred to herein as component nutritional substances, for a ready-to-eat dinner from preservation module 300 and prepares them into a frozen dinner. While transformation module 400 is depicted as one module, it will be understood that nutritional substances may be transformed by a number of transformation modules 400 on their path to consumption.

Conditioning module 500 is a consumer preparation system for preparing the nutritional substance immediately before consumption by the consumer. Conditioning module 500 can be a microwave oven, a blender, a toaster, a convection oven, a cook, etc. It can also be systems used by commercial establishments to prepare nutritional substance for consumers such as a restaurant, an espresso maker, pizza oven, and other devices located at businesses which provide nutritional substances to consumers. Such nutritional substances could be for consumption at the business or for the consumer to take out from the business. Conditioning module 500 can also be a combination of any of these devices used to prepare nutritional substances for consumption by consumers.

Consumer module 600 collects information from the living entity which consumes the nutritional substance which has passed through the various modules from creation to consumption. The consumer can be a human being, but could also be an animal, such as pets, zoo animals and livestock, which are they themselves nutritional substances for other consumption chains. Consumers could also be plant life which consumes nutritional substances to grow.

Information module 100 receives and transmits information regarding a nutritional substance between each of the modules in the nutritional substance industry 10 including, the creation module 200, the preservation module 300, the transformation module 400, the conditioning module 500, and the consumer module 600. The nutritional substance information module 100 can be an interconnecting information transmission system which allows the transmission of information between various modules. Information module 100 contains a database, also referred to herein as a dynamic nutritional value database, where the information regarding the nutritional substance resides. Information module 100 can be connected to the other modules by a variety of communication systems, such as paper, computer networks, the internet and telecommunication systems, such as wireless telecommunication systems. In a system capable of receiving and processing real time consumer feedback and updates regarding changes in the nutritional, organoleptic, and/or aesthetic value of nutritional substances, or $\Delta N$, consumers can even play a role in updating a dynamic nutritional value database with observed or measured information about the nutritional substances they have purchased and/or prepared for consumption, so that the information is available and useful to others in the nutritional substance supply system, such as through reports reflecting the consumer input or through modification of $\Delta N$.

Figure 2:
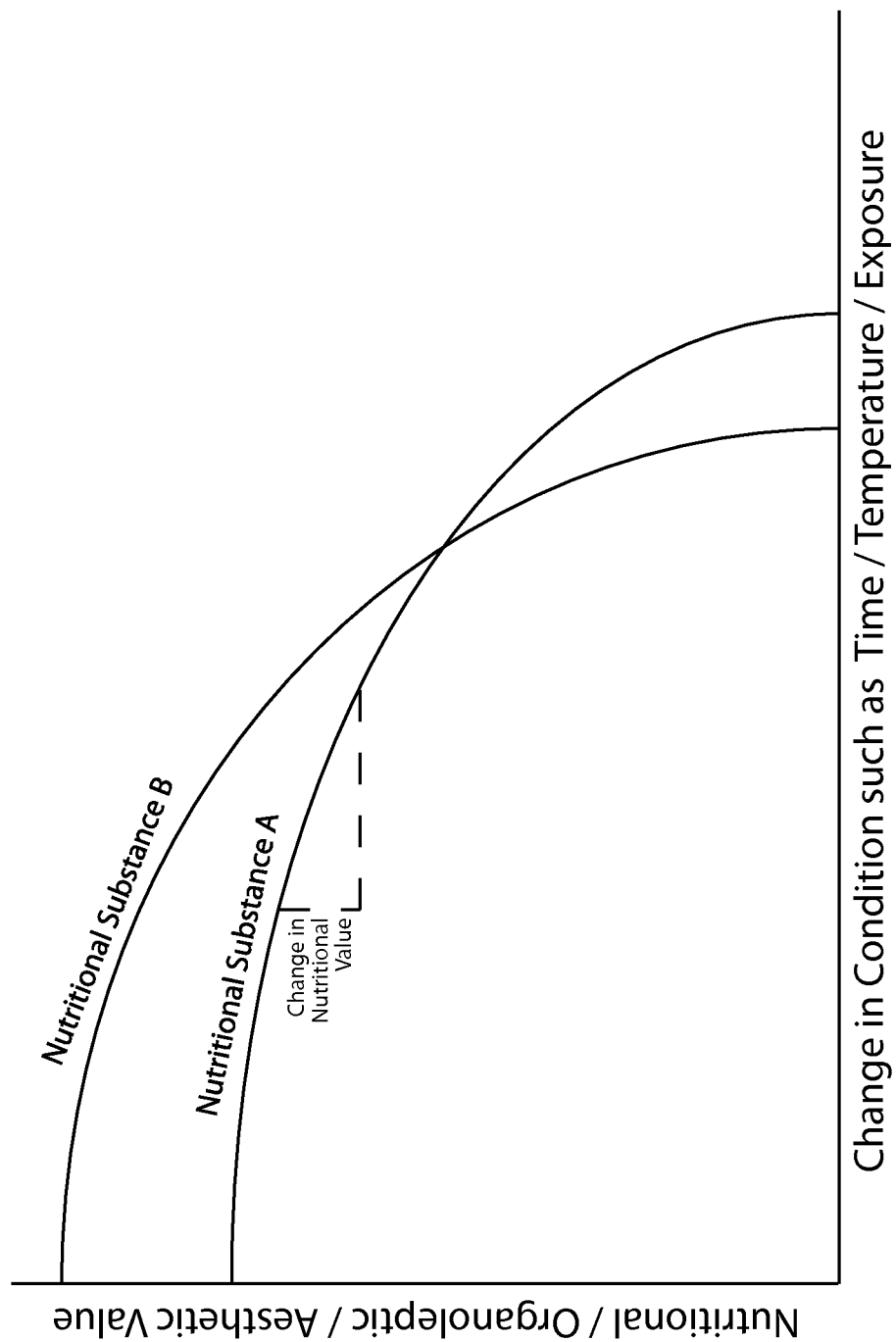
FIG. 2 shows a graph representing a value of a nutritional substance which changes according to a change of condition for the nutritional substance.

FIG. 2 is a graph showing the function of how a nutritional, organoleptic, or aesthetic value of a nutritional substance varies over the change in a condition of the nutritional substance. Plotted on the vertical axis of this graph can be either the nutritional value, organoleptic value, or even the aesthetic value of a nutritional substance. Plotted on the horizontal axis can be the change in condition of the nutritional substance over a variable such as time, temperature, location, and/or exposure to environmental conditions. This exposure to environmental conditions can include: exposure to air, including the air pressure and partial pressures of oxygen, carbon dioxide, water, or ozone; airborne chemicals, pollutants, allergens, dust, smoke, carcinogens, radioactive isotopes, or combustion byproducts; exposure to moisture; exposure to energy such as mechanical impact, mechanical vibration, irradiation, heat, or sunlight; or exposure to materials such as packaging. The function plotted as nutritional substance A could show a $\Delta N$ for milk, such as the degradation of a nutritional value of milk over time. Any point on this curve can be compared to another point to measure and/or describe the change in nutritional value, or the $\Delta N$ of nutritional substance A. The plot of the degradation in the same nutritional value of nutritional substance B, also milk, describes the change in nutritional value, or the $\Delta N$ of nutritional substance B, a nutritional substance which starts out with a higher nutritional value than nutritional substance A, but degrades over time more quickly than nutritional substance A.

In this example, where nutritional substance A and nutritional substance B are milk, this $\Delta N$ information regarding the nutritional substance degradation profile of each milk could be used by the consumer in the selection and/or consumption of the milk. If the consumer has this information at time zero when selecting a milk product for purchase, the consumer could consider when the consumer plans to consume the milk, whether that is on one occasion or multiple occasions. For example, if the consumer planned to consume the milk prior to the point when the curve represented by nutritional substance B crosses the curve represented by nutritional substance A, then the consumer should choose the milk represented by nutritional substance B because it has a higher nutritional value until it crosses the curve represented by nutritional substance A. However, if the consumer expects to consume at least some of the milk at a point in time after the time when the curve represented by nutritional substance B crosses the curve represented by nutritional substance A, then the consumer might choose to select the milk represented by the nutritional substance A, even though milk represented by nutritional substance A has a lower nutritional value than the milk represented by nutritional substance B at an earlier time. This change to a desired nutritional value in a nutritional substance over a change in a condition of the nutritional substance described in FIG. 2 can be measured and/or controlled throughout nutritional substance supply system 10 in FIG. 1. This example demonstrates how dynamically generated information regarding a $\Delta N$ of a nutritional substance, in this case a change in nutritional value of milk, can be used to understand a rate at which that nutritional value changes or degrades; when that nutritional value expires; and a residual nutritional value of the nutritional substance over a change in a condition of the nutritional substance, in this example a change in time. This $\Delta N$ information could further be used to determine a best consumption date for nutritional substance A and B, which could be different from each other depending upon the dynamically generated information generated for each.

In FIG. 1, Creation module 200 can dynamically encode nutritional substances to enable the tracking of changes in nutritional, organoleptic, and/or aesthetic value of the nutritional substance, or $\Delta N$. This dynamic encoding, also referred to herein as a dynamic information identifier, can replace and/or complement existing nutritional substance marking systems such as barcodes, labels, and/or ink markings. This dynamic encoding, or dynamic information identifier, can be used to make nutritional substance information from creation module 200 available to information module 100 for use by preservation module 300, transformation module 400, conditioning module 500, and/or consumption module 600, which includes the ultimate consumer of the nutritional substance. One method of marking the nutritional substance with a dynamic information identifier by creation module 200, or any other module in nutritional supply system 10, could include an electronic tagging system, such as the tagging system manufactured by Kovio of San Jose, Calif., USA. Such thin film chips can be used not only for tracking nutritional substances, but can include components to measure attributes of nutritional substances, and record and transmit such information. Such information may be readable by a reader including a satellite-based system. Such a satellite-based nutritional substance information tracking system could comprise a network of satellites with coverage of some or all the surface of the earth, so as to allow the dynamic nutritional value database of information module 100 real time, or near real time updates about a $\Delta N$ of a particular nutritional substance.

Preservation module 300 includes packers and shippers of nutritional substances. The tracking of changes in nutritional, organoleptic, and/or aesthetic values, or a $\Delta N$, during the preservation period within preservation module 300 allows for dynamic expiration dates for nutritional substances. For example, expiration dates for dairy products are currently based generally only on time using assumptions regarding minimal conditions at which dairy products are maintained. This extrapolated expiration date is based on a worst-case scenario for when the product becomes unsafe to consume during the preservation period. In reality, the degradation of dairy products may be significantly less than this worst-case. If preservation module 300 could measure or derive the actual degradation information such as $\Delta N$, an actual expiration date, referred to herein as a dynamic expiration date, can be determined dynamically, and could be significantly later in time than an extrapolated expiration date. This would allow the nutritional substance supply system to dispose of fewer products due to expiration dates. This ability to dynamically generate expiration dates for nutritional substances is of particular significance when nutritional substances contain few or no preservatives. Such products are highly valued throughout nutritional substance supply system 10, including consumers who are willing to pay a premium for nutritional substances with few or no preservatives.

It should be noted that a dynamic expiration date need not be indicated numerically (i.e., as a numerical date) but could be indicated symbolically as by the use of colors—such as green, yellow and red employed on semaphores—or other designations. In those instances, the dynamic expiration date would not be interpreted literally but, rather, as a dynamically-determined advisory date. In practice a dynamic expiration date will be provided for at least one component of a single or multi-component nutritional substance. For multi-component nutritional substances, the dynamic expiration date could be interpreted as a "best" date for consumption for particular components.

By law, in many localities, food processors such as those in transformation module 400 are required to provide nutritional substance information regarding their products. Often, this information takes the form of a nutritional table applied to the packaging of the nutritional substance. Currently, the information in this nutritional table is based on averages or minimums for their typical product. Using the nutritional substance information from information module 100 provided by creation module 200, preservation module 300, and/or information from the transformation of the nutritional substance by transformation module 400, the food processor could include a dynamically generated nutritional value table, also referred to herein as a dynamic nutritional value table, for the actual nutritional substance being supplied. The information in such a dynamic nutritional value table could be used by conditioning module 500 in the preparation of the nutritional substance, and/or used by consumption module 600, so as to allow the ultimate consumer the ability to select the most desirable nutritional substance which meets their needs, and/or to track information regarding nutritional substances consumed.

Information about changes in nutritional, organoleptic, and/or aesthetic values of nutritional substances, or $\Delta N$, is particularly useful in the conditioning module 500 of the present invention, as it allows knowing, or estimating, the pre-conditioning state of the nutritional, organoleptic, and/or aesthetic values of the nutritional substance, and allows for estimation of a $\Delta N$ associated with proposed conditioning parameters. The conditioning module 500 can therefore create conditioning parameters, such as by modifying existing or baseline conditioning parameters, to deliver desired nutritional, organoleptic, and/or aesthetic values after conditioning. The pre-conditioning state of the nutritional, organoleptic, and/or aesthetic value of a nutritional substance is not tracked or provided to the consumer by existing conditioners, nor is the $\Delta N$ expected from a proposed conditioning tracked or provided to the consumer either before or after conditioning. However, using information provided by information module 100 from creation module 200, preservation module 300, transformation module 400, and/or information measured or generated by conditioning module 500, conditioning module 500 could provide the consumer with the actual, and/or estimated change in nutritional, organoleptic, and/or aesthetic values of the nutritional substance, or $\Delta N$. Further, consumer feedback and updates regarding observed or measured changes in the nutritional, organoleptic, and/or aesthetic value of nutritional substances, or $\Delta N$, can play a role in updating a dynamic nutritional value database with information about the nutritional substances consumers have purchased and/or prepared for consumption, so that the information is available and useful to others in the nutritional substance supply system, such as through reports reflecting the consumer input or through modification of $\Delta N$. Such information regarding the change to nutritional, organoleptic and/or aesthetic value of the nutritional substance, or $\Delta N$, could be provided not only to the consumer, but could also be provided to information module 100 for use by creation module 200, preservation module 300, transformation module 400, so as to track, and possibly improve nutritional substances throughout the entire nutritional substance supply system 10.

The information regarding nutritional substances provided by information module 100 to consumption module 600 can replace or complement existing information sources such as recipe books, food databases like www.epicurious.com, and Epicurious apps. Through the use of specific information regarding a nutritional substance from information module 100, consumers can use consumption module 600 to select nutritional substances according to nutritional, organoleptic, and/or aesthetic values. This will further allow consumers to make informed decisions regarding nutritional substance additives, preservatives, genetic modifications, origins, traceability, and other nutritional substance attributes that may also be tracked through the information module 100. This information can be provided by consumption module 600 through personal computers, laptop computers, tablet computers, and/or smartphones. Software running on these devices can include dedicated computer programs, modules within general programs, and/or smartphone apps. An example of such a smartphone app regarding nutritional substances is the iOS ShopNoGMO from the Institute for Responsible Technology. This iPhone app allows consumers access to information regarding non-genetically modified organisms they may select. Additionally, consumption module 600 may provide information for the consumer to operate conditioning module 500 in such a manner as to optimize nutritional, organoleptic, and/or aesthetic values of a nutritional substance and/or component nutritional substances thereof, according to the consumer's needs or preference or according to target values established by the provider of the nutritional substance, such as the transformer, and/or minimize degradation of, preserve, or improve nutritional, organoleptic, and/or aesthetic value of a nutritional substance and/or component nutritional substances thereof.

Through the use of nutritional substance information available from information module 100 nutritional substance supply system 10 can track nutritional, organoleptic, and/or aesthetic value. Using this information, nutritional substances travelling through nutritional substance supply system 10 can be dynamically valued and priced according to nutritional, organoleptic, and/or aesthetic values. For example, nutritional substances with longer dynamic expiration dates (longer shelf life) may be more highly valued than nutritional substances with shorter expiration dates. Additionally, nutritional substances with higher nutritional, organoleptic, and/or aesthetic values may be more highly valued, not just by the consumer, but also by each entity within nutritional substance supply system 10. This is because each entity will want to start with a nutritional substance with higher nutritional, organoleptic, and/or aesthetic value before it performs its function and passes the nutritional substance along to the next entity. Therefore, both the starting nutritional, organoleptic, and/or aesthetic value and the $\Delta N$ associated with those values are important factors in determining or estimating an actual, or residual, nutritional, organoleptic, and/or aesthetic value of a nutritional substance, and accordingly are important factors in establishing dynamically valued and priced nutritional substances.

During the period of implementation of the present inventions, there will be nutritional substances being marketed including those benefiting from the tracking of dynamic nutritional information such as $\Delta N$, also referred to herein as information-enabled nutritional substances, and nutritional substances which do not benefit from the tracking of dynamic nutritional information such as $\Delta N$, which are not information enabled and are referred to herein as dumb nutritional substances. Information-enabled nutritional substances would be available in virtual internet marketplaces, as well as traditional marketplaces. Because of information provided by information-enabled nutritional substances, entities within the nutritional substance supply system 10, including consumers, would be able to review and select information-enabled nutritional substances for purchase. It should be expected that, initially, the information-enabled nutritional substances would enjoy a higher market value and price than dumb nutritional substances. However, as information-enabled nutritional substances become more the norm, the cost savings from less waste due to degradation of information-enabled nutritional substances could lead to their price actually becoming less than dumb nutritional substances.

For example, the producer of a ready-to-eat dinner would prefer to use corn of a high nutritional, organoleptic, and/or aesthetic value in the production of its product, the ready-to-eat dinner, so as to produce a premium product of high nutritional, organoleptic, and/or aesthetic value. Depending upon the levels of the nutritional, organoleptic, and/or aesthetic values, the ready-to-eat dinner producer may be able to charge a premium price and/or differentiate its product from that of other producers. When selecting the corn to be used in the ready-to-eat dinner, the producer will seek corn of high nutritional, organoleptic, and/or aesthetic value from preservation module 300 that meets its requirements for nutritional, organoleptic, and/or aesthetic value. The packager/shipper of preservation module 300 would also be able to charge a premium for corn which has high nutritional, organoleptic, and/or aesthetic values. And finally, the packager/shipper of preservation module 300 will select corn of high nutritional, organoleptic, and/or aesthetic value from the grower of creation module 200, who will also be able to charge a premium for corn of high nutritional, organoleptic, and/or aesthetic values.

The change to nutritional, organoleptic, and/or aesthetic value for a nutritional substance, or $\Delta N$, tracked through nutritional substance supply system 10 through nutritional substance information from information module 100 can be preferably determined from measured information. However, some or all such nutritional substance $\Delta N$ information may be derived through measurements of environmental conditions of the nutritional substance as it traveled through nutritional substance supply system 10. Additionally, some or all of the nutritional substance $\Delta N$ information can be derived from $\Delta N$ data of other nutritional substances which have traveled through nutritional substance supply system 10. Nutritional substance $\Delta N$ information can also be derived from laboratory experiments performed on other nutritional substances, which may approximate conditions and/or processes to which the actual nutritional substance has been exposed. Further, consumer feedback and updates regarding observed or measured changes in the nutritional, organoleptic, and/or aesthetic value of nutritional substances can play a role in updating $\Delta N$ information.

For example, laboratory experiments can be performed on bananas to determine effect on or change in nutritional, organoleptic, and/or aesthetic value, or $\Delta N$, for a variety of environmental conditions bananas may be exposed to during packaging and shipment in preservation module 300. Using this experimental data, tables and/or algorithms could be developed which would predict the level of change of nutritional, organoleptic, and/or aesthetic values, or $\Delta N$, for a particular banana based upon information collected regarding the environmental conditions to which the banana was exposed during its time in preservation module 300. While the ultimate goal for nutritional substance supply system 10 would be the actual measurement of nutritional, organoleptic, and/or aesthetic values to determine $\Delta N$, use of derived nutritional, organoleptic, and/or aesthetic values from experimental data to determine $\Delta N$ would allow improved logistics planning because it provides the ability to prospectively estimate changes to nutritional, organoleptic, and/or aesthetic values, or $\Delta N$, and because it allows more accurate tracking of changes to nutritional, organoleptic, and/or aesthetic values, or ΔN, while technology and systems are put in place to allow actual measurement.

Figure 3:
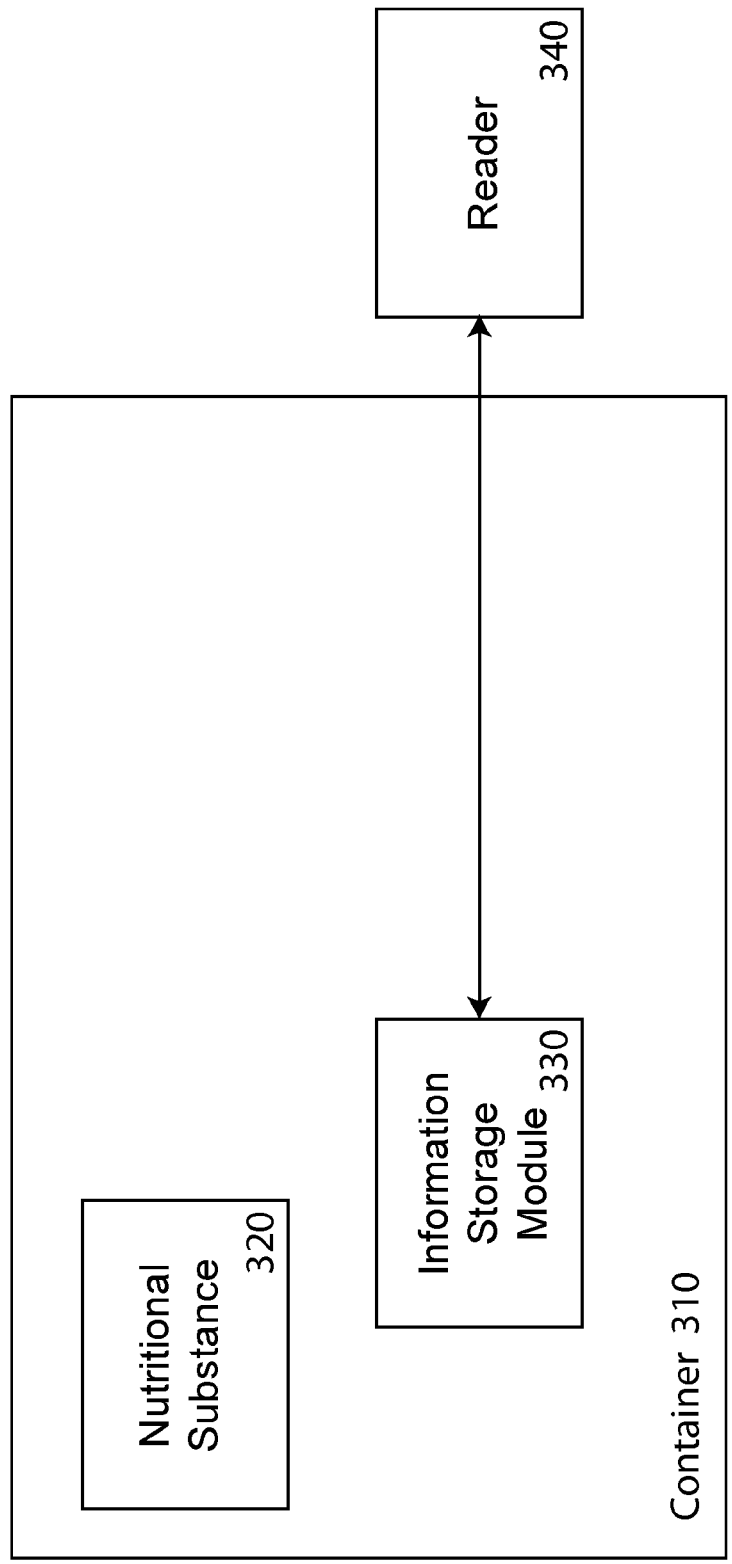
FIG. 3 shows a schematic functional block diagram of the preservation module 300 according to the present invention.

FIG. 3 shows an embodiment of the preservation module of the present invention. Preservation module 300 includes a container 310 which contains nutritional substance 320. Also included in container 310 is information storage module 330 which can be connected to an external reader 340. In this embodiment, information storage module 330 contains information regarding the nutritional substance 320. This information can include creation or origin information from the creation of the nutritional substance 320 and/or prior preservation or transformation information. Information in the information storage module 330 might additionally include identification information, such as a dynamic information identifier provided on the nutritional substance, which is associated with source and origin information or information regarding prior transformation or prior storage or prior transport of the nutritional substance 320 and other historic information preserved in information module 100. A shipper, or user, of container 310 can operatively connect to information storage module 330 using reader 340 to retrieve information stored therein. Information module 100 can connect to reader 340 to retrieve and preserve information stored in information storage module 330 and can further associate that information with the dynamic information identifier provided on the nutritional substance. Alternatively, reader 340 can transmit information stored in information storage module 330 to information module 100 and can further associate the transmitted information with the dynamic information identifier provided on the nutritional substance. A consumer or other member of the nutritional substance supply system would then be able to retrieve from information system 100 the information that was stored in information module 330 by using the dynamic information identifier associated with the nutritional substance and provided on the nutritional substance.

In an alternate embodiment reader 340 can also write to information storage module 330. In this embodiment, information regarding the container and/or nutritional substance 320 can be modified or added to information storage module 330 by the user or shipper.

Figure 4:
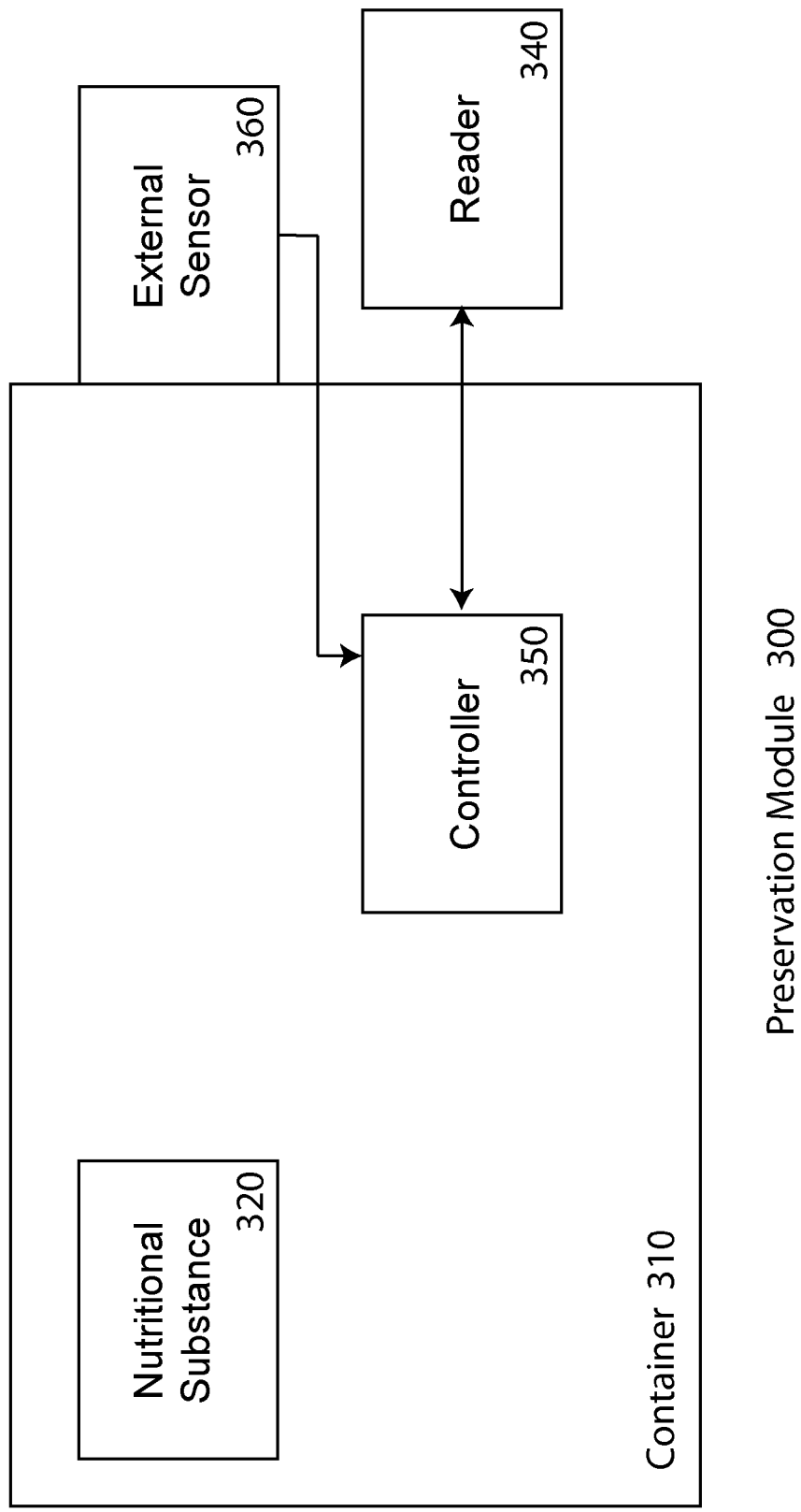
FIG. 4 shows a schematic functional block diagram of the preservation module 300 according to an alternate embodiment of the present invention.

FIG. 4 shows another embodiment of preservation module 300 wherein container 310 contains nutritional substance 320 as well as controller 350. Controller 350 is connected to external sensor 360 located either inside, on the surface of, or external to container 310 such that external sensor 360 can obtain information regarding the environment external to container 310. Controller 350 and exterior sensor 360 can take the form of electronic components such as a microcontroller and an electronic sensor. However, the controller-sensor combination may also be chemical or organic materials which perform the same function, such as a liquid crystal sensor/display.

When the shipper or user of container 310 desires information from external sensor 360 the shipper or user can use reader 340 to query the controller 350 as to the state of external sensor 360. In the electronic component embodiment, reader 340 could be a user interface device such as a computer which can be electronically connected to controller 350. If the controller-sensor combination is a liquid crystal sensor/display, the ready could be a human looking at the display.

Information in the controller 350 can include creation or origin information from the creation of the nutritional substance 320 and/or prior preservation or transformation information. Information in the controller 350 might additionally include identification information, such as a dynamic information identifier provided on the nutritional substance, which is associated with source and origin information or information regarding prior transformation or prior storage or prior transport of the nutritional substance 320 and other historic information preserved in information module 100. A shipper, or user, of container 310 can operatively connect to controller 350 using reader 340 to retrieve information stored therein, such as the identification information and information from external sensor 360. Information module 100 can connect to controller 350 directly, or using reader 340, to retrieve and preserve information stored therein, such as the identification information and information from external sensor 360, and can further associate that information with the dynamic information identifier provided on the nutritional substance. Alternatively, controller 350 or reader 340 can transmit information stored in controller 350 and collected by controller 350 from external sensor 360 to information module 100 and can further associate the transmitted information with the dynamic information identifier provided on the nutritional substance. A consumer or other member of the nutritional substance supply system would then be able to retrieve from information system 100 the information that was stored and collected by controller 350 by using the dynamic information identifier associated with the nutritional substance and provided on the nutritional substance.

In one embodiment, reader 340 can be directly connected to external sensor 360 to obtain the information from external sensor 360 without need of a controller 350. In another embodiment, external sensor 360 provides information to controller 350 which is presented as a visual display to the shipper or user. Finally, external sensor 360 could provide information directly to the user or shipper by visual means such as a temperature sensitive liquid crystal thermometer.

In an additional embodiment, controller 350 can modify the operation of container 310 so as to modify the preservation capabilities of container 310. For example, if the exterior environment of container 310 would adversely affect the nutritional substance 320, container 310 could adjust the internal environment of container 310 to better preserve the nutritional substance. If nutritional substance needs to be kept within a certain temperature range to preserve its nutritional, organoleptic or aesthetic values or properties, and the external sensor 360 provides exterior temperature information to controller 350, controller 350 could modify container 310 so as to maintain nutritional substance 320 within the required temperature range.

Figure 5:
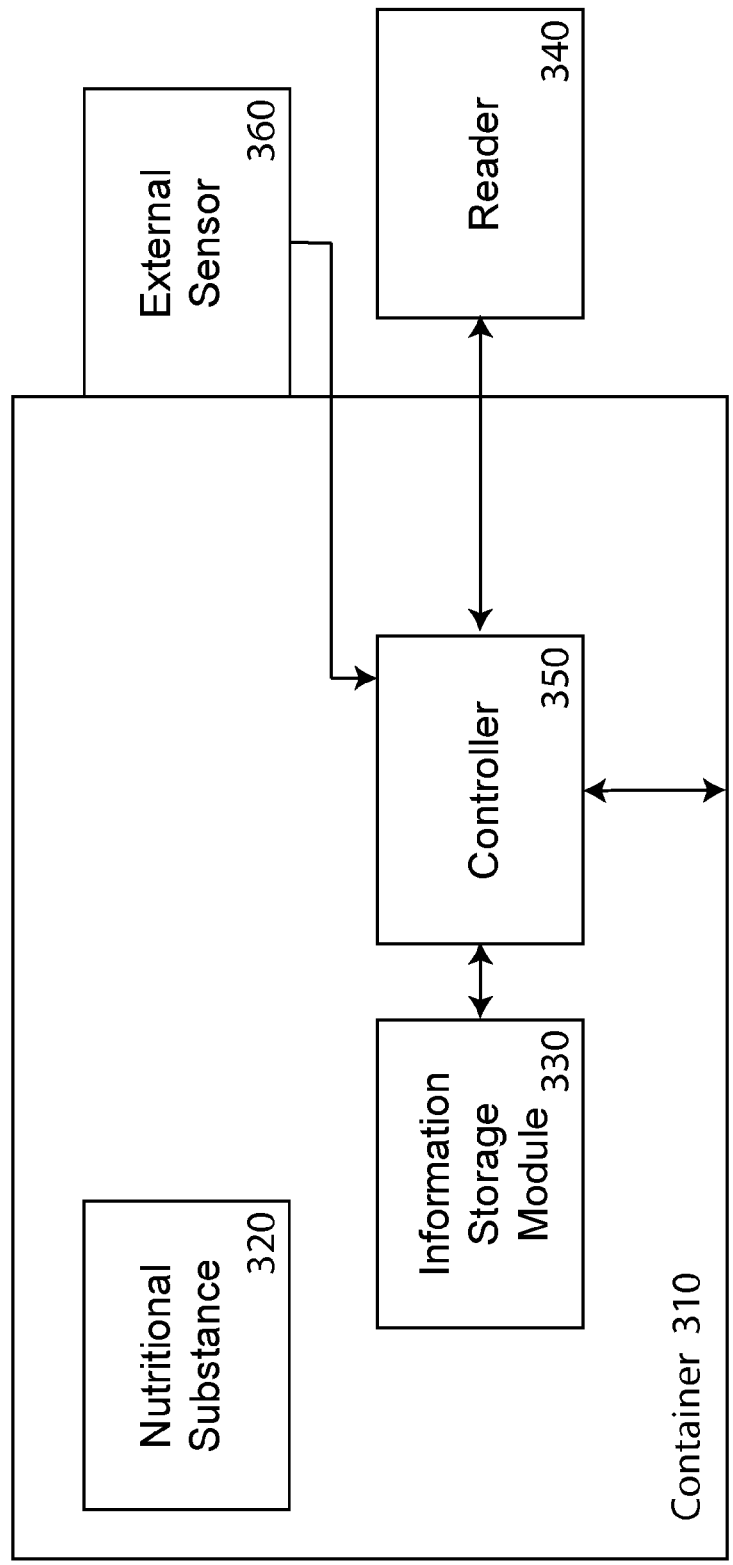
FIG. 5 shows a schematic functional block diagram of the preservation module 300 according to an alternate embodiment of the present invention.

In FIG. 5, preservation module 300 includes container 310 which contains nutritional substance 320, controller 350, and information storage module 330. External sensor 360 is positioned such that it can provide information on the exterior environment to container 310. Information from the external sensor and information storage module can be retrieved by connecting reader 340 to container 310.

In this embodiment, information regarding the external environment sensed by external sensor 360 and provided to controller 350 can be stored in information storage module 330. This storage of external environment can be used to record a history of the external environment container 310 has been subjected to. This would allow the shipper or user of container 310 to understand the external environment the container has been subjected to during the time it has preserved the nutritional substance. Such information can be used to determine if the nutritional substance is no longer safe for consumption or has been degraded such that the nutritional substance is no longer in an optimal state. Additionally, the user of the nutritional substance could modify its transformation, conditioning, or consumption according to any changes that may have occurred because of the external conditions of the container.

Information in the information storage module 330 can include creation or origin information from the creation of the nutritional substance 320 and/or prior preservation or transformation information. Information in information storage module 330 might additionally include identification information, such as a dynamic information identifier provided on the nutritional substance, which is associated with source and origin information or information regarding prior transformation or prior storage or prior transport of the nutritional substance 320 and other historic information preserved in information module 100. A shipper, or user, of container 310 can operatively connect to information storage module 330 through controller 350 using reader 340 to retrieve information stored in storage module 330. Information module 100 can operatively connect to information storage module 330 through controller 350, or using reader 340, to retrieve and preserve information stored in storage module 330, and can further associate that information with the dynamic information identifier provided on the nutritional substance. Alternatively, controller 350 or reader 340 can transmit information stored in information storage module 330 to information module 100 and can further associate the transmitted information with the dynamic information identifier provided on the nutritional substance. A consumer or other member of the nutritional substance supply system would then be able to retrieve from information system 100 the information that was stored in controller 350 by using the dynamic information identifier associated with the nutritional substance and provided on the nutritional substance.

In an additional embodiment, controller 350 can modify the operation of container 310 so as modify the preservation capabilities of container 310. For example, if the exterior environment of container 310 would adversely affect the nutritional substance 320, container 310 could adjust the internal environment of container 310 to better preserve the nutritional substance. Controller 350 can analyze the historic information from external sensor 360, stored in information storage module 330 to determine any long-term exterior conditions environmental If nutritional substance needs to be kept within a certain temperature range to preserve its nutritional, organoleptic or aesthetic values or properties, and the external sensor 360 provides exterior temperature information to controller 350, controller 350 could modify container 310 so as to maintain nutritional substance 320 within the required temperature range.

Figure 6:
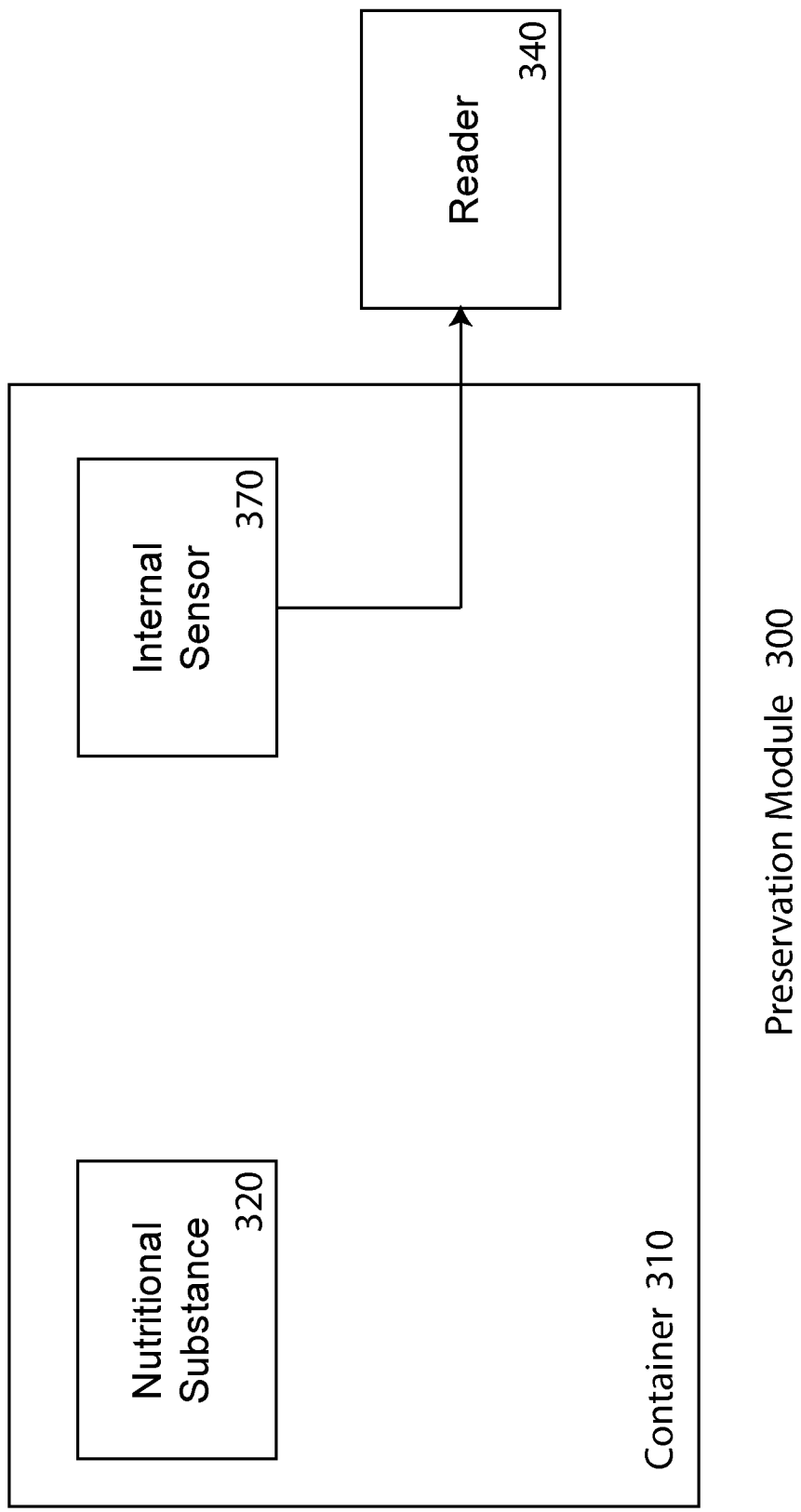
FIG. 6 shows a schematic functional block diagram of the preservation module 300 according to an alternate embodiment of the present invention.

FIG. 6 shows an embodiment of preservation module 300 wherein container 310 contains nutritional substance 320 as well as internal sensor 370 located either inside, or on the surface of, container 310, such that internal sensor 370 can obtain information regarding the environment internal to container 310. Internal sensor 370 can be connected to reader 340 to obtain the interior conditions of container 310. Internal sensor 370 and reader 340 can take the form of electronic components such as an electronic sensor and electronic display. However, the reader-sensor combination may also be chemical or organic materials which perform the same function, such as a liquid crystal sensor/display.

In addition to information regarding the environment internal to container 310, information in the internal sensor 370 can include creation or origin information from the creation of the nutritional substance 320 and/or prior preservation or transformation information. Information in the internal sensor 370 might additionally include identification information, such as a dynamic information identifier provided on the nutritional substance, which is associated with source and origin information or information regarding prior transformation or prior storage or prior transport of the nutritional substance 320 and other historic information preserved in information module 100. A shipper, or user, of container 310 can operatively connect to internal sensor 370 using reader 340 to retrieve information stored or collected therein. Information module 100 can connect to internal sensor 370 directly, or using reader 340, to retrieve and preserve information stored or collected therein, and can further associate that information with the dynamic information identifier provided on the nutritional substance. Alternatively, internal sensor 370 or reader 340 can transmit information stored in or collected by internal sensor 370 to information module 100 and can further associate the transmitted information with the dynamic information identifier provided on the nutritional substance. A consumer or other member of the nutritional substance supply system would then be able to retrieve from information system 100 the information that was stored in or collected by internal sensor 370 by using the dynamic information identifier associated with the nutritional substance and provided on the nutritional substance.

Figure 7:
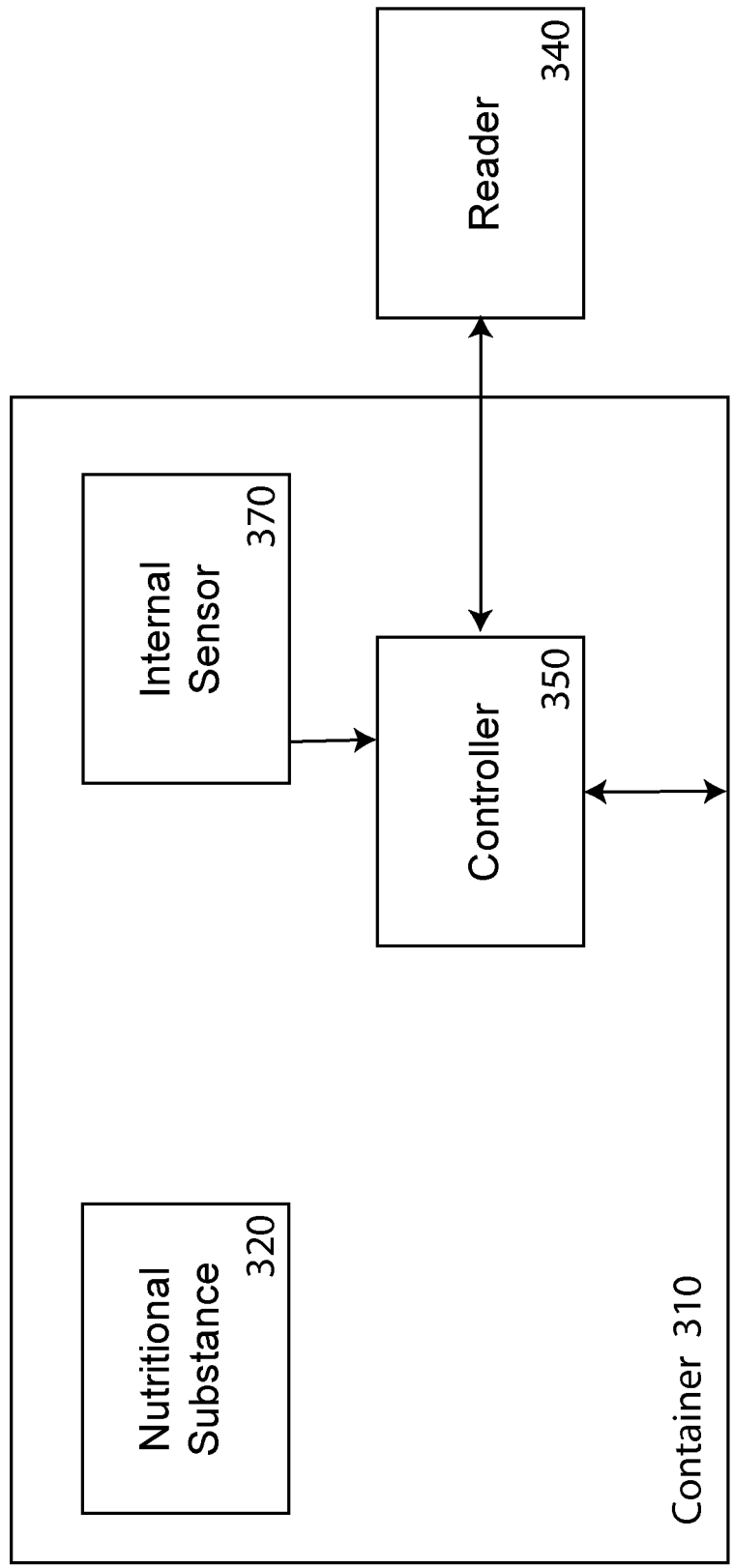
FIG. 7 shows a schematic functional block diagram of the preservation module 300 according to an alternate embodiment of the present invention.

FIG. 7 shows an embodiment of preservation module 300 wherein container 310 contains nutritional substance 320 as well as controller 350. Controller 350 is connected to internal sensor 370 located either inside, or on the surface of, container 310, such that internal sensor 370 can obtain information regarding the environment internal to container 310. Controller 350 and internal sensor 370 can take the form of electronic components such as a micro-controller and an electronic sensor. However, the controller-sensor combination may also be chemical or organic materials which perform the same function, such as a liquid crystal sensor/display.

When the shipper or user of container 310 desires information from internal sensor 370 the shipper or user can use reader 340 to query internal sensor 370 through controller 350. In the electronic component embodiment, reader 340 could be a user interface device such as a computer which can be electronically connected to internal sensor 370 through controller 350.

In addition to information regarding the environment internal to container 310, information in the controller 350 can include creation or origin information from the creation of the nutritional substance 320 and/or prior preservation or transformation information. Information in the controller 350 might additionally include identification information, such as a dynamic information identifier provided on the nutritional substance, which is associated with source and origin information or information regarding prior transformation or prior storage or prior transport of the nutritional substance 320 and other historic information preserved in information module 100. A shipper, or user, of container 310 can operatively connect to controller 350 using reader 340 to retrieve information stored therein, such as the identification information and information from internal sensor 370. Information module 100 can connect to controller 350 directly, or using reader 340, to retrieve and preserve information stored therein, such as the identification information and information from internal sensor 370, and can further associate that information with the dynamic information identifier provided on the nutritional substance. Alternatively, controller 350 or reader 340 can transmit information stored in or collected by controller 350 to information module 100 and can further associate the transmitted information with the dynamic information identifier provided on the nutritional substance A consumer or other member of the nutritional substance supply system would then be able to retrieve from information module 100 the information that was stored in controller 350 by using the dynamic information identifier associated with the nutritional substance and provided on the nutritional substance.

In an additional embodiment, controller 350 can modify the operation of container 310 so as modify the preservation capabilities of container 310. For example, if the interior environment of container 310 would adversely affect the nutritional substance 320, container 310 could adjust the internal environment of container 310 to better preserve the nutritional substance. If nutritional substance needs to be kept within a certain temperature range to preserve its nutritional, organoleptic or aesthetic values or properties, and the internal sensor 370 provides internal temperature information to controller 350, controller 350 could modify container 310 so as to maintain nutritional substance 320 within the required temperature range.

Figure 8:
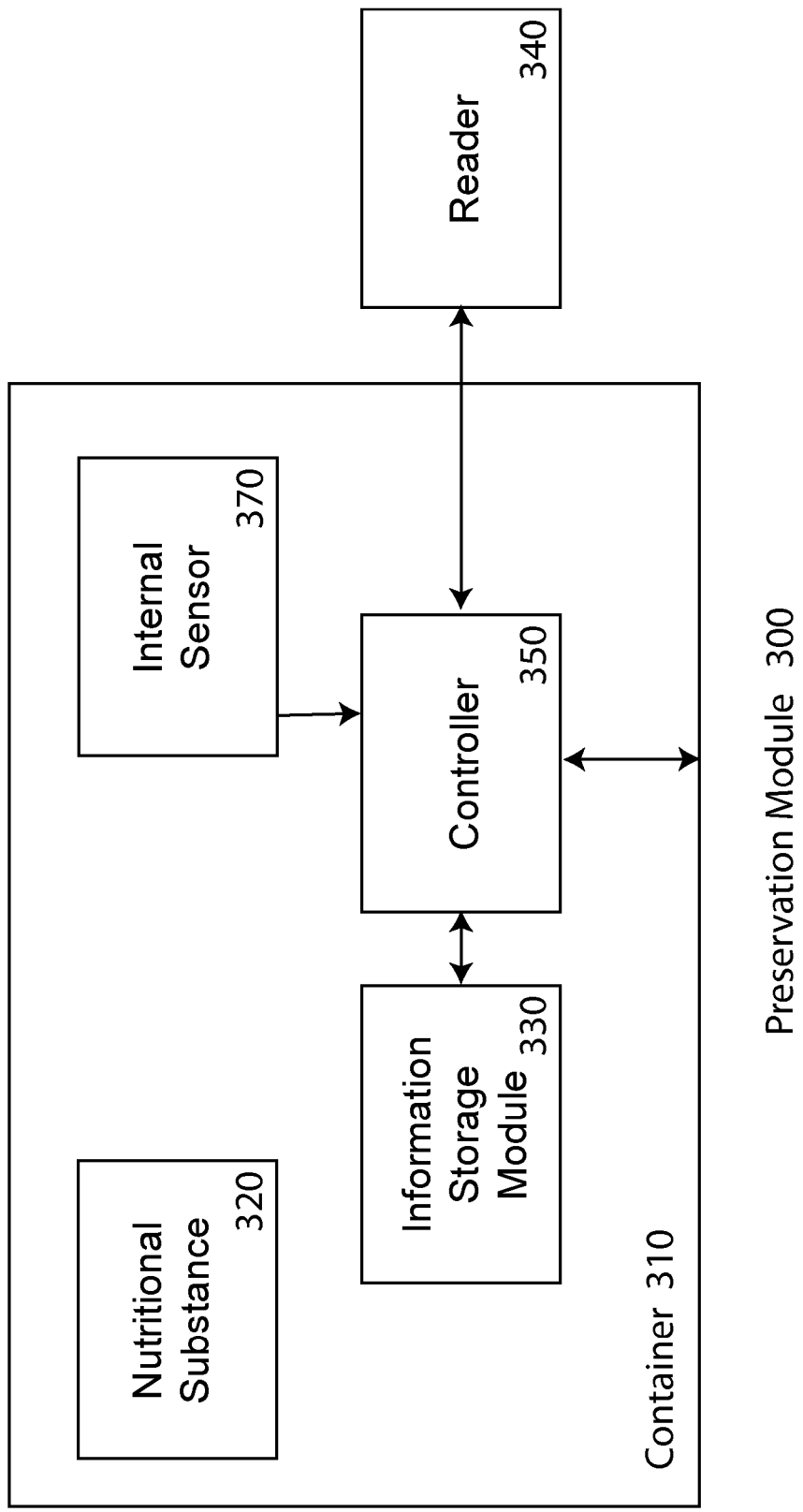
FIG. 8 shows a schematic functional block diagram of the preservation module 300 according to an alternate embodiment of the present invention.

In FIG. 8, preservation module 300 includes container 310 which contains nutritional substance 320, controller 350, and information storage module 330. Internal sensor 370 is positioned such that it can provide information on the internal environment to container 310. Information from the internal sensor and information storage module can be retrieved by connecting reader 340 to container 310.

In this embodiment, information regarding the internal environment sensed by internal sensor 370 and provided to controller 350 can be stored in information storage module 330. In addition to information regarding the environment internal to container 310, information in the information storage module 330 can include creation or origin information from the creation of the nutritional substance 320 and/or prior preservation or transformation information and other historic information regarding the nutritional substance 320. Information in the information storage module 330 might additionally include identification information, such as a dynamic information identifier provided on the nutritional substance, which is associated with source and origin information or information regarding prior transformation or prior storage or prior transport of the nutritional substance 320 and other historic information preserved in information module 100. A shipper, or user, of container 310 can operatively connect to information storage module 330 using reader 340 to retrieve information stored in information storage module 330. Information module 100 can connect to controller 350 directly, or using reader 340, to retrieve and preserve information stored in information storage module 330, and can further associate that information with the dynamic information identifier provided on the nutritional substance. Alternatively, controller 350 or reader 340 can transmit information stored in information storage module 330 to information module 100 and can further associate the transmitted information with the dynamic information identifier provided on the nutritional substance. A consumer or other member of the nutritional substance supply system would then be able to retrieve from information module 100 the information that was stored in information storage module 330 by using the dynamic information identifier associated with the nutritional substance and provided on the nutritional substance. This storage of internal environment information can be used to record a history that the internal environment of container 310 has been subjected to. This would allow the shipper or user of container 310 to understand the internal environment the container has been subjected to during the time it has preserved the nutritional substance. Such information can be used to determine if the nutritional substance is no longer safe for consumption or has been degraded such that the nutritional substance is no longer in an optimal state. Additionally, the user of the nutritional substance could modify its transformation, conditioning, or consumption according to any changes that may have occurred because of the internal conditions of the container.

In an additional embodiment, controller 350 can modify the operation of container 310 so as modify the preservation capabilities of container 310. For example, if the internal environment of container 310 would adversely affect the nutritional substance 320, container 310 could adjust the internal environment of container 310 to better preserve the nutritional substance. Controller 350 can analyze the historic information from internal sensor 370, stored in information storage module 330 to determine any long-term internal environmental conditions. If nutritional substance needs to be kept within a certain temperature range to preserve its nutritional, organoleptic or aesthetic values or properties, and the internal sensor 370 provides internal temperature information to controller 350, controller 350 could modify container 310 so as to maintain nutritional substance 320 within the required temperature range.

In an alternate embodiment reader 340 can also write to information storage module 330. In this embodiment, information regarding the container and/or nutritional substance 320 can be modified or added to information storage module 330 by the user or shipper.

Figure 9:
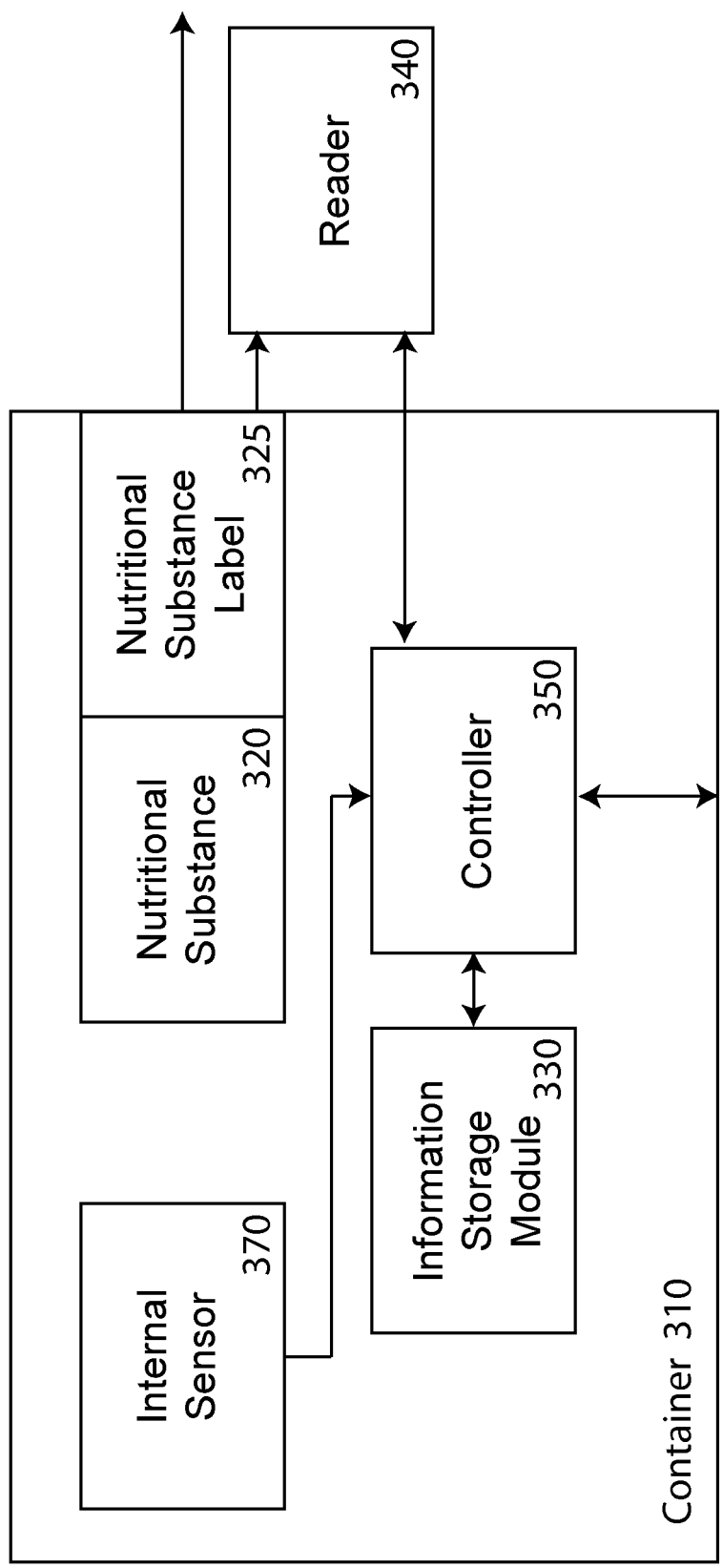
FIG. 9 shows a schematic functional block diagram of the preservation module 300 according to an alternate embodiment of the present invention.

FIG. 9 shows an alternate embodiment of the present invention. Preservation module 300 includes container 310 which contains nutritional substance 320, nutritional substance label 325, controller 350, and information storage module 330. Internal sensor 370 is positioned such that it can provide information on the internal environment to container 310. Information from the internal sensor and information storage module can be retrieved by connecting reader 340 to container 310. Nutritional substance label 325 is attached to nutritional substance 320 so as to sense, measure, and/or indicate the current state of nutritional substance 320. Nutritional substance label 325 can be read by reader 340. Nutritional substance label 325 could be a material/chemical tag that, through a physical reaction with the surface of nutritional substance 320, provides information regarding the nutritional, organoleptic or aesthetic values or properties or state of the nutritional substance, including where nutritional substance 320 is in its life cycle. As an example, this label/tag can change color as a fruit, cheese or wine matures across time. It could also indicate if it detects traces of pesticides, hormones, allergens, harmful or dangerous bacteria, or any other substances.

In this embodiment, information regarding the internal environment sensed by internal sensor 370 and provided to controller 350 can be stored in information storage module 330. In addition to information regarding the environment internal to container 310, information in the information storage module 330 can include creation or origin information from the creation of the nutritional substance 320 and/or prior preservation or transformation information and other historic information regarding the nutritional substance 320. Information in the information storage module 330 might additionally include identification information, such as a dynamic information identifier provided on the nutritional substance, which is associated with source and origin information or information regarding prior transformation or prior storage or prior transport of the nutritional substance 320 and other historic information preserved in information module 100. The dynamic information identifier might be incorporated onto nutritional substance label 325 or could be independent of nutritional substance label 325. A shipper, or user, of container 310 can operatively connect to information storage module 330 using reader 340 to retrieve information stored in information storage module 330. Information module 100 can connect to controller 350 directly, or using reader 340, to retrieve and preserve information stored in information storage module 330, and can further associate that information with the dynamic information identifier provided on the nutritional substance. Alternatively, controller 350 or reader 340 can transmit information stored in information storage module 330 to information module 100 and can further associate the transmitted information with the dynamic information identifier provided on the nutritional substance. A consumer or other member of the nutritional substance supply system would then be able to retrieve from information module 100 the information that was stored in information storage module 330 by using the dynamic information identifier associated with the nutritional substance and provided on the nutritional substance. This storage of internal environment information can be used to record a history that the internal environment container 310 has been subjected to. This would allow the shipper or user of container 310 to understand the internal environment the container has been subjected to during the time it has preserved the nutritional substance. Such information can be used to determine if the nutritional substance is no longer safe for consumption or has been degraded such that the nutritional substance is no longer in an optimal state. Additionally, the user of the nutritional substance could modify its transformation, conditioning, or consumption according to any changes that may have occurred because of the internal conditions of the container.

In an additional embodiment, controller 350 can modify the operation of container 310 so as modify the preservation capabilities of container 310. For example, if the internal environment of container 310 would adversely affect the nutritional substance 320, container 310 could adjust the internal environment of container 310 to better preserve the nutritional substance. Controller 350 can analyze the historic information from internal sensor 370, stored in information storage module 330 to determine any long-term internal environmental conditions. If nutritional substance needs to be kept within a certain temperature range to preserve its nutritional, organoleptic or aesthetic values or properties, and the internal sensor 370 provides internal temperature information to controller 350, controller 350 could modify container 310 so as to maintain nutritional substance 320 within the required temperature range.

In an alternate embodiment reader 340 can also write to information storage module 330. In this embodiment, information regarding the container and/or nutritional substance 320 can be modified or added to information storage module 330 by the user or shipper.

Figure 10:
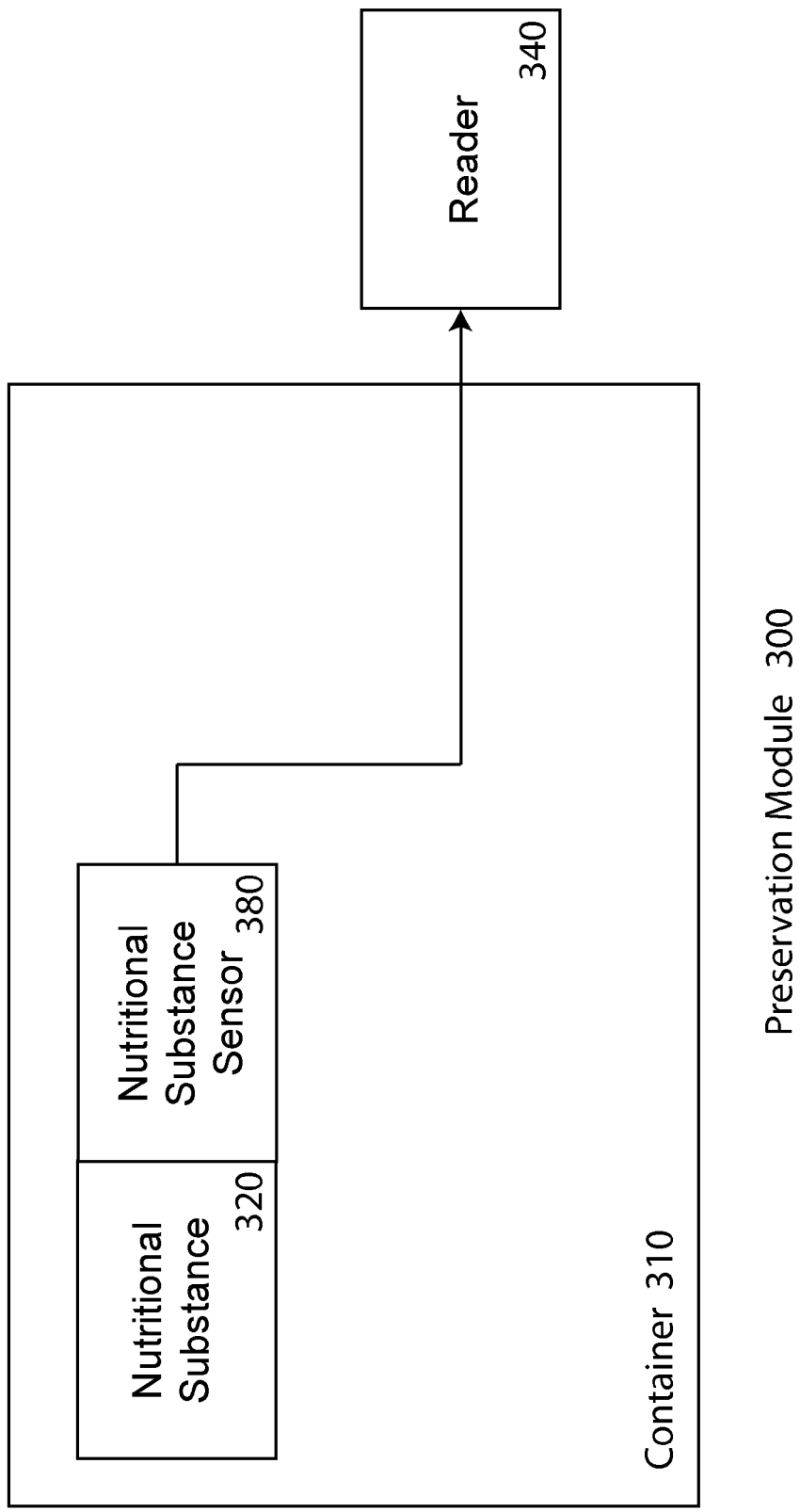
FIG. 10 shows a schematic functional block diagram of the preservation module 300 according to an alternate embodiment of the present invention.

FIG. 10 shows embodiment of preservation module 300 wherein container 310 contains nutritional substance 320 as well as nutritional substance sensor 380 in contact with nutritional substance 320, such that nutritional substance sensor 380 can obtain information regarding the nutritional substance 320 in container 310. Nutritional substance sensor 380 can be connected to reader 340 to obtain the nutritional substance 320 condition. Nutritional substance sensor 380 and reader 340 can take the form of electronic components such as an electronic sensor and electronic display. However, the reader-sensor combination may also be chemical or organic materials which perform the same function, such as a liquid crystal sensor/display.

In this embodiment, information regarding the condition of the nutritional substance 320 sensed by nutritional substance sensor 380 can be retrieved by reader 340. In addition to information regarding the condition of nutritional substance 320 in container 310, information in the nutritional substance sensor 380 can include creation or origin information from the creation of the nutritional substance 320 and/or prior preservation or transformation information and other historical information. Information in the nutritional substance sensor 380 might additionally include identification information, such as a dynamic information identifier provided on the nutritional substance, which is associated with source and origin information or information regarding prior transformation or prior storage or prior transport of the nutritional substance 320 and other historic information preserved in information module 100. A shipper, or user, of container 310 can operatively connect to nutritional substance sensor 380 using reader 340 to retrieve information stored therein. Information module 100 can connect to reader 340 to retrieve and preserve information stored or collected by nutritional substance sensor 380, and can further associate that information with the dynamic information identifier provided on the nutritional substance. Alternatively, nutritional substance sensor 380 or reader 340 can transmit information stored in or collected by nutritional substance sensor 380 to information module 100 and can further associate the transmitted information with the dynamic information identifier provided on the nutritional substance. A consumer or other member of the nutritional substance supply system would then be able to retrieve from information module 100 the information that was stored in or collected by nutritional substance sensor 380 by using the dynamic information identifier associated with the nutritional substance and provided on the nutritional substance. This would allow the shipper or user of container 310 to understand the condition of the nutritional substance during the time it is been preserved. Such information can be used to determine if the nutritional substance is no longer safe for consumption or has been degraded such that the nutritional substance is no longer in an optimal state. Additionally, the user of the nutritional substance could modify its transformation, conditioning, or consumption according to any changes that may have occurred because of the internal conditions of the container.

Figure 11:
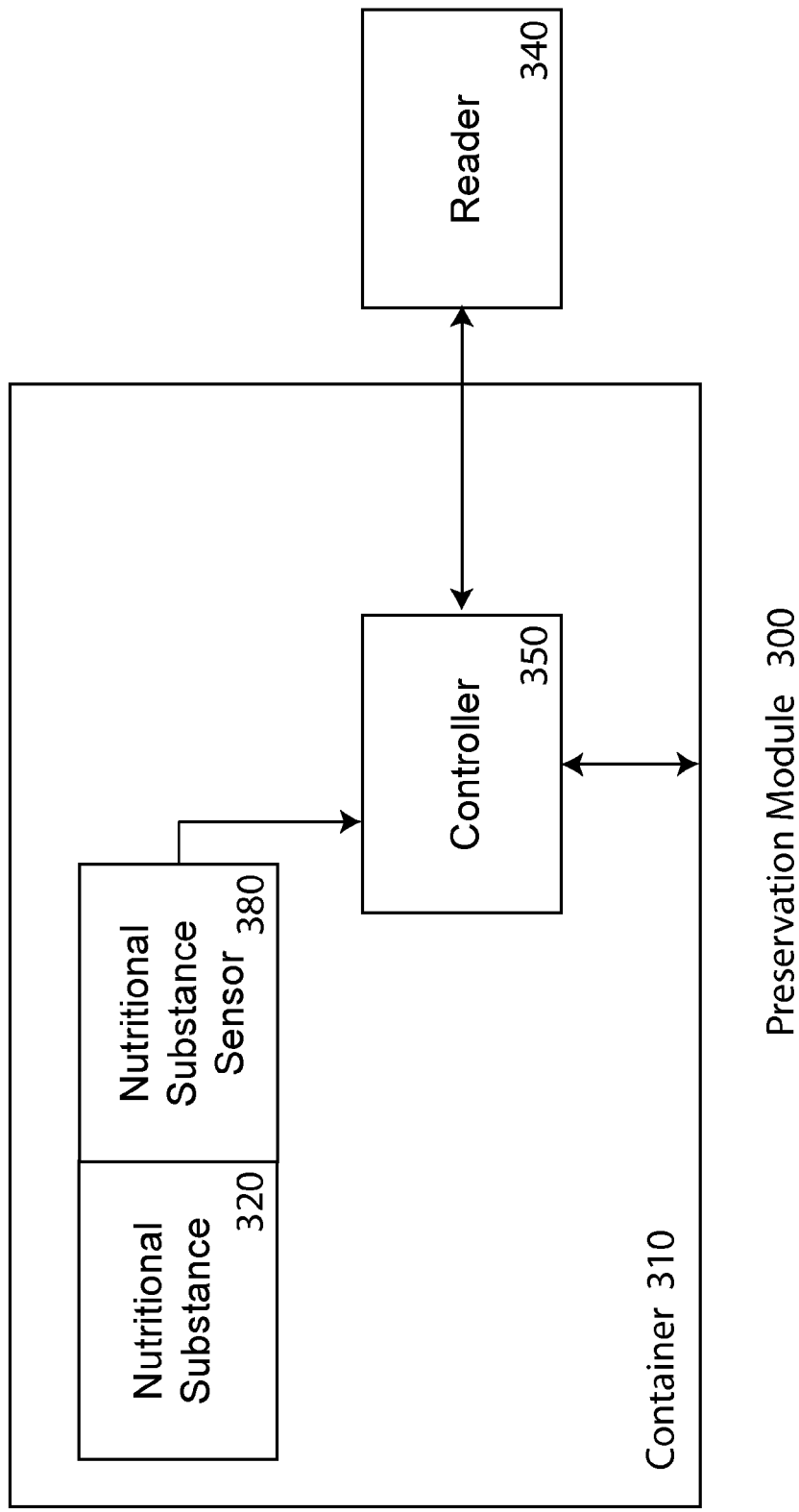
FIG. 11 shows a schematic functional block diagram of the preservation module 300 according to an alternate embodiment of the present invention.

FIG. 11 shows embodiment of preservation module 300 wherein container 310 contains nutritional substance 320 as well as controller 350. Controller 350 is connected to nutritional substance sensor 380. Controller 350 and nutritional substance sensor 380 can take the form of electronic components such as a micro-controller and an electronic sensor. However, the controller-sensor combination may also be chemical or organic materials which perform the same function, such as a liquid crystal sensor/display.

When the shipper or user of container 310 desires information from nutritional substance sensor-380 the shipper or user can use reader 340 to query nutritional substance sensor 380 through controller 350. In the electronic component embodiment, reader 340 could be a user interface device such as a computer which can be electronically connected to nutritional substance sensor 380 through controller 350.

In addition to information regarding the environment internal to container 310, information in the controller 350 can include creation or origin information from the creation of the nutritional substance 320 and/or prior preservation or transformation information and other historical information.

Information in the controller 350 might additionally include identification information, such as a dynamic information identifier provided on the nutritional substance, which is associated with source and origin information or information regarding prior transformation or prior storage or prior transport of the nutritional substance 320 and other historic information preserved in information module 100. A shipper, or user, of container 310 can operatively connect to controller 350 using reader 340 to retrieve information stored therein, such as the identification information and information from nutritional substance sensor 380. Information module 100 can connect to controller 350 directly, or using reader 340, to retrieve and preserve information stored therein, such as the identification information and information from nutritional substance sensor 380, and can further associate that information with the dynamic information identifier provided on the nutritional substance. Alternatively, controller 350 or reader 340 can transmit information stored in or collected by controller 350 to information module 100 and can further associate the transmitted information with the dynamic information identifier provided on the nutritional substance A consumer or other member of the nutritional substance supply system would then be able to retrieve from information module 100 the information that was stored in controller 350 by using the dynamic information identifier associated with the nutritional substance and provided on the nutritional substance.

In an additional embodiment, controller 350 can modify the operation of container 310 so as modify the preservation capabilities of container 310. For example, if the interior environment of container 310 is adversely affecting the nutritional substance 320, container 310 could adjust the nutritional substance environment of container 310 to better preserve the nutritional substance. If nutritional substance needs to be kept within a certain temperature range to preserve its nutritional, organoleptic or aesthetic values or properties, and the nutritional substance sensor 380 provides nutritional substance temperature information to controller 350, controller 350 could modify container 310 so as to maintain nutritional substance 320 within the required temperature range.

Figure 12:
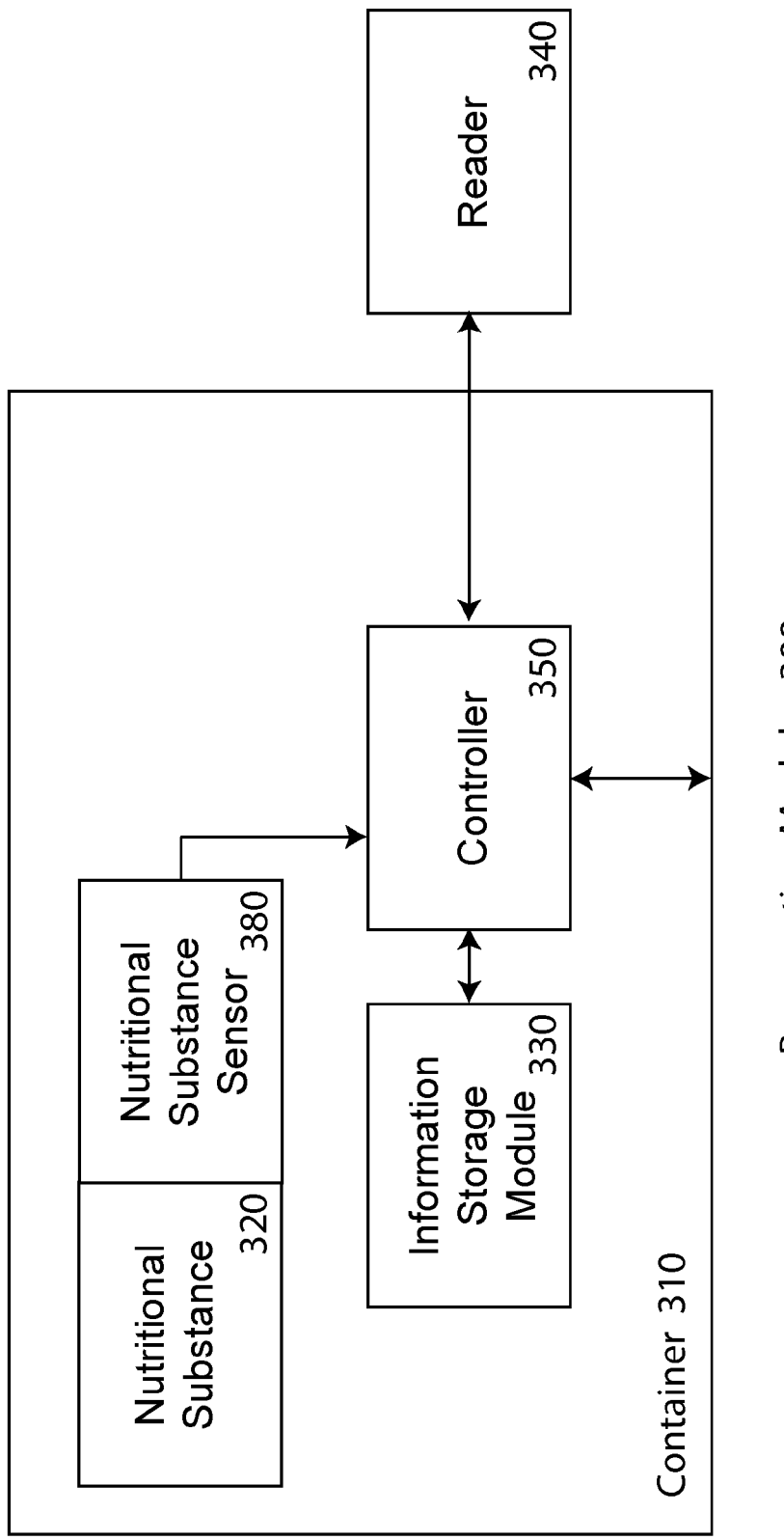
FIG. 12 shows a schematic functional block diagram of the preservation module 300 according to an alternate embodiment of the present invention.

In FIG. 12, preservation module 300 includes container 310 which contains nutritional substance 320, controller 350, and information storage module 330. Nutritional substance sensor 380 is positioned such that it can provide information on the nutritional substance in container 310. Information from the nutritional substance sensor 380 and information storage module can be retrieved by connecting reader 340 to controller 350.

In addition to information regarding the condition of nutritional substance 320 inside container 310, information in the information storage module 330 can include creation or origin information from the creation of the nutritional substance 320 and/or prior preservation or transformation information and other historic information regarding the nutritional substance 320. Information in the information storage module 330 might additionally include identification information, such as a dynamic information identifier provided on the nutritional substance, which is associated with source and origin information or information regarding prior transformation or prior storage or prior transport of the nutritional substance 320 and other historic information preserved in information module 100. A shipper, or user, of container 310 can operatively connect to information storage module 330 using reader 340 to retrieve information stored in information storage module 330. Information module 100 can connect to controller 350 directly, or using reader 340, to retrieve and preserve information stored in information storage module 330, and can further associate that information with the dynamic information identifier provided on the nutritional substance. Alternatively, controller 350 or reader 340 can transmit information stored in information storage module 330 to information module 100 and can further associate the transmitted information with the dynamic information identifier provided on the nutritional substance. A consumer or other member of the nutritional substance supply system would then be able to retrieve from information module 100 the information that was stored in information storage module 330 by using the dynamic information identifier associated with the nutritional substance and provided on the nutritional substance. This would allow the shipper or user of container 310 to understand the condition of nutritional substance 320 during the time it has been preserved. Such information can be used to determine if the nutritional substance is no longer safe for consumption or has been degraded such that the nutritional substance is no longer in an optimal state. Additionally, the user of the nutritional substance could modify its transformation, conditioning, or consumption according to any changes that may have occurred during storage in the container.

In an additional embodiment, controller 350 can modify the operation of container 310 so as modify the preservation capabilities of container 310. For example, if the nutritional substance 320 is being adversely affected, controller 350 could adjust the container 310 to better preserve the nutritional substance. Controller 350 can analyze the historic information from nutritional substance sensor 380 stored in information storage module 330 to determine any long-term nutritional substance condition trends that may need modification. If the nutritional substance sensor 380 provides nutritional substance information to controller 350 indicating a trend that needs modification, controller 350 could modify container 310 such that the trend of nutritional substance condition is more desirable.

In an alternate embodiment reader 340 can also write to information storage module 330. In this embodiment, information regarding the container and/or nutritional substance 320 can be modified or added to information storage module 330 by the user or shipper.

Figure 13:
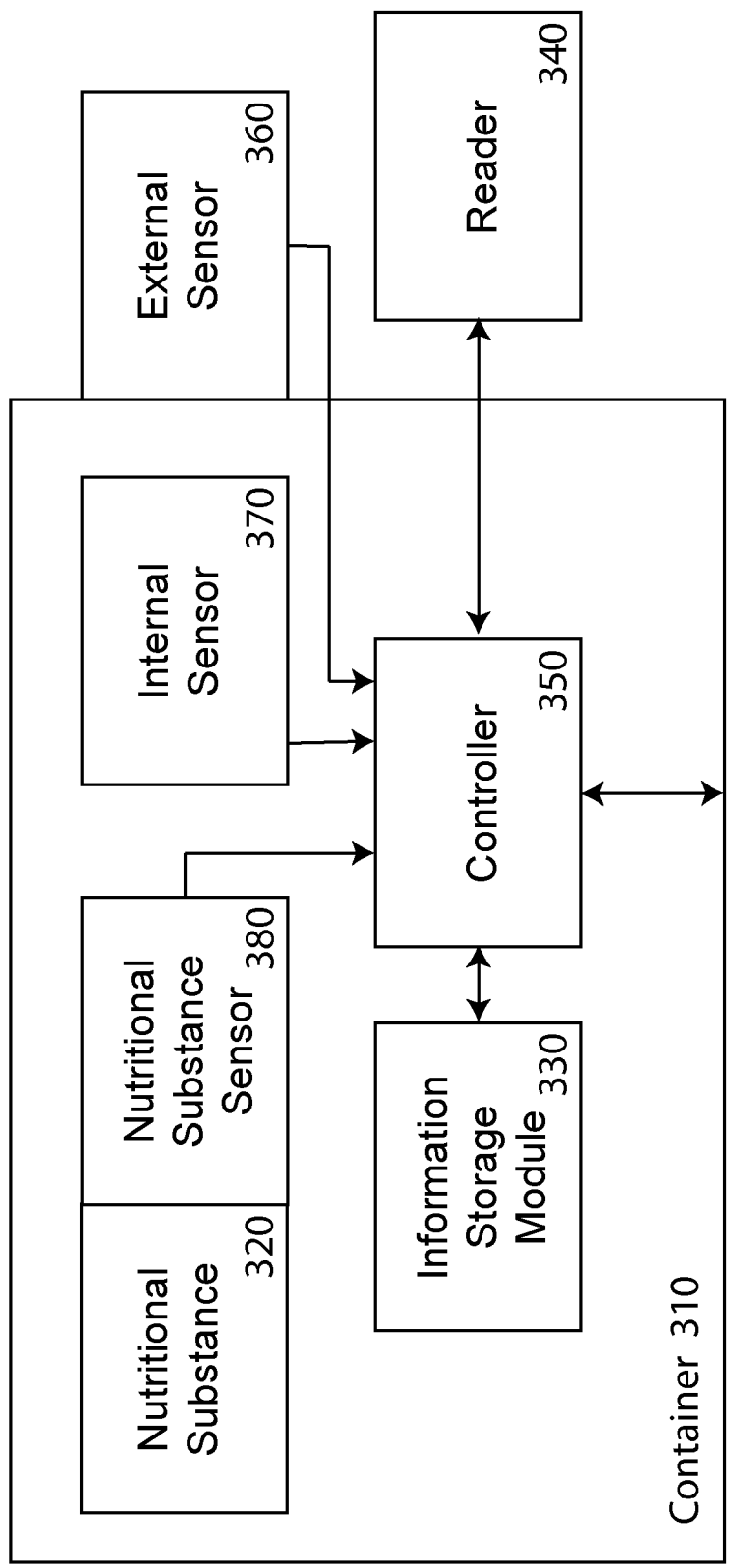
FIG. 13 shows a schematic functional block diagram of the preservation module 300 according to an alternate embodiment of the present invention.

FIG. 13 shows another embodiment of preservation module 300. Within container 310 is nutritional substance 320, nutritional substance sensor 380, internal sensor 370, information storage module 330, and controller 350. External sensor 360 is located outside or on the surface of container 310. In operation, controller 350 receives information from nutritional substance sensor 380, internal sensor 370, and external sensor 360. Additionally, controller 350 can store the information received from the three sensors in information storage module 330. Controller 350 can retrieve such stored information and transmit it to reader 340. Reader 340 can also transmit instructions to controller 350.

Information in the information storage module 330 includes information regarding the condition of the nutritional substance from nutritional substance sensor 380, information regarding the environment internal to container 310 from internal sensor 370, and information regarding the environment external to container 310 from external sensor 360. Further, information in the information storage module 330 can include creation or origin information from the creation of the nutritional substance 320 and/or prior preservation or transformation information and other historic information regarding the nutritional substance 320. Information in the information storage module 330 might additionally include identification information, such as a dynamic information identifier provided on the nutritional substance, which is associated with source and origin information or information regarding prior transformation or prior storage or prior transport of the nutritional substance 320 and other historic information preserved in information module 100. A shipper, or user, of container 310 can operatively connect to information storage module 330 using reader 340 to retrieve information stored in information storage module 330. Information module 100 can connect to controller 350 directly, or using reader 340, to retrieve and preserve information stored in information storage module 330, and can further associate that information with the dynamic information identifier provided on the nutritional substance. Alternatively, controller 350 or reader 340 can transmit information stored in information storage module 330 to information module 100 and can further associate the transmitted information with the dynamic information identifier provided on the nutritional substance. A consumer or other member of the nutritional substance supply system would then be able to retrieve from information module 100 the information that was stored in information storage module 330 by using the dynamic information identifier associated with the nutritional substance and provided on the nutritional substance. This would allow the shipper or user of container 310 to understand the condition of nutritional substance 320 during the time it has been preserved, as well as the environment internal and external to container 310 during the preservation period. Such information can be used to determine if the nutritional substance is no longer safe for consumption or has been degraded such that the nutritional substance is no longer in an optimal state. Additionally, the user of the nutritional substance could modify its transformation, conditioning, or consumption according to any changes that may have occurred during storage in the container.

In an additional embodiment, controller 350 can modify the operation of container 310 so as modify the preservation capabilities of container 310. For example, if the nutritional substance 320 is being adversely affected, controller 350 could adjust the container 310 to better preserve the nutritional substance. Controller 350 can analyze the historic information stored in information storage module 330 regarding nutritional substance sensor 380, internal sensor 370, and external sensor 360 to determine any long-term nutritional substance condition trends, internal environment trends, and external environment trends that may need modification. If the nutritional substance sensor 380 or the internal sensor 370 or the external sensor 360 provide information to controller 350 indicating a trend that requires modification of container 310, controller 350 could modify container 310 such that the trend is offset or compensated for.

In an alternate embodiment reader 340 can also write to information storage module 330. In this embodiment, information regarding the container and/or nutritional substance 320 can be modified or added to information storage module 330 by the user or shipper.

As an example, nutritional substance 320 could be bananas being shipped to a distribution warehouse. Bananas are in container 310 which is capable of controlling its internal temperature, humidity, and the level of certain gasses within the container. Creation information as to the bananas is placed in information storage module 330 prior to shipment. During shipment, external sensor 360 measures the temperature and humidity outside container 310. This information is stored by controller 350 in information storage module 330. Controller 350 also receives information on the internal environment within container 310 from internal sensor 370 and stores this information in information storage module 330. This information includes the internal temperature, humidity, and certain gas levels within container 310. Finally, nutritional substance sensor 380, which is attached to the surface of the bananas, provides information as to the state of the bananas to controller 350. This information could include surface temperature, surface humidity, gasses being emitted, and surface chemicals. At any time during its shipment and delivery to the distribution warehouse, reader 340 can be used to retrieve both current information and historic information stored within information storage module 330. Alternatively, at any time during its shipment and delivery to the distribution warehouse, reader 340 or controller 350 can transmit both current information and historic information stored within information storage module 330 to information module 100 so that the information is available for remote retrieval from information module 100.

During shipment, container 310 modifies its internal conditions according to instructions provided by controller 350. Controller 350 contains instructions as to how to preserve, and possibly ripen, the bananas using information stored in information storage module 330 about the creation of the bananas, as well as historical information received from the three sensors, as well as current information being received from the three sensors. In this manner, preservation module 300 can preserve and optimize nutritional, organoleptic or aesthetic values or properties or attributes of the bananas while they are being shipped and stored.

It will be understood that subsets of the embodiment described herein can operate to achieve the goals stated herein. In one embodiment, nutritional substance sensor 380, internal sensor 370, external sensor 360, information storage module 330, controller 350, reader 340, and parts of container 310 are each electrical or electromechanical devices which perform each of the indicated functions. However, it is possible for some or all of these functions to be done using chemical and/or organic compounds. For example, a specifically designed plastic wrap for bananas can sense the exterior conditions of the package, the interior conditions of the package, and control gas flow through its surface so as to preserve and ripen the bananas.

Unless the context clearly requires otherwise, throughout the description and the claims, the words "comprise," "comprising," and the like are to be construed in an inclusive sense (i.e., to say, in the sense of "including, but not limited to"), as opposed to an exclusive or exhaustive sense. As used herein, the terms "connected," "coupled," or any variant thereof means any connection or coupling, either direct or indirect, between two or more elements. Such a coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the invention is not intended to be exhaustive or to limit the invention to the precise form disclosed above. While specific examples for the invention are described above for illustrative purposes, various equivalent modifications are possible within the scope of the invention, as those skilled in the relevant art will recognize. While processes or blocks are presented in a given order in this application, alternative implementations may perform routines having steps performed in a different order, or employ systems having blocks in a different order. Some processes or blocks may be deleted, moved, added, subdivided, combined, and/or modified to provide alternative or sub-combinations. Also, while processes or blocks are at times shown as being performed in series, these processes or blocks may instead be performed or implemented in parallel, or may be performed at different times. Further any specific numbers noted herein are only examples. It is understood that alternative implementations may employ differing values or ranges.

The various illustrations and teachings provided herein can also be applied to systems other than the system described above. The elements and acts of the various examples described above can be combined to provide further implementations of the invention.

Any patents and applications and other references noted above, including any that may be listed in accompanying filing papers, are incorporated herein by reference. Aspects of the invention can be modified, if necessary, to employ the systems, functions, and concepts included in such references to provide further implementations of the invention.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

While certain aspects of the invention are presented below in certain claim forms, the applicant contemplates the various aspects of the invention in any number of claim forms. For example, while only one aspect of the invention is recited as a means-plus-function claim under 35 U.S.C. §112, sixth paragraph, other aspects may likewise be embodied as a means-plus-function claim, or in other forms, such as being embodied in a computer-readable medium. Any claims intended to be treated under 35 U.S.C. §112, ¶6 will begin with the words "means for." Accordingly, the applicant reserves the right to add additional claims after filing the application to pursue such additional claim forms for other aspects of the invention.

EXAMPLES

Nutritional substances are commonly preserved utilizing various freezing techniques. While freezing is well recognized as an effective method of preservation, it can cause a degradation of nutritional, organoleptic, or aesthetic value, a negative $\Delta N$, for the nutritional substance being frozen. Additional $\Delta N$ can occur during subsequent storage and transfer of the nutritional substance on its path from being packaged and frozen to being consumed. These additional $\Delta N$s can occur as a result of: frozen storage; transfer to a distributor or retailer; and storage by the distributor or retailer.

Figure 14:
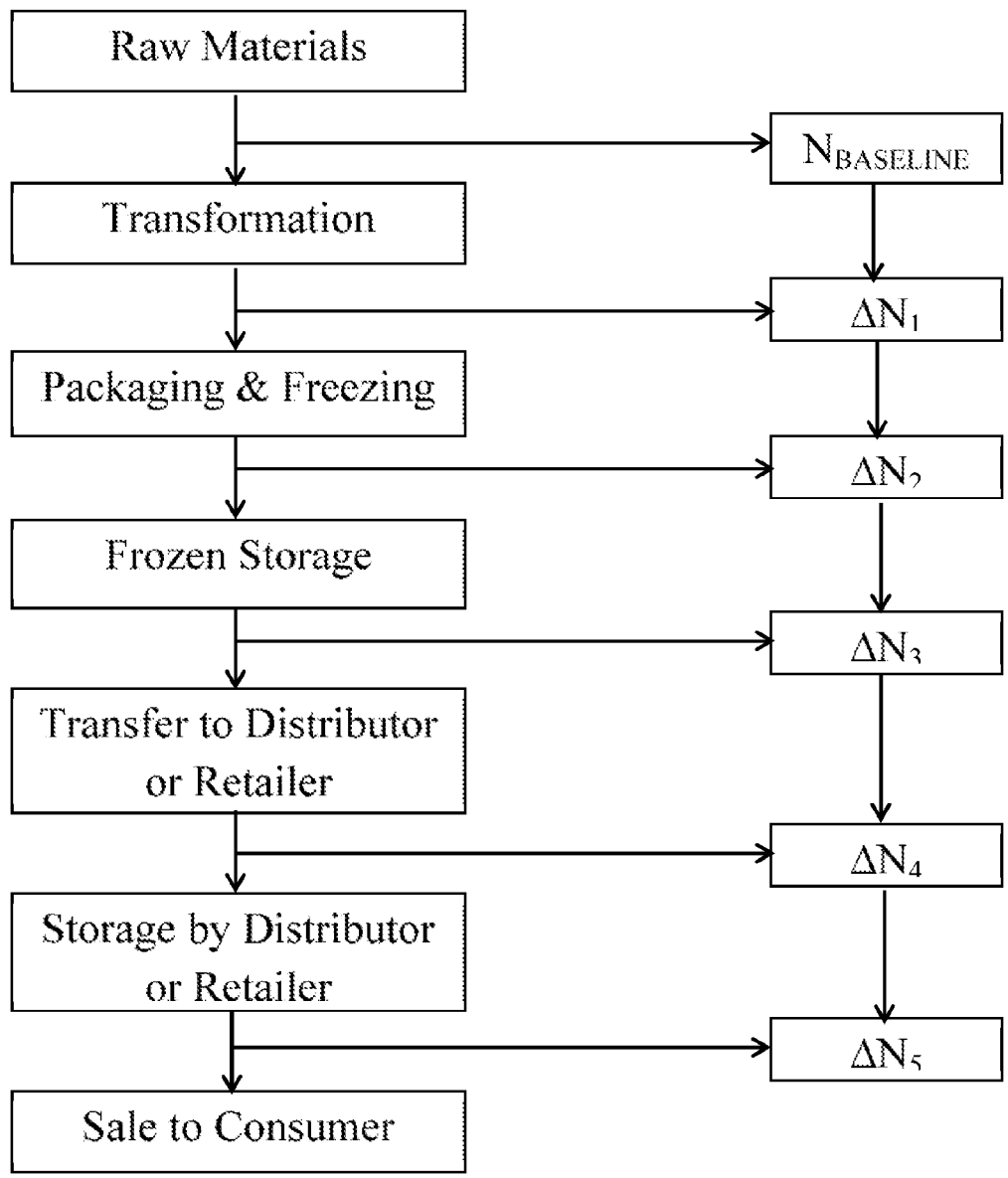
FIG. 14 shows a flow chart of steps that a nutritional substance may go through on its journey through the nutritional substance supply system.

FIG. 14 provides a schematic showing exemplary steps that may occur to a frozen nutritional substance before it is sold to a consumer. FIG. 14 further shows that the nutritional substance has a baseline nutritional, organoleptic, or aesthetic value ($N_{BASELINE}$), then experiences a change in the nutritional, organoleptic, or aesthetic value ($\Delta N$) at each subsequent step before being sold to a consumer.

Some examples will now be provided of how a preservation system for nutritional substances according to the present invention provides beneficial: source and origin information for the nutritional substance; information regarding a change in nutritional, organoleptic, or aesthetic value of the nutritional substance; and information as to a current nutritional, organoleptic, or aesthetic state of the nutritional substance.

In one example, the raw material is freshly caught farm raised salmon. Referring to FIG. 14, when the salmon is first caught it is at its baseline nutritional, organoleptic, and aesthetic value, $N_{BASELINE}$. Transformation of the salmon involves cleaning and cutting the salmon into steaks. From the time the salmon is caught and during the time the salmon is being cleaned and cut, it is advantageous to maintain the salmon at low temperatures, but also to avoid uncontrolled freezing of the salmon. Based on the conditions and amount of time that the salmon is maintained from the time it is caught and during the time it is being cleaned and cut, there will be changes, likely a degradation, in nutritional, organoleptic, or aesthetic value. These changes are shown as $\Delta N_1$ in FIG. 14. The nutritional, organoleptic, or aesthetic state of the salmon following preparation and transformation would be equal to the sum of its baseline nutritional, organoleptic, or aesthetic value and the change in said nutritional, organoleptic, or aesthetic value that occurred during transformation. In other words, the nutritional, organoleptic, or aesthetic value following transformation equals $N_{BASELINE} + \Delta N_1$.

The cleaned and cut salmon steaks are then packaged and frozen. Based on the type of packaging used and the freezing process applied, there will be changes, likely a degradation, in nutritional, organoleptic, or aesthetic value. These changes are shown as $\Delta N_2$ in FIG. 14. The nutritional, organoleptic, or aesthetic state of the salmon following packaging and freezing would be equal to the sum of its baseline nutritional, organoleptic, or aesthetic value and the change in said nutritional, organoleptic, or aesthetic value that occurred during transformation and the change in said nutritional, organoleptic, or aesthetic value that occurred during packaging and freezing. In other words, the nutritional, organoleptic, or aesthetic value following packaging and freezing equals $N_{BASELINE} + \Delta N_1 + \Delta N_2$.

The packaged and frozen salmon steaks are then put into frozen storage. Based on the type of packaging used and the time and conditions of frozen storage, there will be changes, likely a degradation, in nutritional, organoleptic, or aesthetic value. These changes are shown as $\Delta N_3$ in FIG. 14. The nutritional, organoleptic, or aesthetic state of the salmon following frozen storage would be equal to the sum of its baseline nutritional, organoleptic, or aesthetic value and the change in said nutritional, organoleptic, or aesthetic value that occurred during transformation and the change in said nutritional, organoleptic, or aesthetic value that occurred during packaging and freezing and the change in said nutritional, organoleptic, or aesthetic value that occurred during frozen storage. In other words, the nutritional, organoleptic, or aesthetic value following frozen storage equals $N_{BASELINE}+\Delta N_1+\Delta N_2+\Delta N_3$.

The packaged and frozen salmon steaks are eventually transferred to a distributor or retailer. Based on the time and conditions during transfer, there will be changes, likely a degradation, in nutritional, organoleptic, or aesthetic value. These changes are shown as $\Delta N_4$ in FIG. 14. The nutritional, organoleptic, or aesthetic state of the salmon following transfer to a distributor or retailer would be equal to the sum of its baseline nutritional, organoleptic, or aesthetic value and the change in said nutritional, organoleptic, or aesthetic value that occurred during transformation and the change in said nutritional, organoleptic, or aesthetic value that occurred during packaging and freezing and the change in said nutritional, organoleptic, or aesthetic value that occurred during frozen storage and the change in said nutritional, organoleptic, or aesthetic value that occurred during transfer to the distributor or retailer. In other words, the nutritional, organoleptic, or aesthetic value following transfer to distributor equals $N_{BASELINE}+\Delta N_1+\Delta N_2+\Delta N_3+\Delta N_4$.

The packaged and frozen salmon steaks are then stored by the distributor or retailer, awaiting sale to a consumer. Based on the time and conditions of storage by the distributor or retailer, there will be changes, likely a degradation, in nutritional, organoleptic, or aesthetic value. These changes are shown as $\Delta N_5$ in FIG. 14. The nutritional, organoleptic, or aesthetic state of the salmon following storage by a distributor or retailer would be equal to the sum of its baseline nutritional, organoleptic, or aesthetic value and the change in said nutritional, organoleptic, or aesthetic value that occurred during transformation and the change in said nutritional, organoleptic, or aesthetic value that occurred during packaging and freezing and the change in said nutritional, organoleptic, or aesthetic value that occurred during frozen storage and the change in said nutritional, organoleptic, or aesthetic value that occurred during transfer to the distributor or retailer and the change in said nutritional, organoleptic, or aesthetic value that occurred during storage by the distributor or retailer. In other words, the nutritional, organoleptic, or aesthetic value following storage by a distributor or retailer and upon sale to a consumer equals $N_{BASELINE}+\Delta N_1+\Delta N_2+\Delta N_3+\Delta N_4+\Delta N_5$.

For traditional methods of freezing, it is well understood that the quality of frozen nutritional substances is highly dependent on the rate at which it is frozen. Generally, rapid freezing results in higher quality frozen nutritional substances as compared to slow freezing. When freezing is rapid, there are more locations within the nutritional substance where nucleation occurs, that is, where ice crystallization begins. In contrast, when freezing is slow, there are relatively few nucleation sites resulting in larger ice crystals. It is known that these larger ice crystals can cause mechanical damage to cell walls and can further result in cell dehydration.

Examples of common traditional methods used for freezing nutritional substances include air-blast freezers, plate freezers, and liquid nitrogen freezers. These methods of freezing nutritional substances provide various benefits and advantages depending on the nutritional substance being frozen and upon other factors such as production rate, flexibility, equipment cost, and cost to operate. These methods of freezing nutritional substances can further be differentiated by the respective rates of freezing that they can deliver, which as previously discussed, can have a significant impact on the quality of the nutritional substance.

Air-blast freezers are among the oldest and most commonly used types of freezing equipment. They offer good temperature stability and versatility for many types of products. Air is generally used as the freezing medium and can be still air or forced air. The basic process involves placing nutritional substances in freezing rooms called sharp freezers. Still air freezers are the most economical method of freezing and provide the added advantage of a constant temperature during frozen storage. However, still air freezers are the slowest method of freezing due to the low surface heat transfer coefficient of circulating air inside the room.

Contact freezing can be a more efficient method of freezing in terms of heat transfer mechanism. The most common type of contact freezer is the plate freezer. In this case, the product is pressed between hallow metal plates, either horizontally or vertically, with a refrigerant circulating inside the plates. Pressure is applied for good contact. This type of freezing system is only limited to regular-shaped materials like patties or block-shaped packaged products, and is considerably faster than air-blast freezing in these situations.

Liquid nitrogen freezing, also known as flash freezing, is still more rapid than contact freezing methods such as with plate freezers. The refrigerant is liquid Nitrogen, with a boiling temperature of $-196°$ C. at atmospheric pressure, and is sprayed into the freezer, evaporating upon leaving the spray nozzles and upon contact with the nutritional substance. These systems can provide high heat transfer efficiency, but consume Nitrogen in the range of 1.2-kg Nitrogen per 1-kg of nutritional substance. Typical nutritional substances frozen in this type of system include fish fillets.

A non-traditional freezing system that shows great promise for nutritional substances is known as a Cells Alive System, or CAS, developed by ABI. The technology does not depend on rapid rates of freezing to minimize damage caused by ice crystals, yet can deliver results even better than rapid freezing such as liquid Nitrogen freezing, that is with little to no degradation of nutritional, organoleptic, or aesthetic value. CAS technology uses an oscillating electrical field to cause water molecules within the nutritional substance to spin, stopping them from clustering and forming ice crystals that damage cell walls. Additionally, the spinning motion of the water molecules artificially lowers the freezing point of the water within the nutritional substance to approximately $-7°$ C. Once the nutritional substance reaches this temperature, the oscillating electrical field is turned off and the water freezes almost instantaneously from the inside out, causing minimal or no cell damage. The natural life form of the cells of a CAS frozen nutritional substance is retained, without the physical damage to the cell wall and nucleus that results from ice crystal growth during traditional outside-to-inside freezing methods.

While CAS freezing has found selective application for preserving nutritional substances, the focus has been on organoleptic and aesthetic characteristics such as taste, texture, and appearance. The present invention can not only track, preserve, and communicate the values associated with these characteristics and changes in the values associated with these characteristics, it can additionally track, preserve, and communicate the nutritional value and changes in the nutritional value of a nutritional substance. This will be of great value to a consumer, who can now see the nutritional benefit associated with nutritional substances frozen by CAS methods. It will also be of great value to those offering nutritional substances frozen by CAS methods, as tracking and communicating a degradation in nutritional value close to, or equal to, zero will demonstrate that the nutritional substance offers similar or equal nutritional value as compared to freshly caught, freshly slaughtered, or freshly harvested nutritional substances.

Referring to FIG. 14, $\Delta N_2$ represents a change in nutritional, organoleptic, or aesthetic value of the nutritional substance, in this case a change resulting from packaging and freezing of the salmon steaks. Improvement of a nutritional, organoleptic, or aesthetic value would be represented by a positive value for $\Delta N_2$. Maintenance of a nutritional, organoleptic, or aesthetic value would be represented by a zero value for $\Delta N_2$. Degradation of a nutritional, organoleptic, or aesthetic value would be represented by a negative value for $\Delta N_2$. It is understood that while all methods of freezing nutritional substances are intended to minimize degradation of nutritional, organoleptic, or aesthetic value, traditional outside-to-inside freezing methods such as air-blast freezing, contact freezing, and flash freezing are associated with various degrees of cell disruption and accordingly various degrees of nutritional substance $\Delta N$ or degradation, while CAS freezing methods can offer little to no cell disruption and accordingly little to no nutritional substance $\Delta N$ or degradation.

For the purpose of the following example it is understood that the amount of degradation to be expected from air-blast freezing is greater than the amount of degradation to be expected from contact freezing which is greater than the amount of degradation to be expected from liquid Nitrogen freezing which is greater than the amount of degradation to be expected from CAS freezing. Because degradation is represented by a negative number, the relationship can be described as: $\Delta N_2$ air-blast freezing<$\Delta N_2$ contact freezing<$\Delta N_2$ liquid Nitrogen freezing<$\Delta N_2$ CAS freezing≤0. With this context, an example is offered of a preservation system according to the present invention. In this example, a transformer of the salmon steaks provides four varieties of frozen salmon steaks based upon nutritional, organoleptic, or aesthetic values of the product. The products are marketed as: economy; standard; premium; and ultra-premium.

The economy salmon steaks have been packaged and frozen by air-blast freezing, which is known to cause significant degradation, but is economical for the transformer. The standard salmon steaks have been packaged and frozen by contact freezing, such as in a plate freezer, which is known to cause degradation, but less than air-blast freezing. The premium salmon steaks have been packaged and frozen by liquid Nitrogen freezing, also known as flash freezing, which is known to cause less degradation than contact freezing. The ultra-premium salmon steaks have been packaged and frozen by CAS freezing, which is known to cause little to no degradation, which is less than liquid Nitrogen freezing.

The transformer stores its economy and standard products at −18° C., and stores its premium and ultra-premium products at −35° C. It is known that degradation of nutritional, organoleptic, or aesthetic value during frozen storage will be greater at storage temperatures of −18° C. compared to degradation of nutritional, organoleptic, or aesthetic value during frozen storage at −35° C. Because degradation is represented by a negative number, the relationship can be described as: $\Delta N_3$ frozen storage at −18° C.<$\Delta N_3$ frozen storage at −35° C.

Further, the transformer transfers its economy and standard products to distributors and retailers at −18° C., and transfers its premium and ultra-premium products to distributors and retailers at −35° C. Because degradation is represented by a negative number, the relationship can be described as: $\Delta N_4$ transfer at −18° C.<$\Delta N_4$ transfer at −35° C.

Still further, the transformer requires its distributors or retailers to store the economy, standard, and premium products at −18° C., but requires its distributors or retailers to store the ultra-premium product at −35° C. Because degradation is represented by a negative number, the relationship can be described as: $\Delta N_5$ storage at −18° C.<$\Delta N_4$ storage at −35° C.

The nutritional, organoleptic, or aesthetic value of any of these four salmon steak products from the transformer can be expressed as the sum of its baseline nutritional, organoleptic, or aesthetic value after each step it goes through on its journey through the nutritional substance supply system. After transformation, the nutritional, organoleptic, or aesthetic value of the economy salmon steak=the nutritional, organoleptic, or aesthetic value of the standard salmon steak=the nutritional, organoleptic, or aesthetic value of the premium salmon steak=the nutritional, organoleptic, or aesthetic value of the ultra-premium salmon steak=$N_{BASELINE}+\Delta N_1$.

After packaging and freezing, the nutritional, organoleptic, or aesthetic value of the economy salmon steak=$N_{BASELINE}+\Delta N_1+\Delta N_2$ air-blast freezing. After packaging and freezing, the nutritional, organoleptic, or aesthetic value of the standard salmon steak=$N_{BASELINE}+\Delta N_1+\Delta N_2$ contact freezing. After packaging and freezing, the nutritional, organoleptic, or aesthetic value of the premium salmon steak=$N_{BASELINE}+\Delta N_1+\Delta N_2$ liquid Nitrogen freezing. After packaging and freezing, the nutritional, organoleptic, or aesthetic value of the ultra-premium salmon steak=$N_{BASELINE}\Delta N_1+\Delta N_2$ CAS freezing. The relationship between the nutritional, organoleptic, or aesthetic values of the economy, standard, premium, and ultra-premium salmon steaks is: $N_{BASELINE}+\Delta N_1+\Delta N_2$ air-blast freezing<$N_{BASELINE}+\Delta N_1+\Delta N_2$ contact freezing<$N_{BASELINE}+\Delta N_1+\Delta N_2$ liquid Nitrogen freezing<$N_{BASELINE}+\Delta N_1+\Delta N_2$ CAS freezing, respectively.

After frozen storage, the nutritional, organoleptic, or aesthetic value of the economy salmon steak=$N_{BASELINE}+\Delta N_1\Delta N_2$ air-blast freezing+$\Delta N_3$ frozen storage at −18° C. After frozen storage, the nutritional, organoleptic, or aesthetic value of the standard salmon steak $N_{BASELINE}+\Delta N_1+\Delta N_2$ contact freezing+$\Delta N_3$ frozen storage at −18° C. After frozen storage, the nutritional, organoleptic, or aesthetic value of the premium salmon steak=$N_{BASELINE}+\Delta N_1+\Delta N_2$ liquid Nitrogen freezing+$\Delta N_3$ frozen storage at −35° C. After frozen storage, the nutritional, organoleptic, or aesthetic value of the ultra-premium salmon steak=$N_{BASELINE}+\Delta N_1+\Delta N_2$ CAS freezing+$\Delta N_3$ frozen storage at −35° C. The relationship between the nutritional, organoleptic, or aesthetic values of the economy, standard, premium, and ultra-premium salmon steaks is: $N_{BASELINE}+\Delta N_1+\Delta N_2$ air-blast freezing+$\Delta N_3$ frozen storage at −18° C.<$N_{BASELINE}+\Delta N_1+\Delta N_2$ contact freezing+$\Delta N_3$ frozen storage at −18° C.<$N_{BASELINE}+\Delta N_1+\Delta N_2$ liquid Nitrogen freezing+$\Delta N_3$ frozen storage at −35° C.<$N_{BASELINE}+\Delta N_1+\Delta N_2$ CAS freezing+$\Delta N_3$ frozen storage at −35° C., respectively.

After transfer to a distributor or retailer, the nutritional, organoleptic, or aesthetic value of the economy salmon steak=$N_{BASELINE}+\Delta N_1+\Delta N_2$ air-blast freezing+$\Delta N_3$ frozen storage at −18° C.+$\Delta N_4$ transfer at −18° C. After transfer to a distributor or retailer, the nutritional, organoleptic, or aesthetic value of the standard salmon steak=$N_{BASELINE}+$ $\Delta N_1 + \Delta N_2$ contact freezing+$\Delta N_3$ frozen storage at −18° C.+$\Delta N_4$ transfer at −18° C. After transfer to a distributor or retailer, the nutritional, organoleptic, or aesthetic value of the premium salmon steak=$N_{BASELINE}$+$\Delta N_1$+$\Delta N_2$ liquid Nitrogen freezing+$\Delta N_3$ frozen storage at −35° C.+$\Delta N_4$ transfer at −35° C. After transfer to a distributor or retailer, the nutritional, organoleptic, or aesthetic value of the ultra-premium salmon steak=$N_{BASELINE}$+$\Delta N_2$ CAS freezing+$\Delta N_3$ frozen storage at −35° C.+$\Delta N_4$ transfer at −35° C. The relationship between the nutritional, organoleptic, or aesthetic values of the economy, standard, premium, and ultra-premium salmon steaks is: $N_{BASELINE}$+$\Delta N_1$+$\Delta N_2$ air-blast freezing+$\Delta N_3$ frozen storage at −18° C.+$\Delta N_4$ transfer at −18° C.<$N_{BASELINE}$+$\Delta N_1$+$\Delta N_2$ contact freezing+$\Delta N_3$ frozen storage at −18° C.+$\Delta N_4$ transfer at −18° C.<$N_{BASELINE}$+$\Delta N_1$+$\Delta N_2$ liquid Nitrogen freezing+$\Delta N_3$ frozen storage at −35° C.+$\Delta N_4$ transfer at −35° C.<$N_{BASELINE}$+$\Delta N_1$+$\Delta N_2$ CAS freezing+$\Delta N_3$ frozen storage at −35° C.+$\Delta N_4$ transfer at −35° C., respectively.

At sale to a consumer, the nutritional, organoleptic, or aesthetic value of the economy salmon steak=$N_{BASELINE}$+$\Delta N_1$+$\Delta N_2$ air-blast freezing+$\Delta N_3$ frozen storage at −18° C.+$\Delta N_4$ transfer at −18° C.+$\Delta N_5$ storage at −18° C. At sale to a consumer, the nutritional, organoleptic, or aesthetic value of the standard salmon steak=$N_{BASELINE}$+$\Delta N_1$+$\Delta N_2$ contact freezing+$\Delta N_3$ frozen storage at −18° C.+$\Delta N_4$ transfer at −18° C.+$\Delta N_5$ storage at −18° C. At sale to a consumer, the nutritional, organoleptic, or aesthetic value of the premium salmon steak=$N_{BASELINE}$+$\Delta N_1$+$\Delta N_2$ liquid Nitrogen freezing+$\Delta N_3$ frozen storage at −35° C.+$\Delta N_4$ transfer at −35° C.+$\Delta N_5$ storage at −18° C. At sale to a consumer, the nutritional, organoleptic, or aesthetic value of the ultra-premium salmon steak=$N_{BASELINE}$+$\Delta N_1$+$\Delta N_2$ CAS freezing+$\Delta N_3$ frozen storage at −35° C.+$\Delta N_4$ transfer at −35° C.+$\Delta N_5$ storage at −35° C. The relationship between the nutritional, organoleptic, or aesthetic values of the economy, standard, premium, and ultra-premium salmon steaks is: $N_{BASELINE}$+$\Delta N_1$+$\Delta N_2$ air-blast freezing+$\Delta N_3$ frozen storage at −18° C.+$\Delta N_4$ transfer at −18° C.+$\Delta N_5$ storage at −18° C.<$N_{BASELINE}$+$\Delta N_1$+$\Delta N_2$ contact freezing+$\Delta N_3$ frozen storage at −18° C.+$\Delta N_4$ transfer at −18° C.+$\Delta N_5$ storage at −18° C.<$N_{BASELINE}$+$\Delta N_1$+$\Delta N_2$ liquid Nitrogen freezing+$\Delta N_3$ frozen storage at −35° C.+$\Delta N_4$ transfer at −35° C.+$\Delta N_5$ storage at −18° C.<$N_{BASELINE}$+$\Delta N_1$+$\Delta N_2$ CAS freezing+$\Delta N_3$ frozen storage at −35° C.+$\Delta N_4$ transfer at −35° C.+$\Delta N_5$ storage at −35° C., respectively.

The consumer, or any other constituent in the nutritional substance supply system, can utilize reference information provided on the nutritional substance package by the transformer in the form of a dynamic information identifier. The dynamic information identifier allows retrieval of source and origin information as well as information regarding changes in nutritional, organoleptic, or aesthetic values of the nutritional substance from a nutritional substance information system, such as from a dynamic nutritional value database.

An example of how this benefits a distributor or retailer of the premium salmon steaks, as compared to products provided without a dynamic information identifier will now be discussed. Upon receiving the premium salmon steaks from transfer, the distributor or retailer can verify source and origin information regarding the premium salmon steaks using the dynamic information identifier provided with the nutritional substance to retrieve the source and origin information from a nutritional substance information system. Further, the distributor or retailer can verify that the nutritional, organoleptic, or aesthetic values expected of this type of product have actually been maintained using the dynamic information identifier provided with the nutritional substance to retrieve information regarding actual $\Delta N$ associated with the premium salmon steaks from a nutritional substance information system. In this way, the distributor or retailer has access to information regarding $\Delta N$ and a current state of nutritional, organoleptic, or aesthetic value of the premium salmon steaks. The nutritional substance information system can communicate the $\Delta N$ at transfer to distributor, which would equal $\Delta N_1$+$\Delta N_2$ liquid Nitrogen freezing+$\Delta N_3$ frozen storage at −35° C.+$\Delta N_4$ transfer at −35° C. The nutritional substance information system can further communicate a current nutritional, organoleptic, or aesthetic value of the premium salmon steaks at transfer to distributor, which would equal $N_{BASELINE}$+$\Delta N_2$ liquid Nitrogen freezing+$\Delta N_3$ frozen storage at −35° C.+$\Delta N_4$ transfer at −35° C. If the product had been received without a dynamic information identifier, the distributor or retailer would have access to very limited information regarding the product, and no information regarding $\Delta N$ or the current state of nutritional, organoleptic, or aesthetic value of the product.

An example of how this benefits a consumer shopping for premium or ultra-premium salmon steaks provided with a dynamic information identifier, as compared to products provided without a dynamic information identifier, will now be discussed. At the supermarket the consumer can verify source and origin information regarding the premium salmon steaks using the dynamic information identifier provided with the nutritional substance to retrieve the source and origin information from a nutritional substance information system. Preferably, this is accomplished with the consumer's smart phone. Further, the consumer can verify that the nutritional, organoleptic, or aesthetic values expected of this type of product have actually been maintained using the dynamic information identifier provided with the nutritional substance to retrieve information regarding actual $\Delta N$ associated with the premium salmon steaks from a nutritional substance information system. In this way, the consumer has access to information regarding $\Delta N$ and a current state of nutritional, organoleptic, or aesthetic value of the premium salmon steaks. The nutritional substance information system can communicate the current $\Delta N$ at the time of the consumer's query, which would equal $\Delta N_1$+$\Delta N_2$ liquid Nitrogen freezing+$\Delta N_3$ frozen storage at −35° C.+$\Delta N_4$ transfer at −35° C.+$\Delta N_5$ storage at −18° C. The nutritional substance information system can further communicate a current nutritional, organoleptic, or aesthetic value of the premium salmon steaks at the time of the consumer's query, which would equal $N_{BASELINE}$+$\Delta N_2$ liquid Nitrogen freezing+$\Delta N_3$ frozen storage at −35° C.+$\Delta N_4$ transfer at −35° C.+$\Delta N_5$ storage at −18° C. Now the consumer can verify source and origin information regarding the ultra-premium salmon steaks using the dynamic information identifier provided with the nutritional substance to retrieve the source and origin information from a nutritional substance information system. Preferably, this is accomplished with the consumer's smart phone. Further, the consumer can verify that the nutritional, organoleptic, or aesthetic values expected of this type of product have actually been maintained using the dynamic information identifier provided with the nutritional substance to retrieve information regarding actual $\Delta N$ associated with the ultra-premium salmon steaks from a nutritional substance information system. In this way, the consumer has access to information regarding $\Delta N$ and a current state of nutritional, organoleptic, or aesthetic value of the ultra-premium salmon steaks. The nutritional substance information system can communicate the current $\Delta N$ at the time of the consumer's query, which would equal $\Delta N_1+\Delta N_2$ CAS freezing+$\Delta N_3$ frozen storage at $-35°$ C.+$\Delta N_4$ transfer at $-35°$ C.+$\Delta N_5$ storage at $-35°$ C. The nutritional substance information system can further communicate a current nutritional, organoleptic, or aesthetic value of the ultra-premium salmon steaks at the time of the consumer's query, which would equal $N_{BASELINE}+\Delta N_1+\Delta N_2$ CAS freezing+$\Delta N_3$ frozen storage at $-35°$ C.+$\Delta N_4$ transfer at $-35°$ C.+$\Delta N_5$ storage at $-35°$ C. If the product had been offered for sale without a dynamic information identifier, the consumer would have access to very limited information regarding the product, and no information regarding $\Delta N$ or the current state of nutritional, organoleptic, or aesthetic value of the product. Because these products were provided with dynamic information identifiers, the consumer can now make an informed comparison of the two products and an informed purchasing decision.

An example of how this benefits a value oriented consumer shopping for economy or standard salmon steaks, as compared to products provided without a dynamic information identifier, will now be discussed. At the supermarket the consumer can verify source and origin information regarding the economy salmon steaks using the dynamic information identifier provided with the nutritional substance to retrieve the source and origin information from a nutritional substance information system. Preferably, this is accomplished with the consumer's smart phone. Further, the consumer can verify that the nutritional, organoleptic, or aesthetic values expected of this type of product have actually been maintained using the dynamic information identifier provided with the nutritional substance to retrieve information regarding actual $\Delta N$ associated with the economy salmon steaks from a nutritional substance information system. In this way, the consumer has access to information regarding $\Delta N$ and a current state of nutritional, organoleptic, or aesthetic value of the economy salmon steaks. The nutritional substance information system can communicate the current $\Delta N$ at the time of the consumer's query, which would equal $\Delta N_1+\Delta N_2$ air-blast freezing+$\Delta N_3$ frozen storage at $-18°$ C.+$\Delta N_4$ transfer at $-18°$ C.+$\Delta N_5$ storage at $-18°$ C. The nutritional substance information system can further communicate a current nutritional, organoleptic, or aesthetic value of the economy salmon steaks at the time of the consumer's query, which would equal $N_{BASELINE}+\Delta N_1+\Delta N_2$ air-blast freezing+$\Delta N_3$ frozen storage at $-18°$ C.+$\Delta N_4$ transfer at $-18°$ C.+$\Delta N_5$ storage at $-18°$ C. Now the consumer can verify source and origin information regarding the standard salmon steaks using the dynamic information identifier provided with the nutritional substance to retrieve the source and origin information from a nutritional substance information system. Preferably, this is accomplished with the consumer's smart phone. Further, the consumer can verify that the nutritional, organoleptic, or aesthetic values expected of this type of product have actually been maintained using the dynamic information identifier provided with the nutritional substance to retrieve information regarding actual $\Delta N$ associated with the standard salmon steaks from a nutritional substance information system. In this way, the consumer has access to information regarding $\Delta N$ and a current state of nutritional, organoleptic, or aesthetic value of the standard salmon steaks. The nutritional substance information system can communicate the current $\Delta N$ at the time of the consumer's query, which would equal $\Delta N_1+\Delta N_2$ contact freezing+$\Delta N_3$ frozen storage at $-18°$ C.+$\Delta N_4$ transfer at $-18°$ C.+$\Delta N_5$ storage at $-18°$ C. The nutritional substance information system can further communicate a current nutritional, organoleptic, or aesthetic value of the standard salmon steaks at the time of the consumer's query, which would equal $N_{BASELINE}+\Delta N_2$ contact freezing+$\Delta N_3$ frozen storage at $-18°$ C.+$\Delta N_4$ transfer at $-18°$ C.+$\Delta N_5$ storage at $-18°$ C. If the product had been offered for sale without a dynamic information identifier, the consumer would have access to very limited information regarding the product, and no information regarding $\Delta N$ or the current state of nutritional, organoleptic, or aesthetic value of the product. Because these products were provided with dynamic information identifiers, the consumer can now make an informed comparison of the two products and an informed purchasing decision.

The invention claimed is:

1. A method of determining nutritional or organoleptic values of nutritional substances comprising the steps of:
    initially freezing a nutritional substance utilizing a type of freezing and storing the nutritional substance in a frozen state following the initial freezing;
    determining an estimated change in nutritional value resulting from the initial freezing of the nutritional substance based on prior freezing of a test nutritional substance that is the same type as the nutritional substance;
    determining an estimated change in nutritional value resulting from the storing of the nutritional substance in the frozen state based on information relating to a time and a temperature of the frozen storage, the estimated change in nutritional value based on prior storing of a test nutritional substance that is the same type as the nutritional substance;
    retrieving a baseline nutritional value of the nutritional substance the baseline nutritional value determined based on prior testing of nutritional substance that is the same type and from the same source as the nutritional substance;
    determining an overall change in nutritional value based on the change in nutritional value resulting from the initial freezing of the nutritional substance and the change in nutritional value resulting from the storing of the nutritional substance in the frozen state;
    determining a current nutritional value based on the overall change in nutritional value and the baseline nutritional value and storing the current nutritional value referenced to a dynamic information identifier in a database;
    receiving a request for the current nutritional value from a consumer; and
    transmitting, in response to the request, the current nutritional value from the database and the overall change in nutritional value for display to the consumer.

2. A method according to claim 1 wherein said type freezing comprises liquid nitrogen freezing.

3. A method according to claim 1 wherein:
    said type of freezing comprises CAS freezing.

4. The method of claim 1, wherein the nutritional value is based on water content.

* * * * *